United States Patent
Vallejo et al.

(10) Patent No.: US 11,918,811 B2
(45) Date of Patent: Mar. 5, 2024

(54) METHOD AND APPARATUS FOR MULTI MODAL OR MULTIPLEXED ELECTRICAL MODULATION OF PAIN USING COMPOSITE ELECTROMAGNETIC FIELDS

(71) Applicant: Medtronic SG, LLC, Minneapolis, MN (US)

(72) Inventors: Ricardo Vallejo, Bloomington, IL (US); David Leonardo Cedeno, Normal, IL (US); Nathan A. Torgerson, Andover, MN (US); Brian Andrew Smith, Apple Valley, MN (US)

(73) Assignee: Medtronic SG, LLC, Minneapolis, MN (US)

( * ) Notice: Subject to any disclaimer, the term of this patent is extended or adjusted under 35 U.S.C. 154(b) by 764 days.

(21) Appl. No.: 16/868,188

(22) Filed: May 6, 2020

(65) Prior Publication Data
US 2020/0353256 A1    Nov. 12, 2020

Related U.S. Application Data

(63) Continuation-in-part of application No. 17/300,305, filed on Jan. 22, 2020.

(60) Provisional application No. 62/843,757, filed on May 6, 2019.

(51) Int. Cl.
| | | |
|---|---|---|
| A61N 1/36 | (2006.01) | |
| A61N 1/05 | (2006.01) | |
| A61N 2/00 | (2006.01) | |
| A61N 2/02 | (2006.01) | |

(52) U.S. Cl.
CPC ....... *A61N 1/36071* (2013.01); *A61N 1/0551* (2013.01); *A61N 1/36062* (2017.08); *A61N 1/36132* (2013.01); *A61N 1/36171* (2013.01); *A61N 1/36175* (2013.01);
(Continued)

(58) Field of Classification Search
CPC ............ A61N 1/36071; A61N 1/36062; A61N 1/0551; A61N 1/36132; A61N 1/36171; A61N 1/36175; A61N 1/36178; A61N 1/36192; A61N 2/006; A61N 2/02
See application file for complete search history.

(56) References Cited

U.S. PATENT DOCUMENTS

| | | | |
|---|---|---|---|
| 2,622,601 | A | 12/1952 | Nemec |
| 3,774,620 | A | 11/1973 | Hansjurgens |
| 4,023,574 | A | 5/1977 | Nemec |

(Continued)

FOREIGN PATENT DOCUMENTS

| | | |
|---|---|---|
| EP | 1011797 | 6/2000 |
| EP | 2630984 A1 | 8/2013 |

(Continued)

OTHER PUBLICATIONS

International Search Report and Written Opinion; International Application No. PCT/US2020/031648; International Filing Date May 6, 2020; dated Oct. 20, 2020; 18 pages.

(Continued)

*Primary Examiner* — Lindsey G Wehrheim
(74) *Attorney, Agent, or Firm* — Shumaker & Sieffert, P.A.

(57) ABSTRACT

Apparatus and methods for managing pain uses a multiplexed modulation/stimulation signal to provide pain relief during spinal cord stimulation or peripheral nerve stimulation.

25 Claims, 22 Drawing Sheets

(52) U.S. Cl.
CPC ..... *A61N 1/36178* (2013.01); *A61N 1/36192* (2013.01); *A61N 2/006* (2013.01); *A61N 2/02* (2013.01)

(56) References Cited

U.S. PATENT DOCUMENTS

| | | | |
|---|---|---|---|
| 4,071,033 | A | 1/1978 | Nawracaj |
| 4,535,777 | A | 8/1985 | Castel |
| 4,960,124 | A | 10/1990 | Masaki |
| 5,224,477 | A | 7/1993 | Itoh |
| 5,269,304 | A | 12/1993 | Mattews |
| 5,324,317 | A | 6/1994 | Reiss |
| 5,683,422 | A | 11/1997 | Rise |
| 5,716,377 | A | 2/1998 | Rise et al. |
| 5,776,170 | A | 7/1998 | MacDonald et al. |
| 5,791,344 | A | 8/1998 | Schulman et al. |
| 5,833,709 | A | 11/1998 | Rise et al. |
| 5,938,690 | A | 8/1999 | Law et al. |
| 5,948,007 | A | 9/1999 | Starkebaum et al. |
| 5,983,141 | A | 11/1999 | Sluijter et al. |
| 6,002,964 | A | 12/1999 | Feler et al. |
| 6,066,163 | A | 5/2000 | John |
| 6,067,470 | A | 5/2000 | Mower |
| 6,246,912 | B1 | 6/2001 | Sluijter et al. |
| 6,366,813 | B1 | 4/2002 | DiLorenzo |
| 6,393,325 | B1 | 5/2002 | Mann |
| 6,463,328 | B1 | 10/2002 | John |
| 6,480,743 | B1 | 11/2002 | Kirpatrick |
| 6,505,078 | B1 | 1/2003 | King et al. |
| 6,539,263 | B1 | 3/2003 | Schiff |
| 6,584,358 | B2 | 6/2003 | Carter et al. |
| 6,591,138 | B1 | 7/2003 | Fischell |
| 6,662,053 | B2 | 12/2003 | Borkan |
| 6,665,562 | B2 | 12/2003 | Gluckman |
| 6,826,429 | B2 | 11/2004 | Johnson |
| 6,923,784 | B2 | 8/2005 | Stein |
| 6,941,171 | B2 | 9/2005 | Mann |
| 7,149,574 | B2 | 12/2006 | Yun et al. |
| 7,228,178 | B2 | 6/2007 | Carroll et al. |
| 7,877,136 | B1 | 1/2011 | Moffitt et al. |
| 8,209,021 | B2 | 6/2012 | Alataris et al. |
| 8,359,102 | B2 | 1/2013 | Alataris et al. |
| 8,364,273 | B2 | 1/2013 | De Ridder |
| 8,380,316 | B2 | 2/2013 | Hagedorn et al. |
| 8,380,318 | B2 | 2/2013 | Kishawi et al. |
| 8,583,239 | B2 | 11/2013 | Pless et al. |
| 8,738,154 | B2 * | 5/2014 | Zdeblick ............... A61N 1/025 607/117 |
| 8,774,927 | B2 | 7/2014 | DeRidder |
| 8,788,044 | B2 | 7/2014 | John |
| 8,977,363 | B2 | 3/2015 | Carroll |
| 8,977,373 | B2 | 3/2015 | Felty et al. |
| 9,138,582 | B2 | 9/2015 | Doan et al. |
| 9,174,053 | B2 | 11/2015 | Zhu |
| 9,462,398 | B2 | 10/2016 | DeRidder |
| 9,572,984 | B2 | 2/2017 | Hou et al. |
| 9,895,539 | B1 | 2/2018 | Heit et al. |
| 10,039,930 | B2 | 8/2018 | Vallejo et al. |
| 10,188,864 | B2 | 1/2019 | John |
| 10,434,311 | B2 | 10/2019 | Vallejo et al. |
| 10,583,299 | B2 | 3/2020 | John |
| 2002/0022866 | A1 | 2/2002 | Borkan |
| 2002/0038137 | A1 | 3/2002 | Stein |
| 2002/0072770 | A1 | 6/2002 | Pless |
| 2002/0169485 | A1 | 11/2002 | Pless |
| 2003/0028072 | A1 | 2/2003 | Fischell |
| 2003/0078633 | A1 | 4/2003 | Firlik |
| 2003/0135248 | A1 | 7/2003 | Stypulkowski |
| 2003/0149457 | A1 | 8/2003 | Tcheng |
| 2003/0204226 | A1 | 10/2003 | Acosta |
| 2004/0002635 | A1 | 1/2004 | Hargrove |
| 2004/0127953 | A1 | 7/2004 | Kilgore et al. |
| 2004/0167584 | A1 | 8/2004 | Carroll et al. |
| 2004/0172089 | A1 | 9/2004 | Whitehurst |
| 2004/0210270 | A1 | 10/2004 | Erickson |
| 2004/0210271 | A1 | 10/2004 | Campen |
| 2004/0215286 | A1 | 10/2004 | Stypulkowski |
| 2004/0267330 | A1 | 12/2004 | Lee et al. |
| 2005/0021104 | A1 | 1/2005 | DiLorenzo |
| 2005/0033381 | A1 | 2/2005 | Carter et al. |
| 2005/0049649 | A1 | 3/2005 | Luders |
| 2005/0049651 | A1 | 3/2005 | Whitehurst |
| 2005/0065575 | A1 | 3/2005 | Dobak |
| 2005/0081847 | A1 | 4/2005 | Lee |
| 2005/0149148 | A1 | 7/2005 | King |
| 2005/0154425 | A1 | 7/2005 | Boveja |
| 2005/0171587 | A1 | 8/2005 | Daglow |
| 2005/0240242 | A1 | 10/2005 | DiLorenzo |
| 2005/0245993 | A1 | 11/2005 | Varrichio |
| 2005/0246003 | A1 | 11/2005 | Black |
| 2006/0004422 | A1 | 1/2006 | De Ridder |
| 2006/0009820 | A1 | 1/2006 | Royle |
| 2006/0015153 | A1 | 1/2006 | Gliner et al. |
| 2006/0074456 | A1 | 4/2006 | Pyles et al. |
| 2006/0095088 | A1 | 5/2006 | De Ridder |
| 2006/0100671 | A1 | 5/2006 | Ridder |
| 2006/0116742 | A1 | 6/2006 | De Ridder |
| 2006/0149337 | A1 | 7/2006 | John |
| 2006/0184211 | A1 | 8/2006 | Gaunt et al. |
| 2007/0060954 | A1 | 3/2007 | Cameron et al. |
| 2007/0073354 | A1 | 3/2007 | Knudson et al. |
| 2007/0083240 | A1 | 4/2007 | Peterson et al. |
| 2007/0150034 | A1 | 6/2007 | Rooney et al. |
| 2007/0213771 | A1 | 9/2007 | Spinner et al. |
| 2007/0265681 | A1 | 11/2007 | Gerber et al. |
| 2009/0018617 | A1 | 1/2009 | Skelton et al. |
| 2009/0024187 | A1 | 1/2009 | Erickson et al. |
| 2010/0057178 | A1 | 3/2010 | Simon |
| 2010/0249875 | A1 | 9/2010 | Kishawi et al. |
| 2011/0106208 | A1 | 5/2011 | Faltys et al. |
| 2011/0184488 | A1 | 7/2011 | De Ridder |
| 2011/0251229 | A1 | 10/2011 | Watkins et al. |
| 2012/0016438 | A1 | 1/2012 | Alataris et al. |
| 2012/0109020 | A1 | 5/2012 | Wagner et al. |
| 2012/0277621 | A1 | 11/2012 | Gerber et al. |
| 2012/0277823 | A1 | 11/2012 | Gerber et al. |
| 2012/0310140 | A1 * | 12/2012 | Kramer ............... A61K 9/0085 604/93.01 |
| 2013/0035745 | A1 | 2/2013 | Ahmed et al. |
| 2013/0211477 | A1 | 8/2013 | Cullen et al. |
| 2013/0303828 | A1 | 11/2013 | Hargrove |
| 2013/0304159 | A1 | 11/2013 | Simon et al. |
| 2013/0325084 | A1 | 12/2013 | Lee |
| 2014/0207203 | A1 | 7/2014 | Ternes et al. |
| 2014/0257428 | A1 | 9/2014 | Zhu |
| 2014/0277265 | A1 | 9/2014 | Khalil et al. |
| 2014/0330345 | A1 | 11/2014 | John |
| 2015/0217117 | A1 | 8/2015 | Hershey |
| 2016/0008604 | A1 | 1/2016 | Doan et al. |
| 2016/0106985 | A1 | 4/2016 | Zhu |
| 2016/0220813 | A1 | 8/2016 | Edgerton et al. |
| 2016/0256689 | A1 | 9/2016 | Vallejo et al. |
| 2016/0271413 | A1 | 9/2016 | Vallejo et al. |
| 2018/0028812 | A1 | 2/2018 | Vallejo et al. |
| 2018/0056073 | A1 | 3/2018 | Torgerson |
| 2018/0243562 | A1 | 8/2018 | Vallejo et al. |
| 2018/0243563 | A1 | 8/2018 | Vallejo et al. |
| 2018/0250513 | A1 | 9/2018 | Vallejo et al. |
| 2018/0353758 | A1 | 12/2018 | Vallejo et al. |
| 2020/0164213 | A1 | 5/2020 | John |
| 2020/0171308 | A1 | 6/2020 | Vallejo et al. |

FOREIGN PATENT DOCUMENTS

| | | | |
|---|---|---|---|
| EP | 2207587 B1 | 4/2015 | |
| EP | 2853285 A1 | 4/2015 | |
| EP | 3156099 B1 | 6/2018 | |
| WO | WO 199519804 | 7/1995 | |
| WO | WO 9843700 A1 | 10/1998 | |
| WO | WO 2004007018 A1 | 1/2004 | |
| WO | WO 2006007048 A3 | 1/2006 | |
| WO | WO 2006057734 A1 | 6/2006 | |
| WO | WO 2007103324 A1 | 9/2007 | |

(56) References Cited

FOREIGN PATENT DOCUMENTS

| WO | WO 2009061813 A1 | 5/2009 |
|---|---|---|
| WO | WO 2009139968 A2 | 11/2009 |
| WO | WO 2016154091 A1 | 9/2016 |

OTHER PUBLICATIONS

Al-Kaisy et al.; "10kHz High-Frequency Spinal Cord Stimulation for Chronic Axial Low Back Pain in Patients with No History of Spinal Surgery: A Preliminary, Prospective, Open Label and Proof-of-Concept Study"; Neuromodulation; Oct. 18, 2015.
Al-Kaisy et al.; "Sustained Effectiveness of 10 kHz High-Frequency Spinal Cord Stimulation for Patients with Chronic, Low Back Pain: 24-Month Results of a Prospective Multicenter Study"; Pain Medicine; 15; pp. 347-354; Mar. 2014.
U.S. Appl. No. 17/060,610, filed Oct. 1, 2020, naming inventor Michael John, Sasha.
Barr, et al., "Electrophysiological interaction through the interstitial space between adjacent unmyelinated parallel fibers" May 1992, Biophys J61, 1164-1175.
Basser, et al., "New currents in electrical stimulation of excitable tissues" (2000) Annu Rev Biomed Eng 2, 377-397. (Applicant points out, in accordance with MPEP 609.04(a), that the year of publication, 2000 is sufficiently earlier than the effective U.S. filing date, so that the particular month of publication is not in issue.).
Bawin, et al., "Effects of modulated very high frequency fields on specific brain rhythms in cats" Aug. 30, 1973, Brain Res 58, 365-384.
Benabid, et al., "Therapeutic electrical stimulation of the central nervous system", C R Biol 328, 177-186, Feb. 2005.
Benyamin et al.; "A Case of Spinal Cord Stimulation in Raynaud's Phenomenon: Can Subthreshold Sensory Stimulation Have an Effect?"; Pain Physician; 10; pp. 473-478; May 2007.
Boston Scientific; "Precision Spinal Cord Stimulator System Clinical Manual"; 91083273-01 Rev A; pp. 1-74; (2015); https://www.uhms.org/images/MEDFAQs/9108327301_RevA_Precision_Spinal_Cord_Stimulator_System_Clinician_Manua.pdf.
Brasil-Neto et al., "Experimental therapy of epilepsy with transcranial magnetic stimulation: lack of additional benefit with prolonged treatment" Mar. 2004, Arq Neuropsiquiatr 62, 21-25.
Bruet, et al., "High frequency stimulation of the subthalamic nucleus increases the extracellular contents of striatal dopamine in normal and partially dopaminergic denervated rats" Jan. 2001, J Neuropathol Exp Neurol 60, 15-24.
Bruet, et al., "Neurochemical mechanisms induced by high frequency stimulation of the subthalamic nucleus: increase of extracellular striatal glutamate and GABA in normal and hemiparkinsonian ratS" Dec. 2003, J Neuropathol Exp Neurol 62, 1228-1240.
Butt et al.; "Histological Findings Using Novel Stimulation Parameters in a Caprine Model"; Ref. F702) from Poster Sessions; European Journal of Pain Supplements; 5; p. 188; (2011) (Applicant points out, in accordance with MPEP 609.04(a), that the year of publication, 2011, is sufficiently earlier than the effective U.S. filing date, so that the particular month of publication is not in issue.).
Cemazar, et al, "Electrochemotherapy of tumours resistant to cisplatin: a study in a murine tumour model" (2001) Eur J Cancer 37, 1166-1172, Jun. 2001.
Ciria, et al., "Antitumor effectiveness of different amounts of electrical charge in Ehrlich and fibrosarcoma Sa-37 tumors" (2004) BMC Cancer 4, 87, Nov. 2004.
Collins English Dictionary; definition of "in place of"; one page; accessed May 19, 2020; https://www.collinsdictionary.com/dictionary/english/in-place-of.
Crapanzano et al.; "High Frequency Spinal Cord Stimulation for Complex Regional Pain Syndrome: A Case Report"; Pain Physician; 19; pp. E177-E182; Dec. 31, 2016.
Cucullo, et al., "Very low intensity alternating current decreases cell proliferation" (2005) Glia 51, 65-72, Mar. 18, 2005.

D'Arcangelo, et al., "Repetitive low-frequency stimulation reduces epileptiform synchronization in limbic neuronal networks" (2005) Neurobiol Dis 19, 119-128, Jun.-Jul. 2005.
Deurloo, et al., "The effect of subthreshold prepulses on the recruitment order in a nerve trunk analyzed in a simple and a realistic volume conductor model" (2001) Biol Cybern 85, 281-291, Oct. 2001.
Dinner, "Effect of sleep on epilepsy" (2002) J Clin Neurophysiol 19, 504-513, Dec. 2002.
Eddicks et al.; "Thoracic Spinal Cord Stimulation Improves Functional Status and Relieves Symptoms in Patients with Refractory Angina Pectoris: the first placebo-controlled randomised study"; Heart; 93; pp. 585-590; Jan. 19, 2007.
Faurie, et al., "Effect of electric field vectoriality on electrically mediated gene delivery in mammalian cells" (2004) Biochim Biophys Acta 1665, 92-100, Oct. 2004.
Gerloff, et al., "Inhibitory influence of the ipsilateral motor cortex on responses to stimulation of the human cortex and pyramidal tract" (1998) J Physiol 510 (Pt 1), 249-259, Jul. 1998.
Gerloff, et al., "Stimulation over the human supplementary motor area interferes with the organization of future elements in complex motor sequences" (1997) Brain 120 (Pt 9), 1587-1602, Oct. 1997.
Goodman, et al., "Preemptive low-frequency stimulation decreases the incidence of amygdala-kindled seizures" (2005) Epilepsia 46, 1-7, Jan. 2005.
Graham-Jones, et al., "Low-frequency septal stimulation increases tyrosine hydroxylase activity in the hippocampus" (1985) Pharmacol Biochem Behav 23, 489-493, Oct. 1985.
Gray, et al., "Resistance to extinction after partial reinforcement training with blocking of the hippocampal theta rhythm by septal stimulation" (1972) Physiol Behav 8, 497-502, Mar. 1972.
Hailong Liu et al., "Modulation of Axonal Excitability by High-Frequency Biphasic Electrical Current," IEEE Transactions on Biomedical Engineering, vol. 56, No. 9, Sep. 1, 2009, pp. 2167-2176.
Hoekema, et al., "Multigrid solution of the potential field in modeling electrical nerve stimulation" (1998) Comput Biomed Res 31, 348-362. (Applicant points out, in accordance with MPEP 609.04(a), that the year of publication, 1998 is sufficiently earlier than the effective U.S. filing date, so that the particular month of publication is not in issue.).
Holsheimer, et al., "Clinical evaluation of paresthesia steering with a new system for spinal cord stimulation" (1998) Neurosurgery 42, 541-547; discussion 547-549, Mar. 1998.
Holsheimer, et al., "Contact combinations in epidural spinal cord stimulation. A comparison by computer modeling" (1991) Stereotact Funct Neurosurg 56, 220-233 (Applicant points out, in accordance with MPEP 609.04(a), that the year of publication, 1991 is sufficiently earlier than the effective U.S. filing date, so that the particular month of publication is not in issue.).
Holsheimer, et al., "Effect of anode-cathode configuration on paresthesia coverage in spinal cord stimulation" (1997) Neurosurgery 41, 654-659; discussion 659-660, Sep. 1997.
Holsheimer, et al., "Effects of electrode geometry and combination on nerve fibre selectivity in spinal cord stimulation" (1995) Med Biol Eng Comput 33, 676-682, Sep. 1995.
Holsheimer, et al., "How do geometric factors influence epidural spinal cord stimulation? A quantitative analysis by computer modeling" (1991) Stereotact Funct Neurosurg 56, 234-249 (Applicant points out, in accordance with MPEP 609.04(a), that the year of publication, 1991, is sufficiently earlier than the effective U.S. filing date, so that the particular month of publication is not in issue.).
Holsheimer, et al., "Optimum electrode geometry for spinal cord stimulation: the narrow bipole and tripole" (1997) Med Biol Eng Comput 35, 493-497, Sep. 1997.
Holt, et al., "Proactive behavioral effects of theta-blocking septal stimulation in the rat" (1983) Behav Neural Biol 39, 7-21, vol. 39, Issue 1, Sep. 1983.
Holt, et al., "Proactive behavioral effects of theta-driving septal stimulation on conditioned suppression and punishment in the rat" (1985) Behav Neurosci 99, 60-74, Feb. 1985.
Irnich, "Paradigm shift in lead design" (1999) Pacing Clin Electrophysiol 22, 1321-1332, Sep. 1999.

(56) References Cited

OTHER PUBLICATIONS

Iyer, et al., "Priming stimulation enhances the depressant effect of low-frequency repetitive transcranial magnetic stimulation" (2003) J Neurosci 23, 10867-10872, Nov. 26, 2003.

John, et al., "An exploration of the functional relationship between electroencephalographic potentials and differential inhibition" (1961) Ann N Y Acad Sci 92, 1160-1182, Jul. 1961.

Kapural et al.; "Comparison of 10-kHz High-Frequency and Traditional Low-Frequency Spinal Cord Stimulation for the Treatment of Chronic Back and Leg Pain: 24-Month Results From a Multicenter, Randomized, Controlled Pivotal Trial"; Neurosurgery; 79(5); pp. 667-677; Nov. 2016.

Kapural et al.; "Novel 10-kHz High-frequency Therapy (HF10 Therapy) Is Superior to Traditional Low-frequency Spinal Cord Stimulation for the Treatment of Chronic Bank and Leg Pain"; Anesthesiology; 123; pp. 851-860; Oct. 2015.

Kasteleijn-Nolst, et al., "The impact of subclinical epileptiform discharges on complex tasks and cognition: relevance for aircrew and air traffic controllers" (2005) Epilepsy Behav 6, 31-34, Feb. 2005.

Katayama, et al., "Deep brain and motor cortex stimulation for post-stroke movement disorders and post-stroke pain" (2003) Acta Neurochir Suppl 87, 121-123 (Applicant points out, in accordance with MPEP 609.04(a), that the year of publication, 2003 is sufficiently earlier than the effective U.S. filing date, so that the particular month of publication is not in issue.).

Kilgore et al.; "Nerve Conduction Block Utilising High-Frequency Alternating Current"; Med. Biol. Eng. Comput.; 42; pp. 394-406; May 2004.

Kilgore et al.; "Reversible Nerve Conduction Block Using Kilohertz Frequency Alternating Current"; Neuromodulation; 17(3); pp. 242-255; Apr. 2014.

Kim et al., "Uniformity of Current Density Under Stimulating Electrodes, Critical Reviews in Biomedical Engineering", vol. 17, Issue 6 (1990), pp. 585-619. (Applicant points out, in accordance with MPEP 609.04(a), that the year of publication, 1990 is sufficiently earlier than the effective U.S. filing date, so that the particular month of publication is not in issue.).

Kinoshita, et al., "Electric stimulation on human cortex suppresses fast cortical activity and epileptic spikes" Jun. 28, 2004, Epilepsia 45, 787-791.

Kinoshita, et al., "Low-frequency repetitive transcranial magnetic stimulation for seizure suppression in patients with extratemporal lobe epilepsy—A pilot study" Sep. 2005, Seizure 14, 387-392.

Kossoff, et al., "Effect of an external responsive neurostimulator on seizures and electrographic discharges during subdural electrode monitoring" Dec. 2004, Epilepsia 45, 1560-1567.

Kovner, et al., "Disruption of short-term visual memory by electrical stimulation of inferotemporal cortex in the monkey" (1972) J Comp Physiol Psychol 81, 163-172 (Applicant points out, in accordance with MPEP 609.04(a), that the year of publication, 1972 is sufficiently earlier than the effective U.S. filing date, so that the particular month of publication is not in issue.).

Krnjevic, et al., "Stimulation-evoked changes in extracellular K+ and Ca2+ in pyramidal layers of the rat's hippocampus" Dec. 1982, Can J Physiol Pharmacol 60, 1643-1657.

Kumar et al., "The effects of spinal cord stimulation in neuropathic pain are sustained: a 24-month follow-up of the prospective randomized controlled multicenter trial of the effectiveness of spinal cord stimulation", Neurosurgery-online.com, vol. 63, No. 4, Oct. 2008, 9 pages.

Kuncel, et al., "Selection of stimulus parameters for deep brain stimulation" Nov. 2004, Clin Neurophysiol 115, 2431-2441.

Lambru et al.; "Safety and Efficacy of Cervical 10kHz Spinal Cord Stimulation in Chronic Refractory Primary Headaches: a Retrospective Case Series"; The Journal of Headache and Pain; 17:66; 8 pages; Jul. 8, 2016.

Lempka et al.; "Computational Analysis of Kilohertz Frequency Spinal Cord Stimulation for Chronic Pain Management"; Anesthesiology; 122(6); pp. 1362-1376; Jun. 2015.

Lertmanorat, et al., "A novel electrode array for diameter-dependent control of axonal excitability: a simulation study" Jun. 21, 2004, IEEE Trans Biomed Eng 51, 1242-1250.

Lertmanorat, et al., "Extracellular voltage profile for reversing the recruitment order of peripheral nerve stimulation: a simulation study" Nov. 17, 2004, J Neural Eng 1, 202-211.

Levy, Robert M.; "The Need for Mechanism-Based Medicine in Neuromodulation"; Neuromodulation; 15; pp. 273-279; Jul. 2012.

Li et al., "CaBP1, a neuronal Ca2+ sensor protein, inhibits inositol trisphosphate receptors by clamping intersubunit interactions," PNAS, May 21, 2013, 110(21):8507-8512.

Macmillan Dictionary (online); definition of "in place of"; 2 pages; accessed May 19, 2020; https://www.macmillandictionary.com/dictionary/british/in-place-of.

Manola, et al., "Modelling motor cortex stimulation for chronic pain control: electrical potential field, activating functions and responses of simple nerve fibre models" May 2005, Med Biol Eng Comput 43, 335-343.

Matsuda, et al., "Epileptogenesis induced by alternate-site kindling in bilateral hippocampi" Mar. 2003, Epilepsia 44, 292-298.

Mcintyre, et al., "Cellular effects of deep brain stimulation: model-based analysis of activation and inhibition" Apr. 1, 2004, J Neurophysiol 91, 1457-1469.

Mcintyre, et al., "Electric field and stimulating influence generated by deep brain stimulation of the subthalamic nucleus" Mar. 2004, Clin Neurophysiol 115, 589-595.

Mcintyre, et al., "Excitation of central nervous system neurons by nonuniform electric fields" Feb. 1999, Biophys J76, 878-888.

Mcintyre, et al., "Extracellular stimulation of central neurons: influence of stimulus waveform and frequency on neuronal output" Oct. 2002, J Neurophysiol 88, 1592-1604.

Mcintyre, et al., "Finite element analysis of the current-density and electric field generated by metal microelectrodes" Mar. 2001, Ann Biomed Eng 29, 227-235.

Mcintyre, et al., "Selective microstimulation of central nervous system neurons" Mar. 2000, Ann Biomed Eng 28, 219-233.

Menkes, et al., "Slow-frequency repetitive transcranial magnetic stimulation in a patient with focal cortical dysplasia" Epilepsia 41, 240-242, Aug. 2, 2005.

Mie, et al., Induction of neural differentiation by electrically stimulated gene expression of NeuroD2. Feb. 2003, J Biotechnol 100, 231-238.

Miklavcic, et al., "The effect of high frequency electric pulses on muscle contractions and antitumor efficiency in vivo for a potential use in clinical electrochemotherapy" Feb. 2005, Bioelectrochemistry 65, 121-128.

Miklavcic, et al., "The importance of electric field distribution for effective in vivo electroporation of tissues" vol. 74, Issue 5, May 1998, Biophys J 74, 2152-2158.

Misawa, et al., "Low-frequency transcranial magnetic stimulation for epilepsia partialis continua due to cortical dysplasia" vol. 234, Issues 1-2, Jul. 2005, J Neurol Sci 234, 37-39.

Miyoshi, et al., "Proposal of a new method for narrowing and moving the stimulated region of cochlear implants: animal experiment and numerical analysis" Apr. 1999, IEEE Trans Biomed Eng 46, 451-460.

Moro, et al., "The impact on Parkinson's disease of electrical parameter settings in STN stimulation" Sep. 2002, Neurology 59, 706-713.

Mutani, et al., "Effect of low frequency caudate stimulation on the EEG of epileptic neocortex" Aug. 1969, Brain Res 14, 749-753.

Nakagawa, et al., "Suppression of spontaneous epileptiform activity with applied currents". Dec. 1991, Brain Res 567, 241-247.

Nakamura, "Two types of inhibitory effects upon brain stem reticular neurons by low frequency stimulation of raphe nucleus in the rat" Feb. 1977, Brain Res 93, 140-144.

Nashold, Jr. et al.; "Dorsal Column Stimulation for Control of Pain"; J. Neurosurg.; 36; pp. 590-597; May 1972.

Neurosurgery Survival Guide—2016, http://neurosurgerysurvivalguide.com, 4 pages, downloaded on Jul. 15, 2020.

Nevro Fact Sheet; "HF10(TM) Therapy Fact Sheet"; Sep. 5, 2015 Rev A; https://sa1s3.patientpop.com/assets/docs/28990.pdf+&cd=1 &hl=en&ct=clnk&gl=us, 4 pages.

(56) References Cited

OTHER PUBLICATIONS

Oakley et al.; "A New Spinal Cord Stimulation System Effectively Relieves Chronic, Intractable Pain: A Multicenter Prospective Clinical Study"; Neuromodulation: Technology at the Neural Interface; 10(3); pp. 262-278; Jan. 2007.
Oakley, John C.; "Spinal Cord Stimulation in Axial Low Back Pain: Solving the Dilemma"; Pain Medicine; vol. 7; No. S58-S63; 2006, downloaded May 19, 2020.
Perruchoud et al.; "Analgesic Efficacy of High-Frequency Spinal Cord Stimulation: A Randomized Double-Blind Placebo-Controlled Study"; Neuromodulation; 16; pp. 363-369; Dec. 21, 2012.
Plonsey, et al., "Electric field stimulation of excitable tissue" (1995) IEEE Trans Biomed Eng 42, 329-336, Apr. 1995.
Plonsey, et al., "Electric field stimulation of excitable tissue" (1998) IEEE Eng Med Biol Mag 17, 130-137, Sep./Oct. 1998.
Puc et al., "Techniques of signal generation required for electropermeabilization. Survey of electropermeabilization devices" (2004) Bioelectrochemistry 64, 113-124, accepted Apr. 8, 2004.
Pucihar, et al., "The effect of pulse repetition frequency on the uptake into electropermeabilized cells in vitro with possible applications in electrochemotherapy" (2002) Bioelectrochemistry 57, 167-172, Jun. 4, 2002.
Pumir, et al., "Effect of an externally applied electric field on excitation propagation in the cardiac muscle" (1994) Chaos 4, 547-555, Jun. 4, 1998.
Rattay, et al., "Effective electrode configuration for selective stimulation with inner eye prostheses" (2004) IEEE Trans Biomed Eng 51, 1659-1664, Sep. 2004.
Reddy et al.; "Comparison of Conventional and Kilohertz Frequency Epidural Stimulation in Patients Undergoing Trialing for Spinal Cord Stimulation: Clinical Considerations"; World Neurosurg.; 88; pp. 586-591; Apr. 2016.
Robb et al.; "Transcutaneous Electrical Nerve Stimulation vs. Transcutaneous Spinal Electroanalgesia for Chronic Pain Associated with Breast Cancer"; Journal of Pain and Symptom Management; 33(4); pp. 410-419; vol. 33, No. 4, Apr. 2007.
Rossi, et al., "Reduction of cortical myoclonus-related epileptic activity following slow-frequency rTMS" (2004) Neuroreport 15, 293-296, Oct. 6, 2003.
Santos-Anderson, et al., "Stimulation of rat medial or sulcal prefrontal cortex during passive avoidance learning selectively influences retention performance" (1976) Brain Res 103, 243-259, accepted Jul. 21, 1975.
Satkauskas, et al., "Electrophoretic Component of Electric Pulses Determines the Efficacy of In Vivo DNA Electrotransfer" (2005) Human Gene Therapy 16:1194-1201, Oct. 2005.
Senza Omnia Stimulator for Chronic Pain, with Widest Frequency Range, FDA Approved ; Product Information from Medgadget; 5 pages; printed May 18, 2020; https://www.medadget.com/2019/11/senze-omnia-stimulator-for-chronic-pain-with-widest-frequency-range-fda-approved.html.
Sepulveda, et al., "Finite element analysis of current pathways with implanted electrodes" (1983) J Biomed Eng 5, 41-48, Jan. 1983.
Shetty et al.; "The Successful Treatment of Post-Implantation Iatrogenic Neuropathic Pain With Target-Field Stimulation Using Existing Stimulating System"; Ref 701; from Poster Sessions/European Journal of Pain Supplements; 5; p. 188; (2011) (Applicant points out, in accordance with MPEP 609.04(a), that the year of publication, 2011, is sufficiently earlier than the effective U.S. filing date, so that the particular month of publication is not in issue.).
Simpson, et al.; "A Randomized, Double-Blind, Crossover Study of the Use of Transcutaneous Spinal Electroanalgesia in Patients with Pain from Chronic Critical Limb Ischemia"; Journal of Pain and Symptom Management; 28(5); pp. 511-516; Nov. 2004.
Skelton, et al., "Low-frequency stimulation of the perforant path produces long-term potentiation in the dentate gyms of unanesthetized rats" (1983) Can J Physiol Pharmacol 61, 1156-1161.
St. Jude Medical, Product Information; "Eon Mini Rechargeable IPG"; 2 pages; 2008 https://pdf.medicalexpo.com/pdf/st-jude-medical/eon-mini-rechargeable-ipg/70886-94459.html (Applicant points out, in accordance with MPEP 609.04(a), that the year of publication, 2008, is sufficiently earlier than the effective U.S. filing date, so that the particular month of publication is not in issue.).
Struijk, et al., "Theoretical performance and clinical evaluation of transverse tripolar spinal cord stimulation" (1998) IEEE Trans Rehabil Eng 6, 277-285, Sep. 1998.
Struijk, et al., "Transverse tripolar spinal cord stimulation: theoretical performance of a dual channel system" (1996) Med Biol Eng Comput 34, 273-279, final form.
Susil, et al., "Separation between virtual sources modifies the response of cardiac tissue to field stimulation" (1999) J. Cardiovasc Electrophysiol 10, 715-727, published Feb. 1999.
Sweet et al.; "Paresthesia-Free High-Density Spinal Cord Stimulation for Postlaminectomy Syndrome in a Prescreened Population: A Prospective Case Series"; Neuromodulation; 19; pp. 260-267; (2016).
Tai, et al., "Simulation of nerve block by high-frequency sinusoidal electrical current based on the Hodgkin-Huxley model" IEEE Trans Neural Syst Rehabil Eng. Sep. 2005; 13(3):415-22.
Tan et al.; "Intensity Modulation: A Novel Approach to Percept Control in Spinal Cord Stimulation"; Neuromodulation; 19;pp. 254-259; (2016), accepted Sep. 1, 2015.
Tergau, et al., "Low-frequency repetitive transcranial magnetic stimulation improves intractable epilepsy" (1999) Lancet 353, 2209, Jun. 26, 1999.
Thompson et al.; "A Double Blind Randomised Controlled Clinical Trial on the Effect of Transcutaneous Spinal Electroanalgesia (TSE) on Low Back Pain"; European Journal of Pain; 12; pp. 371-377; (2008), available online Sep. 7, 2007.
Tiede et al.; "Novel Spinal Cord Stimulation Parameters in Patients with Predominant Back Pain"; Neuromodulation; 16; pp. 370-375; accepted Jan. 3, 2013.
Ueno, et La., "Localized stimulation of neural tissues in the brain by means of paried configuration of time-varying magnetic fields" (1988) Journal of Applied Phys. 64, 5862-5864, Nov. 15, 1988.
Van Buyten; "High-Frequency Spinal Cord Stimulation for the Treatment of Chronic Back Pain Patients: Results of a Prospective Multicenter European Clinical Study"; Neuromodulation; 16; pp. 59-66; Oct. 13, 2013.
Velisek, et al., "Low-frequency stimulation of the kindling focus delays basolateral amygdala kindling in immature rats" (2002) Neurosci Lett 326, 61-63, Feb. 18, 2002.
Velisek, et al., "Lowering of extracellular pH suppresses low-Mg(2+)—induces seizures in combined entorhinal cortex-hippocampal slices" (1994) Exp Brain Res 101, 44-52, May 9, 1994.
Weiss, et al., "Quenching: inhibition of development and expression of amygdala kindled seizures with low frequency stimulation" (1995) Neuroreport 6, 2171-2176, Nov. 1995.
Wieraszko, "Amplification of evoked potentials recorded from mouse hippocampal slices by very low repetition rate pulsed magnetic fields" (2004) Bioelectromagnetics 25, 537-544, final form accepted Apr. 20, 2004.
Windels, et al., "Influence of the frequency parameter on extracellular glutamate and gamma-aminobutyric acid in substantia nigra and globus pallidus during electrical stimulation of subthalamic nucleus in rats" (2003) J Neurosci Res 72, 259-267, Dec. 17, 2002.
Yamamoto, et al., "New method of deep brain stimulation therapy with two electrodes implanted in parallel and side by side" (2001) J Neurosurg 95, 1075-1078, Dec. 2001.
Yearwood, et al.: A prospective comparison of Spinal cord stimulation (SCS) Using Dorsal Column Stimulation (DCS), Intraspinal Nerve Root Stimulation (INRS), and varying pulse Width in the Treatment of Chronic Low Back Pain Digital Abstract presented at CNS 56th Annual Meeting, Chicago 2006, Jul. 10, 2006, 7 pgs.
Prosecution History from U.S. Appl. No. 15/075,582, dated Oct. 4, 2018 through Aug. 1, 2019, 52 pp.
U.S. Appl. No. 16/901,206, filed Jun. 15, 2020, naming inventor Michael John, Sasha.
U.S. Appl. No. 17/007,563, filed Aug. 31, 2020, naming inventor Michael John, Sasha.
U.S. Appl. No. 17/007,570, filed Aug. 31, 2020, naming inventor Michael John, Sasha.
U.S. Appl. No. 17/106,589, filed Nov. 30, 2020, naming inventors Vellejo et al.

(56) References Cited

OTHER PUBLICATIONS

De Leo et al., "The tetrapartite synapse: Path to CNS sensitization and chronic pain," Pain, ElSevier, Feb. 21, 2006, 5 pp.
Gravius et al., Selective L4 Dorsal Root Ganglion Stimulation Evokes Pain Relief and Changes of Inflammatory Markers: Part I Profiling of Saliva and Serum Molecular Patterns, Neuromodulation: Technology at the Neural Interface, Aug. 15, 2018, 9 pp.
Guthrie et al., "ATP Released from Astrocytes Mediates Glial Calcium Waves," The Journal of Neuroscience, Jan. 15, 1999, 19(2):520-528, Jan. 15, 1999.
Jang et al., "High frequency electrical stimulation promotes expression of extracellular matrix proteins from human astrocytes," Jul. 2, 2019, 7 pp.
Kinfe et al., "Burst Spinal Cord Stimulation Increases Peripheral Antineuroinflammatory Interleukin 10 Levels in Failed Back Surgery Syndrome Patients With Predominant Back Pain," Jan. 3, 2017, 9 pp.
Li et al., "An update on reactive astrocytes in chronic Pain," Journal of Neuroinflammation, Jul. 9, 2019, 13 pp.
Milligan et al., "Pathological and protective roles of glia in chronic pain," vol. 10, Nature Reviews, Jan. 2009, 15 pp.
Chakravarthy et al., "Mechanism of Action in Burst Spinal Cord Stimulation: Review and Recent Advances," Pain Medicine, downloaded on Dec. 16, 2019, 13 pp.
Porter et al, "Hippocampal Astrocytes In Situ Respond to Glutamate Released from Synaptic Terminals," The Journal of Neuroscience, Aug. 15, 1996, 9 pp.
Roitbak et al., "Depolarization of cortical glial cells in Response to Electrical stimulation of the Cortical Surface," Neuroscience, vol. 6, No. 12, 1981, 9 pp. (Applicant points out, in accordance with MPEP 609.04(a), that the year of publication, 1981 is sufficiently earlier than the effective U.S. filing date, so that the particular month of publication is not in issue.).
Scholz et al., "The neuropathic pain triad: neurons, immune cells and glia," Nature Neuroscience, vol. 10, No. 11, Nov. 2007, 8 pp.
Sato et al., "Spinal cord stimulation reduces mechanical hyperalgesia and glial cell activation in animals with neuropathic pain," PMC Public Access, Feb. 1, 2015, 20 pp.
Stephens et al., "RNA-seq of spinal cord from nerve-injured rats after spinal cord stimulation," Molecular Pain, Nov. 12, 2018, 13 pp.
Tawfik et al., "Deep Brain Stimulation Results in Local Glutamate and Adenosine Release: Investigation into the Role of Astrocytes," Neurosurgery, Aug. 2010, 17 pp.
Johanek et al., "The effects of modulating stimulation parameters of spinal cord stimulation (SCS) and glial activity in animals with neuropathic pain," Journal of Pain, Apr. 2011, 10 pp.
Tilley et al., "Spinal Cord Stimulation Modulates Gene Expression in the Spinal Cord of an Animal Model of Peripheral Nerve Injury," Regional Anesthesia and Pain Medicine, vol. 41, Nov. 6, Nov.-Dec. 2016, 7 pp.
Vallejo et al., The Role of Glia and the Immune System in the Development and Maintenance of Neuropathic Pain, Review Article, Pain Practice, vol. 10, Issue 3, accepted Jan. 2010, 18 pp.
Vallejo et al., "Genomics of the Effect of Spinal Cord Stimulation on an Animal Model of Neuropathic Pain," Neuromodulation: Technology at the Neural Interface, Wiley OnlineLibrary, May 11, 2016, 11 pp.
Vallejo et al., "Effects of Phase Polarity and Charge Balance Spinal Cord Stimulation on Behavior and Gene Expression in a Rat Model of Neuropathic Pain," Neuromodulation: Technology at the Neural Interface, Wiley OnlineLibrary, accepted Apr. 3, 2019, 10 pp.
Vedam-Mai et al., "Deep brain stimulation and the role of astrocytes," Molecular Psychiatry (2012) 17, 124-131, published online May 31, 2011, 8 pp.
U.S. Appl. No. 16/901,202, filed Jun. 15, 2020, naming inventor Michael John, Sasha.

\* cited by examiner

METHOD AND APPARATUS FOR MULTI MODAL OR MULTIPLEXED ELECTRICAL MODULATION OF PAIN USING COMPOSITE ELECTROMAGNETIC FIELDS

CROSS-REFERENCE TO RELATED APPLICATIONS

This application claims priority to, and benefit of, U.S. Provisional Application No. 62/843,757, filed May 6, 2019, and entitled "Method and Apparatus for Modulation of Cell Activity in Neural Tissue Using Multiplexed Electrical Signals on Differential Targets", the entire contents of which are specifically incorporated herein by reference.

This application also claims priority to, and benefit of, U.S. Provisional Application No. 62/964,281, filed Jan. 22, 2020, and entitled "Method and Apparatus for Multimodal Electrical Modulation of Pain Using Composite Electromagnetic Fields", the entire contents of which are specifically incorporated herein by reference.

FIELD

This disclosure relates to systems and methods for providing multimodal or multiplexed stimulation of neural structures, and, more specifically, for managing pain with an electromagnetic signal having multiple components of characteristic parameters.

OVERVIEW

The term Spinal Cord Stimulation (SCS) is used to describe an advanced management therapy for chronic pain in which a varying electric field is applied to the Dorsal section of the spinal Cord (DC) via an electrode array (or electrode arrays) implanted in the epidural space. Conventional SCS also called tonic, traditionally utilizes an electric field varying between 40-250 Hz that is directed to a targeted pain location by overlaying it with a perceived tingling sensation, known as paresthesia, created by the stimulating electric field. This therapy has been clinically utilized for about half a century. The principal mode of action is based on the Gate Control Theory formulated by Melzack and Wall, although a full understanding of the mechanism has yet to be elucidated. The concept behind tonic SCS is that the paresthesia induced by the applied varying electric field masks, or "closes the gates to", pain signals travelling to the brain, however, the relationship between frequency, waveform shape, amplitude and pulse width and the mechanism by which SCS provides an analgesic effect is not fully understood.

SUMMARY

Disclosed herein are apparatus and methods for managing pain in a patient by using multimodal stimulation of neural structures, with an electromagnetic signal having multiple components of characteristic frequencies, amplitudes, and phase polarities. Multimodal modulation for pain management, in accordance with the disclosure, contemplates the use of oscillating electromagnetic fields which is applied via an array of electrodes (referred as contacts or leads) to a particular neural structure using temporal and amplitude characteristics, to modulate glial and neuronal interactions as the mechanism for relieving chronic pain. More specifically, exemplary aspects provide an apparatus and method for modulating the expression of genes involved in diverse pathways including inflammatory/immune system mediators, ion channels and neurotransmitters, in both the Spinal Cord (SC) and Dorsal Root Ganglion (DRG). In one exemplary embodiment, such expression modulation is caused by spinal cord stimulation or peripheral nerve stimulation. In one embodiment, the amplitudes and frequencies of the signal or signals used to create the multimodal stimulation of neural structures may be optimized for pain relief and low power usage in an implantable multimodal signal generator, as described herein.

According to one exemplary embodiment, apparatuses and methods provide for managing pain in a patient by using multiplexed stimulation signals to target different neural structures such that the multiple stimulation signals are multiplexed in the time domain, hereafter referred to as "differential target multiplexed stimulation." For instance, a signal generator can multiplex signals that can have different signal characteristics (e.g., pulse frequency, amplitude, or pulse duration) to generate differential target multiplexed stimulation for pain management. In accordance with aspects of the disclosure, the output of the signal generator can be used to produce separate oscillating electromagnetic fields (stimulation signals) which can be applied to different set of a plurality of electrodes (also referred as contacts). The electrodes can be part of a lead that is designed to apply the respective stimulation signals to different parts of a particular neural structure.

Various aspects of the disclosure relate to the use of a variety of temporal and amplitude characteristics in order to modulate glial and neuronal interactions as the mechanism for relieving chronic pain. The multiplexed stimulation signals have characteristics that allow for a synergistic targeting of glial cells and neurons in a differential manner. For instance, disclosed are embodiments relating to an apparatus and method for modulating the expression of genes and proteins involved in diverse pathways, including inflammatory/immune system mediators, ion channels and neurotransmitters, associated with the interaction of glia and neurons in neural tissue. In embodiments, such expression modulation may be caused by any of spinal cord stimulation, dorsal root ganglion stimulation, brain stimulation, or peripheral nerve stimulation. In embodiments, the amplitudes, phase polarity, waveforms, and frequencies of the signals combined to create the differential target multiplexed stimulation of neural structures may be optimized for pain relief and low power usage in an implantable signal generator, as described herein.

In embodiments of differential target multiplexed stimulation therapy, a set of high frequency charge-balanced biphasic pulsed signals in which the polarity of the first phase of the high frequency signals may be either cathodic or anodic is utilized. In embodiments, a set of low frequency signals is used that may have waveform characteristics different from those of the high frequency signals. The polarity of the first phase of the biphasic charge-balanced low frequency signals may be either cathodic or anodic. The high and low frequency stimulation signals can be delivered to the neural tissues by multiplexing individual pulses from each via respective sets of electrodes. In certain embodiments, the respective sets of electrodes can be co-located in close proximity to the same neural tissue (e.g., near the same vertebrae).

According to one aspect of the present disclosure, a method for managing pain in a subject comprises modulation of the activity of glial cells in the stimulated neural tissue by regulating any of genes and proteins for calcium binding, cytokines, cell adhesion or specific immune response. In one embodiment, modulating the activity of the glial cells comprises exposing the glial cells to a stimulus comprising multiple signal components. The method also comprises the simultaneous modulation of neuronal genes and proteins related to regulation of neuronal activity, such as ion channels, neurotransmitter release, or intracellular calcium regulation. In embodiments, modulating the activity of the neurons comprises exposing the neurons to a stimulus comprising multiple signal components. Without being bound by theory, he targeted modulation of the different types of target cells (glial cells and neurons) is believed to help normalize neuroglia interactions that have been affected by the development of a chronic pain state as a result of sensitization of the nervous system.

According to aspects of the present disclosure, a method for managing pain of a subject by providing differential target multiplexed stimulation to various neural tissue locations using multiple electrodes within one or more electrode arrays, which are located in relevant anatomical locations within the central or peripheral nervous system, which are suitable for pain in various body locations. In embodiments, the electrode arrays are positioned intraspinally within the epidural space in order to access different aspects of the spinal cord, or the foramens where dorsal root ganglia are located or the lateral space above and below the conus medularis in order to stimulate the dorsal nerve roots. Stimulation of the neural tissue in these anatomical locations with differential target multiplexed signals may provide relief from chronic pain in the neck, upper limbs, trunk, low back, and lower limbs associated with various pathological conditions. In another embodiment, the electrode arrays may be positioned proximal to injured peripheral nerves in different anatomical locations. The electrode arrays may also be placed in motor cortex or deep brain structures to deliver differential target multiplexed stimulation and provide relief for various pathological conditions.

According to another aspect of the disclosure, a differential target multiplexed stimulation system comprises: memory for storing a plurality of signal parameter programs; a selection device for selecting one of the plurality of signal parameter programs, a signal generator controllable by a selected of the plurality of signal parameter programs; and an output unit for connection to at least one electrode array; wherein the stimulation system is configured to provide multiple electric signals having at least one glial stimulating signal and at least one neuronal stimulating signal at least one electrode array via the output unit. Each of the glial stimulating signals and neuronal stimulating signals may be the result of combining multiple pulsed electrical signals, with different parameters. Such parameters may include any of pulse frequency, pulse width, pulse amplitude, mode of active or passive charge balance, duty cycle, etc. In embodiments, the system further comprises an enclosure of biocompatible material surrounding the differential target multiplexed signal generator and output unit. In another embodiment, the selection device is configured for receiving user definable instructions for modifying any of the respective electrical parameters of the multiple signals that constitute the differential target multiplexed stimulation signals.

According to yet another aspect of the present disclosure, a method for managing pain in a subject comprises using one or more electrical signals to modulate the activation of neurons in the stimulated neural tissue. Modulation of the neurons can include lowering the threshold for depolarization of neurons, and activation or deactivation of neurotransmission in the neural tissue of the subject with a differential target multiplexed signal. Simultaneously, the method can include the use of one or more electrical signals that modulate the activation of glial cells in the stimulated neural tissue. Modulation of the glial cells can include lowering the activation of microglia, oligodendrocytes, and astrocytes, increasing neuroprotective effects of the glia, regulation of neurotransmitters associated with glia activation, and regulation of cellular communication processes, which are controlled by the glial cells. In embodiments, the characteristics of the electric signals provided by the differential target multiplexed stimulation of neurons and glial cells in the neural tissue of the subject have any of different respective pulse frequencies, pulse amplitudes, pulse widths, mode of charge balance, duty cycles, interphase delays, and phase polarities. In another embodiment, each of the multiplexed signals that differentially target neurons and glial cells of the neural tissue field may be provided by either a single electric pulsed signal or by the combination of two or more different electric pulsed signals.

According to another aspect of the present disclosure, a method for managing pain in a subject comprises the modulation of the activity of neurons by lowering the threshold for depolarization of neurons and activation or deactivation of neurotransmission in the neural tissue of the subject with a differential target multiplexed signal; and the modulation of the activity of glial cells by lowering the activation of microglia, oligodendrocytes, and astrocytes, increasing the neuroprotective effects of the glial cells, regulating neurotransmitters associated with glia activation, and regulating cellular communication processes controlled by the glial cells. Modulation of the neuronal activity and the glial cell activity is achieved using pulsed electrical signals with distinctive characteristics, such as frequency, amplitude, pulse width, mode of charge balance, phase polarity, duty cycle, and interphase delays, and which may be delivered simultaneously or in two different time periods not identical to each other; wherein these differential target multiplexed stimulation signals change synaptic plasticity of neurons and glial cells within the neural structures and reestablish the required balance of neuroglial interactions present in a non-chronic pain state.

According to another aspect, the present disclosure provides a method for managing pain in a subject comprises the modulation of the activity of neurons by lowering the threshold for depolarization of neurons and activation or deactivation of neurotransmission in the neural tissue of the subject with a differential target multiplexed signal; and the modulation of the activity of glial cells by lowering the activation of microglia, oligodendrocytes, and astrocytes, increasing the neuroprotective effects of the glial cells, regulating neurotransmitters associated with glia activation, and regulating cellular communication processes controlled by the glial cells; wherein the manipulation of the respective characteristics of the multiplexed signal changes the synaptic plasticity of neurons and glial cells within the neural tissue of the subject.

Also disclosed herein is an apparatus comprising a multiplexed signal generation module that is configured for electrically coupling with one or more electrode arrays to differentially target neurons and glial cells in neural tissue.

Optionally, the differential target multiplexed signal generation module is arranged for generating multiple electric signals, which can be combined into multiplexed signals that can be delivered to one or more electrode arrays.

Optionally, the differential target multiplexed signal generation module comprises various electric signal sources or terminals in which one or more electrode arrays comprising of at least a first and a second subgroup of electrodes. In one embodiment, the first subgroup of electrodes can be electrically coupled to a first electric signal source and/or terminal and the second subgroup of electrodes can be electrically coupled to the second electric signal source and/or terminal. Multiple subgroup of electrodes can be electrically coupled with multiple electrical signal sources and/or terminals.

Optionally, the differential target multiplexed signal generation module is configured for having an operating mode for providing pulsed electric signals corresponding to the glial and neuronal stimulation signals as described herein. Optionally, such pulsed electric signals are charge balanced and may have different characteristic parameters such as pulse frequency, pulse amplitude, pulse width, leading phase polarity, mode of charge balance, interphase delay and duty cycle.

Optionally, the differential target multiplexed signal generation module is configured for having an operating mode for providing electric signals to the subgroups of electrodes in the electrode arrays corresponding to the stimulus of any of the methods described herein.

Optionally, the differential target multiplexed signal generation module can be configured for having an operating mode for providing pulsed electric signals between 20 Hz and 1,500 Hz. The frequency of the electrical signals that target glial cells can be different from the frequency of the electrical signals that target neurons. Other characteristics, such as the pulse width, mode of charge balance (active or passive), interphase delay, and/or amplitude, of these electric signals may be different. The glial and neuronal stimulation signals can be multiplexed in a manner that results in the stimulation to be delivered at the same time without requiring the pulses overlap between the respective signals.

As used herein, a differential target multiplexed signal generation module that is configured for having an operating mode may comprise a memory module containing instructions defining at least an operating mode as described, wherein the operating mode is optionally a user-selectable operating mode and the memory module optionally comprises instructions for additional operating modes. In certain embodiments the differential target multiplexed signal generation module is configured for delivering electrical signals to one or more subgroup of electrodes within one or more electrode arrays as specified.

Optionally, the differential target multiplexed signal generation module comprises two or more electric signal sources, such as signal generators, that are independently controllable, and are configured for delivering electric signals with parameters that can be set separately for each of the electric signal sources.

Optionally, the apparatus is a non-implantable, e.g. trialing system, comprising a signal generation module comprising at least one signal generator configured for delivering multiple electric signals with parameters that can be set separately for each of the signals.

Optionally, an implantable differential target multiplexed signal generator module is adapted for electrically coupling with one or more electrode arrays, or optionally is coupled with one or more electrode arrays. The implantable differential target multiplexed generator module comprises generator circuitry and a housing. The housing hermetically seals the generator circuitry and can be made of a durable biocompatible material. The differential target multiplexed signal generator module has an output interface for establishing electrical connection with electrodes implemented in one or more electrode arrays, e.g. two or more terminals for electrically coupling to a two or more subgroup of electrodes implemented on one or more electrode arrays.

Optionally the implantable differential target multiplexed signal generator module comprises two or more signal generators and timer electronic circuitry that can slave one of the signal generators to another signal generator, such that a delay can be produced between signals generated from the at least two signal generators.

According to another aspect of the disclosure, a differential target multiplexed stimulation device comprises an output unit for connection to at least one electrode array, and at least one signal generator, wherein the stimulation device is arranged for providing a differential target multiplexed stimulation signal to the at least one electrode array via the output unit. At least one electrode within the electrode array is configured for exposing neural tissue and its constituent glial cells and neurons to the differential target multiplexed stimulation signals. The differential target multiplexed stimulation device can be a pain treatment device.

Optionally, the differential target multiplexed stimulation device is arranged for generating differential target multiplexed electric signals that can be provided to at least one particular electrode array called a stimulation lead.

Optionally, the differential target multiplexed stimulation device may have an output unit that includes a first output for connection to a first stimulation lead and a second output for connection to a second stimulation lead. The first stimulation lead includes a first array of electrodes. The second stimulation lead includes a second array of electrodes.

Optionally, the differential target multiplexed stimulation device is arranged for providing at least a first multiplexed electric signal to the first output and at least a second multiplexed electric signal to at least a second output. The first multiplexed electric signals and the other multiplexed electric signals can differ in one or more parameters such as amplitude, frequency, phase polarity, waveform shape, width, duty cycle and interphase delay. In some embodiments, some of the multiplexed electric signals can have the same set of parameters, while one or more of the other multiplexed electrical signals have at least one different parameter.

According to another aspect of the disclosure, a method for operating a differential target multiplexed signal generation module includes connecting the signal generation module to one or more stimulation leads that have been provided to a body of a subject. The method includes generating, using the differential target multiplexed signal generation module, a first multiplexed signal at least one of the one or more stimulation leads and generating, using the differential target multiplexed signal generation module, a second multiplexed signal at least one of the one or more stimulation leads. The first multiplexed signals and at least one of the other multiplexed signals can have at least one uncommon parameter therebetween.

According to another aspect of the disclosure, an electrically conducting material is provided, such as a metal or conductive polymer, e.g. in the form of an electrode, for use in administering the differential target multiplexed stimulation signals into a subject for the treatment of pain. The differential target multiplexed stimulation signals may have at least one uncommon parameter therebetween.

Optionally, a first multiplexed stimulation signal is a glial stimulation signal and a second multiplexed stimulation signal is a neuronal stimulation signal. The first multiplexed stimulation signal can be one electric signal or a combination of two or more electric signals with frequency between 100 Hz to 100 kHz. The second multiplexed stimulation signal can be one electric signal or a combination of two or more electric signals with a frequency lower than the first multiplexed stimulation signal, such as between 20 Hz and 500 Hz. The ratio of the frequencies between the first and second multiplexed stimulation signals be in the range of 5:1 to 5,000:1.

According to another aspect of the disclosure, a differential target multiplexed stimulation system comprises a memory for storing a plurality of differential target multiplexed signal parameter programs; a selection device for selecting one of the plurality of differential target multiplexed signal parameter programs; a differential target multiplexed signal generator device controllable by a selection of the plurality of differential target multiplexed signal parameter programs; and an output unit for connection to at least one stimulation lead comprised of an array of electrodes; wherein the stimulation device is configured to provide differential target multiplexed stimulation signals generated by the differential target multiplexed signal generator in accordance with a selection of the differential target multiplexed signal parameter programs to the at least one stimulation lead via the output unit. The differential target multiplexed stimulation system may further comprise an enclosure of biocompatible material surrounding the differential target multiplexed stimulation signal generator device and output unit. In one embodiment, the differential target multiplexed stimulation signal generator device generates two or more multiplexed electric signals in an operational mode thereof. In one embodiment, the differential target multiplexed stimulation system may be combined with at least one stimulation lead comprising of subgroups of electrodes, and wherein the subgroup of electrodes is electrically coupled to the two or more multiplexed stimulation signals.

According to another aspect of the disclosure, optimization of the differential target multiplexed stimulation therapy comprises the methodical selection of differential target multiplexed stimulation signals and corresponding characteristic parameters that fits the needs of the subject treated. This may include a combination of components in a manner described herein. In one embodiment, differential target multiplexed stimulation may also be optimized by setting the most appropriate electric fields that modulates the neuroglial interactions in the stimulated neural structures by selecting monopolar, bipolar, tripolar, guarded cathode, guarded anode, or any other multipolar arrangements in the one or more stimulation leads which have been positioned intraspinally in the neighborhood of the dorsal columns of the spinal cord, contiguous to any other aspect of the spinal cord, in the intervertebral foramens, or adjacent to the dorsal nerve roots corresponding to a particular anatomical region of the body in which the patient experiences pain, or in intracranial structures targeted to provide relief for various pathological conditions. In another embodiment, differential target multiplexed stimulation may also be optimized by setting the most appropriate electric fields that modulates the neuroglial interactions in the stimulated neural structures by selecting monopolar, bipolar, tripolar, guarded cathode, guarded anode, or any other multipolar arrangements in the one or more stimulation leads which have been positioned in the neighborhood of one or more peripheral nerves associated with a particular anatomical region of the body in which the patient experiences pain.

According to a further exemplary aspect, the present disclosure provides an electromagnetic stimulation system comprising: memory for storing a plurality of multimodal signal parameter programs; a selection device for selecting one of the plurality of multimodal signal parameter programs, a signal generator controllable by a selected of the plurality of multimodal signal parameter programs; and an output unit for connection to at least one electrode; wherein the stimulation system is configured to provide a composite electric signal having a priming phase signal segment and a tonic phase signal segment to the at least one electrode via the output unit. In one embodiment, the system further comprises an enclosure of biocompatible material surrounding the multimodal signal generator and output unit. In another embodiment, the selection device is configured for receiving user definable instructions for modifying any of the respective amplitudes, relative phases, waveform shapes, and widths of the priming phase signal segment and the tonic phase signal segment of the composite electric signal. In another embodiment, the selection device is configured for receiving user definable instructions for modifying any of the amplitudes and frequency of the composite electric signal.

According to yet another exemplary aspect, the present disclosure provides a method for managing pain in a subject comprising: A) lowering a threshold for depolarization of nerve fibers in the subject with a component of a composite electromagnetic field; and B) simultaneously activating glial cells with a second component of the composite electromagnetic field; without the administration of a pharmacological compound to the subject. In one embodiment, the components of the composite electromagnetic field have any of different respective frequencies, amplitudes, phases or harmonic content. In another embodiment, the composite electromagnetic field may be provided either by a single electromagnetic signal or by the combination of two or more different electromagnetic signals.

According to still another exemplary aspect, a method for managing pain in a subject comprises: A) lowering a threshold for depolarization of nerve fibers in the subject with a first component of a composite electromagnetic field for a first period of time; and B) simultaneously modulating glial cell activity with a second component of a composite electromagnetic field during a second period of time not identical to the first period of time; wherein the composite electromagnetic field change synaptic plasticity of neurons and glial cells within the neural structures.

According to another exemplary aspect, the present disclosure provides a method for managing pain in a subject comprising: A) lowering a threshold for depolarization of nerve fibers in the subject with a first phase segment of a biphasic signal; and B) modulating glial cell activity in the subject with a second phase segment of the biphasic signal; wherein manipulation of the biphasic signal changes synaptic plasticity of neurons and glial cells within the nerve fibers.

According to still another exemplary aspect, the present disclosure provides a method for managing pain in a subject comprising: A) activating glial cells by multimodal electromagnetic stimulation regulating any of genes for calcium binding proteins, cytokines, cell adhesion or specific immune response proteins; and B) administering a pharmacological substance to the subject systemically, epidurally, or intrathecally during a time period. In one embodiment, such a pharmacological substance may be injected through the stimulation lead, which may have a port to deliver the pharmacological agent directly into the epidural or intrathecal space. Optionally, the pharmacological agent may be impregnated onto the stimulation lead using a slow release formulation in order to provide a slow elution of the pharmacological substance into the neural tissue around the lead.

According to yet another exemplary aspect, the present disclosure provides a method for managing pain in a subject comprising: A) lowering a threshold for depolarization of nerve fibers in the subject with a component of the composite electromagnetic field; and B) simultaneously modulating glial cell activity with other components of the composite electromagnetic field; wherein the components of the composite electromagnetic field control the balance of glutamate and glutamine in a calcium dependent manner within the modulated glial cells. In one embodiment, the components of the composite electromagnetic field have any of different respective frequencies, amplitudes, phases, harmonic content, or width for rectangular waveforms. In another embodiment, the components of the composite electromagnetic fields may be provided either by a single electrical signal or by more than one different electrical signals.

According to still another exemplary aspect, a method for managing pain in a subject comprises: A) modulating glial cells with an asymmetric biphasic electromagnetic signal having variable duration of the anodic phase thereof selected to modulate the amount of glutamate released therefrom; and B) modulating glial cells with an asymmetric biphasic electromagnetic signal having variable duration of the cathodic phase thereof selected to modulate the amount of glutamate released therefrom.

According to yet another aspect, a method for managing pain in a subject comprises: A) modulating glial cells with an asymmetric biphasic electromagnetic signal having variable duration of the cathodic and anodic phases thereof selected to modulate the amount of glutamate released therefrom, wherein the electromagnetic fields control the balance of glutamate and glutamine in a calcium dependent manner within the modulated glial cells.

Also disclosed herein is an apparatus comprising a signal generation module that is configured for electrically coupling with one or more leads.

Optionally, the signal generation module is arranged for generating a composite electric signal. The composite electric signal can be a summed signal of multiple electric signals. Optionally, the signal generation module is arranged for generating a multimodal signal, such as a frequency-modulated signal. The composite signal and/or the multimodal signal can be provided to the one or more leads.

Optionally, the signal generation module comprises at least a first and a second electric signal source or terminal and the one or more leads comprise at least a first and a second subgroup of electrodes. The first subgroup of electrodes can be electrically coupled to the first electric signal source and/or terminal and the second subgroup of electrodes can be electrically coupled to the second electric signal source and/or terminal.

Optionally, the signal generation module is configured for having an operating mode for providing at least first and second electric signals corresponding to the first and second electromagnetic stimulus as described herein. Optionally, the first and second electric signals have a different frequency, amplitude and phase polarity characteristics.

Optionally, the signal generation module is configured for having an operating mode for providing electric signals to the electrodes corresponding to the electromagnetic stimulus of any of the methods described herein.

Optionally, the signal generation module can be configured for having an operating mode for providing a first electric signal having a frequency to the first subgroup of electrodes, and a at least a second electric signal having the same frequency to the second subgroup of electrodes. The frequency can be between 500 Hz and 1,500 Hz. Other parameters of the first and second electric signals may be different, such as the pulse width and/or amplitude. The first electric signal can be fired synchronously, i.e., simultaneously, with the second electric field, or asynchronously, e.g., with a given time delay, relative to the first electric signal.

As used herein, a signal generation module that is configured for having an operating mode may comprise a memory module containing instructions defining at least an operating mode as described, wherein the operating mode is optionally a user-selectable operating mode and the memory module optionally comprises instructions for additional operating modes. In certain embodiments the signal generation module is configured for delivering electrical signals to one or more leads as specified.

Optionally, the apparatus is a non-implantable, e.g., trialing, system, comprising a signal generation module comprising at least two signal generators configured for delivering electric signals with parameters that can be set separately for each of the signal generators, for example a Priming signal and a Tonic signal.

Optionally, an implantable multimodal generator is provided that is adapted for electrically coupling with one or more leads, or optionally is coupled with one or more leads. The implantable multimodal generator comprises generator circuitry and a housing. The housing can hermetically seal the generator circuitry and can be made of a durable biocompatible material. The generator has an output interface for establishing electrical connection with electrodes implemented in one or more leads, e.g., at least a first and second terminal for electrically coupling to a first and second subgroup of electrodes implemented on one or more leads.

According to another exemplary aspect of the disclosure, an electromagnetic stimulation device is provided including an output unit for connection to at least one electrode, and a signal generator, wherein the stimulation device is arranged for providing a multimodal stimulation signal to the at least one electrode via the output unit. The multimodal stimulation signal can be an electromagnetic signal. At least one electrode is configured for exposing glial cells and neurons to the multimodal stimulation signal. At least one lead can include an array of electrodes, or a plurality of arrays of electrodes.

Optionally, the signal generator is arranged for generating a multimodal electric signal, such as a frequency modulated signal or an amplitude modulated signal. The multimodal electric signal can be provided to at least one lead.

Optionally, the signal generator is arranged for providing a first electric signal to the first output and at least a second electric signal to at least a second output. The first electric signal and the other electric signals can differ in a parameter such as amplitude, frequency, phase, phase polarity, waveform shape, and width. The first electric signal and the other electric signals may correspond in a parameter such as amplitude, frequency, phase, phase polarity, waveform shape, and width. At least a second electric signal can be a tonic stimulation signal, and the first electric signal can have a frequency higher than the frequency of the tonic stimulation signal.

According to another exemplary aspect of the disclosure, a method for operating a signal generation module is provided. The method includes connecting the signal generation module to one or more leads. The leads can already have been provided to a body of a subject. The method includes generating, using the signal generation module, a first oscillating electromagnetic field at least one of the one or more leads and generating, using the signal generation module, a second oscillating electromagnetic field at least one of the one or more leads. The first oscillating electromagnetic field and at least one of the other oscillating electromagnetic fields can have at least one uncommon parameter there between.

Optionally, the first component of the composite signal is a Priming signal and a second component is a Tonic signal. The first component can have a frequency between 200 Hz to 100 kHz. The second component can have a frequency lower than the first stimulus, such as between 10 Hz and 500 Hz. In an exemplary embodiment, the frequency of the first stimulus and the frequency of the second stimulus has a ratio in the range of 2:1 to 40:1, 4:1 to 40:1, 10:1 to 40:1, 20:1 to 40:1, up to 70:1, up to 140:1, etc.

According to another exemplary aspect of the disclosure, an electromagnetic stimulation system comprises a memory for storing a plurality of multimodal signal parameter programs; a selection device for selecting one of the plurality of multimodal signal parameter programs; a multimodal signal generator controllable by a selected of the plurality of multimodal signal parameter programs; and an output unit for connection to at least one electrode; wherein the stimulation device is configured to provide a multimodal stimulation signal generated by the multimodal signal generator in accordance with a selected of the multimodal signal parameter programs to the at least one electrode via the output unit.

According to another exemplary aspect of the disclosure, optimization of the therapy comprises the methodical selection of multimodal stimulation waveforms and parameters that fits the needs of the patient treated. This may include a combination of components in a manner described herein.

According to another exemplary aspect of the disclosure, a method of managing pain in a subject comprises: lowering a threshold for depolarization of nerve fibers in the subject with a first phase segment of a biphasic signal; and modulating glial cell activity in the subject with a second phase segment of the biphasic signal.

In exemplary embodiments, a first phase segment of the biphasic signal is derived from a first electric signal having a current amplitude set to a value corresponding to a percentage of a Priming Perception Threshold (PPT) of the subject, and the second phase segment of the biphasic signal is derived from a second electric signal having a current amplitude set to a value corresponding to a percentage of a Tonic Perception threshold (TPT) of the subject. As used herein, the term Perception Threshold or Paresthesia Threshold (PT) relates to any type of stimulation, including priming and tonic stimulations.

It will be appreciated that any of the aspects, features and options described in view of the methods apply equally to the system, signal generation module and stimulation device. It will be understood that any one or more of the above aspects, features and options as described herein can be combined.

BRIEF DESCRIPTION THE DRAWINGS

The various features and advantages of the present invention may be more readily understood with reference to the following detailed description taken in conjunction with the accompanying drawings, wherein like reference numerals designate like structural elements, and in which.

Figure 19:
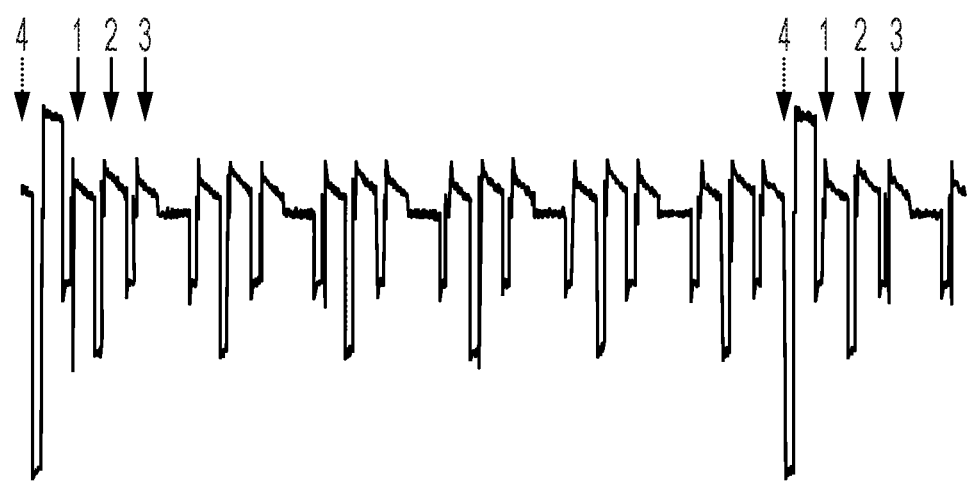
Figure 20:
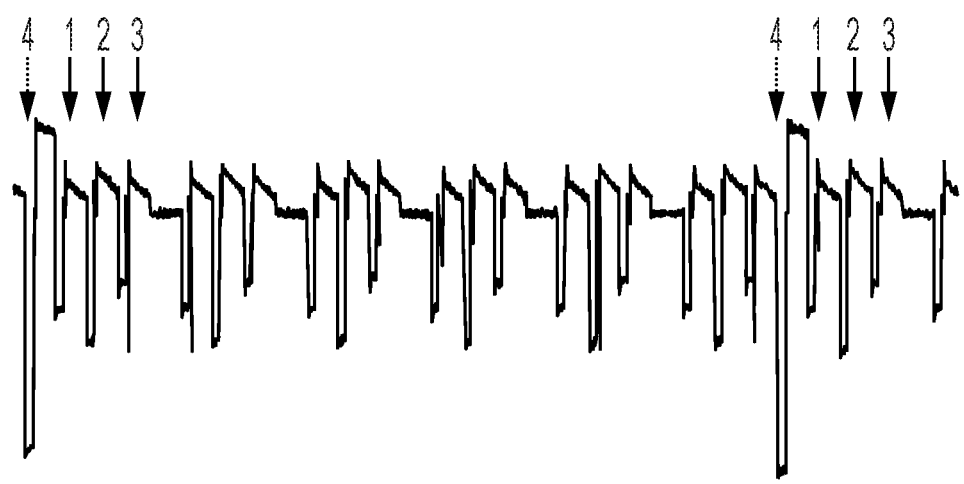
Figure 21:
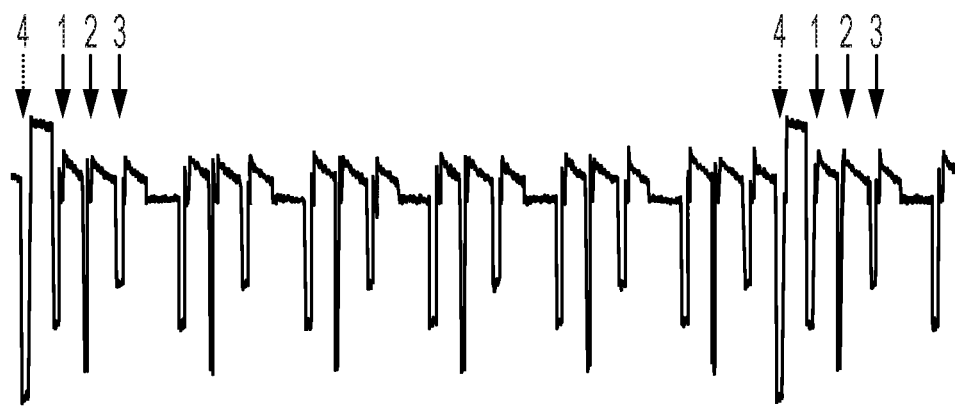
Figure 22:
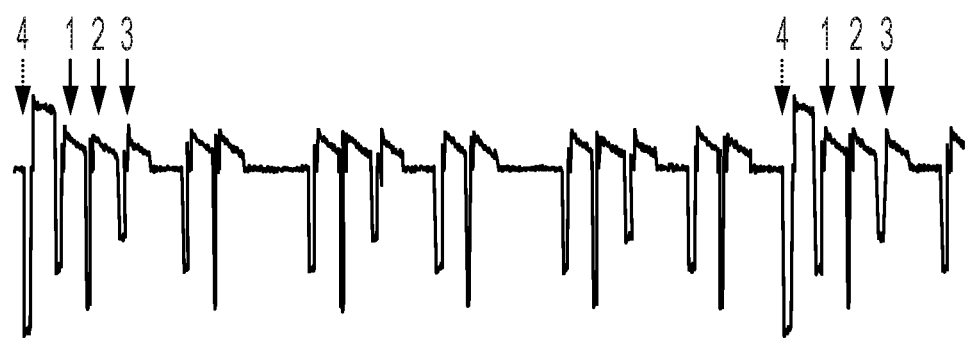
Figure 23:
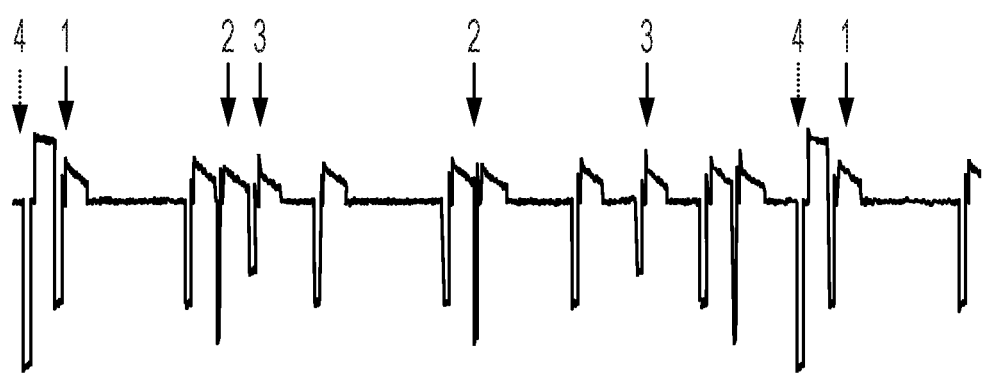
Figure 24:
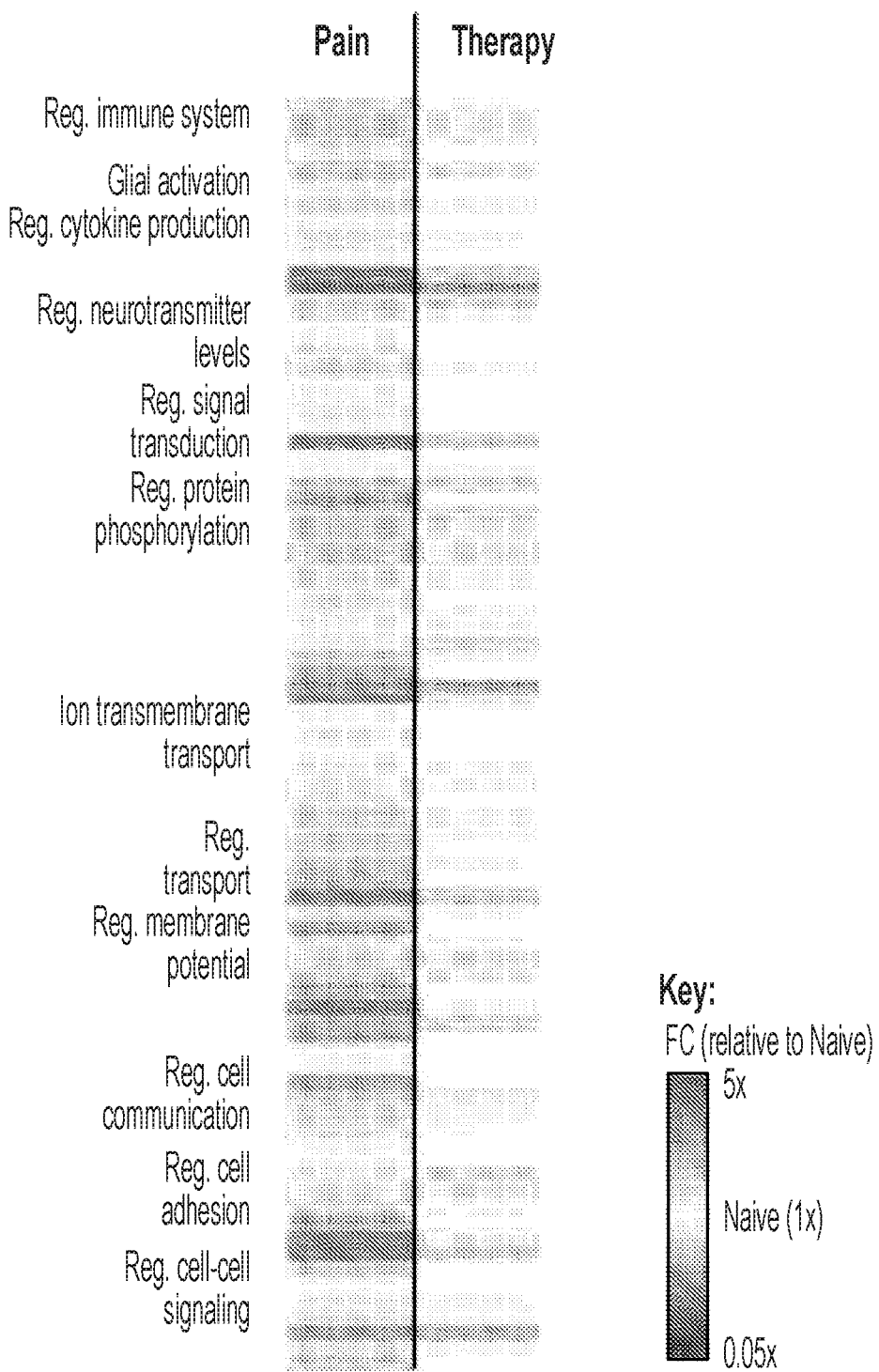

FIG. 19 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, with two signals, 2 and 4, having a different intensities than the other two, in accordance with exemplary aspects of the disclosure;

FIG. 20 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, all of the signals multiplexed having different intensities, in accordance with exemplary aspects of the disclosure;

FIG. 21 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, all of the signals multiplexed have different intensities, while signal 2 has a different pulse width, in accordance with exemplary aspects of the disclosure;

FIG. 22 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, all of the signals multiplexed have different intensities, while signal, has a different pulse width and signal 3 has a different pulse frequency, in accordance with exemplary aspects of the disclosure;

FIG. 23 illustrates a trace of a differentially multiplexed signal comprising four different signals, with signals 1, 2, and 3, multiplexed in one electrode array to target particular types of neural cells, while signal 4 is multiplexed with the other three signals at a different frequency using the same or another electrode array to target another type of neural cells, signal 2 has a different pulse width, while all signals differ in pulse frequency and intensity, in accordance with exemplary aspects of the disclosure; and FIG. 24 is a grayscale map showing the effect of differential targeting multiplexed therapy on gene expression relative to fold changes caused by the pain model relative to naïve (white color), with darker gray indicates larger changes in expression either up or down regulated, in accordance with exemplary aspects of the disclosure.

DETAILED DESCRIPTION

This application claims priority to, and benefit of, U.S. Provisional Application No. 62/843,757, filed May 6, 2019, and entitled "Method and Apparatus for Modulation of Cell Activity in Neural Tissue Using Multiplexed Electrical Signals on Differential Targets." This application also claims priority to, and benefit of, U.S. Provisional Application No. 62/964,281, filed Jan. 22, 2020, and entitled "Method and Apparatus for Multimodal Electrical Modulation of Pain Using Composite Electromagnetic Fields." The contents of all of these applications are incorporated herein by reference in their entirety for all purposes.

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

The oscillatory electromagnetic fields applied to neural structures induce changes in synaptic plasticity upon modulation of two different cell populations: Neurons and glial cells. This is concurrent with the effects on neurons such as action potential generation or blockade by the stimulation of mechanosensitive fibers to mask (or close the gate to) nociceptive signals travelling to the brain. In addition, glial cells are immunocompetent cells that constitute the most common cell population in the nervous system and play a fundamental role in the development and maintenance of chronic neuropathic pain. Glial cells are responsible for monitoring the status of the nervous system by using constant chemical communication with neurons and other glial cells. Microglia are the glial cells in charge of monitoring the brain and spinal cord. Following a nerve (or brain) injury, these cells become activated and respond to any stimulus that is considered a threat to Central Nervous System (CNS) homeostasis. This activation involves morphological changes in the microglia accompanied by changes in chemotaxis and phagocytic activity, as well as the release of chemokines and cytokines that induce a response from the immune system. It has been shown that microglia are the CNS immediate responders to injury. Injury also triggers the activation of astrocytes, glial cells that monitor the synaptic clefts and thus are involved in synaptic plasticity via the regulation of neuro and glial transmitter molecules and involvement of immune cells for synaptic pruning. Astrocyte activation and regulation is sustained for longer time and thus it can be hypothesized that astrocytes play an important role in changes affecting synaptic plasticity in chronic pain. There is experimental evidence that supports this hypothesis. It is worth noting that at the Peripheral Nervous System (PNS), oligodendrocytes, Schwann cells and satellite glial cells, similar to astroglia, play similar roles.

Calcium ions and phosphorylating processes mediated by ATP play an important role in glial response to injury. Electrical impulses induce changes in the concentration of calcium ions in the astrocytes, which propagates between astrocytes via calcium waves. This, in turn, signals the release of transmitters such as glutamate, adenosine and ATP, even after sodium channel blockade, which modulates both neuronal excitability and synaptic transmission. The presence of an external oscillatory electrical field then provides a stimulus for glial cells to affect synapses that have been negatively affected by injury. The electrical field provides a priming response that moves the function of the synapse towards a normal state.

Without being bound by theory, it is possible to electrically stimulate glial cells as their response (glial depolarization, release/uptake of ions, release of glial transmitters) depends on the specific parameters such as amplitude, frequency, phase polarity, waveform shape, and width (in the case of rectangular waveforms) of the stimulation. For example, the release of glutamate from astrocytes may be modulated in proportion to the amount of anodic current administered during biphasic pulsed stimulation. Monophasic cathodic stimulation of hippocampal astrocytes promotes the release of glutamate. The introduction of an anodic component decreases the amount of glutamate released. Given that the glial cells and neurons respond differently to electrical fields; it is then possible to differentially modulate the response of these cell populations with distinctly different electrical parameters. This theory sets a mechanistic basis of multimodal stimulation. Subthreshold stimulation with an electromagnetic field set at an optimum frequency, amplitude, waveform, width and phase may modulate the behavior of glial cells and the way they interact with neurons at the synaptic level. Thus, multimodal modulation provides the ability to control the balance of glutamate and glutamine in a calcium dependent manner and the possibility of modulating such balance in the appropriate manner with electromagnetic fields.

Electromagnetic fields modulate the expression of genes and proteins, which are involved in many processes involving synaptic plasticity, neuroprotection, neurogenesis, and inflammation. A genome-wide expression analysis of ipsilateral DC and DRG tissues obtained from an animal model of chronic neuropathic pain, in which SCS was applied continuously for 72 hours, provided findings that informed development of the multimodal methodologies described below. Without wishing to be bound by theory, the gene expression results indicated that the analgesic effect was likely induced at the molecular level in addition to, or independently of, the electric field blocking or masking nerve signaling. For example, SCS was identified to have upregulated genes for calcium binding proteins (Cabp), cytokines (Tnf, 116, 111b, Cxcl16, lfg), cell adhesion (ltgb) and specific immune response proteins (Cd68, Tlr2), all of which have been linked to glial activation. Modulation parameters, particularly the oscillation frequency and amplitude, may play an important role in the mode of action.

Multimodal Modulation Methodology

According to one exemplary aspect of the disclosure, a method for multimodal modulation utilizes a composite electric field with at least one component oscillating at a frequency higher than the other component. This composite electric field is believed to provide pain relief that exceeds the amount of pain relief provided by either electric field on its own. The electrical field of the higher frequency "priming" component provides a persistent electrochemical potential that m a y facilitate the stimulation of nerves by another component that is oscillating at a lower frequency. Without being bound by theory, the priming component lowers the threshold for depolarization of nerve fibers while simultaneously modulating glial activation. The priming component may also lower the impedance of the stimulated tissue, which allows for better penetration of the electric field into the neural tissue. The frequent pulsing of the priming component also contributes to a lower threshold for depolarization of nerve fibers via membrane integration of the electrical stimulus. Additionally, the priming component m a y contribute to neuronal desynchronization, which is a mechanism that helps with the reestablishment of neuronal circuits that have been unnaturally synchronized to maintain a nociceptive input into the brain.

In the disclosed prime multimodal modulation technique, a mechanism of depolarization is combined with amplitudes lower or slightly higher than the Paresthesia Threshold (PT), so the patient may or may not experience tingling even though tonic stimulation is being applied. In certain embodiments, a the composite signal, including the primary component that provides electrical stimulation at higher than the tonic frequencies, may activate the molecular mechanisms that allow for resetting of the synaptic plasticity to a state closer to the one previous to central sensitization induced by injury, thus providing a mechanism for long lasting pain relief.

In certain embodiments, the Priming Frequency (PF) may be set to any frequency between 200 Hz to 100 kHz. When a charged-balanced pulsed rectangular electrical component, e.g., biphasic symmetric, biphasic asymmetric, capacitor coupled monophasic, is used, the Pulse Width (PW) of the priming component may be set as low as 10 μs and as large as allowed by the priming frequency. For example, the maximum PW for a biphasic component with equal PW per phase and a 20 μs interphase delay is 395 μs for PF=1,200 Hz or 980 μs for PF=500 Hz. Either a voltage or current controlled composite signal may be used, although a current controlled signal may be more desirable as such signal does not depend on temporal impedance variations in the tissue being stimulated.

In certain embodiments, a first or priming frequency is between 1000 Hz and 1400 Hz (burst), or between 750 Hz and 1050 Hz (average). According to embodiments, multiple signals can be multiplexed within a repeating set of N pulse spaces. Each pulse space within the pattern can correspond to a different electrical signal with respective parameters. The lower average frequency can be generated by multiplexing a second, tonic signal component in one of the N pulses. According to embodiments, the burst frequency of the priming frequency signal component can be an integer multiple (M) of the tonic signal frequency such that the tonic pulse space only includes a pulse every M times the N set of pulse spaces are repeated. The blank pulse space results in a burst of N−1 pulses at the "burst" frequency, followed by a "missed" pulse resulting in a lower "average" frequency over the set of N pulses. As used herein, the average frequency of the priming signal is calculated separate without including pulses associated with the tonic signal. In some embodiments, the priming signal an be delivered to a different physical location using a different set of electrodes relative to the tonic signal. In another exemplary embodiment, the first or priming frequency is set to 1200 Hz (burst), or 900 Hz (average). In certain embodiments, each pulse within a burst may be provided on a separate program for different groups of electrodes, with a configuration set to allow for individual amplitude variability.

In further exemplary embodiments, a second or tonic component is set at a frequency of about 50 Hz, interleaved into the treatment to account for the average priming frequency, though other tonic values and ranges are contemplated herein, e.g., 20 Hz to 200 Hz, 20 Hz to 100 Hz, 30 Hz to 80 Hz, etc.

Multiplexed Modulation Methodology

In further exemplary embodiments, the present disclosure recognizes that the different glial cells and neurons in neural tissue respond differently to electrical fields, it is possible to differentially modulate the response of these cell populations with distinctively different electric signals which contain parameters that are characteristic to target and modulate the activity of a particular cell type. The disclosed system and method are based on the delivery of such signals in such a multiplexed fashion to modulate the activity of glial cells and neurons in neural tissue in order to balance neuroglial interactions away from the state that causes pain sensations to the subject. The multiplexed signals affect the expression of genes and proteins associated with relevant biological processes, which have been identified to be affected by chronic pain. The application of differential target multiplexed SCS signals to a live model of neuropathic pain normalizes the expression of such genes and thus the associated biological process towards those found in a healthy animal, which is referred to as a naïve animal herein.

RNA-sequencing has been used to study the effects of differential target multiplexed SCS on sets of mRNAs associated with various biological processes in a rodent model of neuropathic pain. A Weighted Gene Correlation Network Analysis (WGCNA) clustered more than 9,000 RNA transcripts in forty-one modules that clustered these according to expression patterns. WGCNA is complemented by a Gene Ontology Enrichment Analysis (GOEA) that identifies biological processes that involve gene transcripts clustered in the modules. The WGCNA allows the comparison of the effects of therapy in a group of subjects relative to a control group of subjects that did not receive therapy and a control group of naïve subjects. The WGCNA shows that the pain model significantly affected the expression pattern of genes in twenty-four modules relative to naïve animals. A therapy based on differential targeting multiplexed applied continuously for 48 hours reversed the expression patterns in twelve of such modules back to the naïve expression patterns. Table 1 illustrates the biological processes associated with the modules significantly reversed by the differential targeted multiplexed SCS therapy relative to the effect of the chronic pain, in which the GOEA identified enriched biological processes. FIG. 24 illustrates a grayscale map in which significant genes grouped in relevant biological processes are sorted by their fold change ratio between the expression levels under chronic pain relative to naïve (healthy). The map also illustrates the effect of the differential targeting multiplexed therapy, in which the expression of the majority of the genes folds back towards the levels in the naïve subjects.

shapes for one or more signals and may generate from such data step functions emulating signals at different frequencies. The processor performs algorithmic manipulation of such data to achieve the desired signal processing results. Digital to analog converters associated with the central processing module may convert the processed signal into a single output having the correct amplitude for coupling to one or plural electrodes arrays. In this manner, the interactive effects of multiplexed separate signals may be achieved with a single electrical composite signal capable of stimulating/modulating the interaction between glial cells and neurons in a manner that emulates the use of multiplexed separate signals.

In further exemplary embodiments, systems and devices described herein may be utilized to generate various differential target multiplexed electrical modulation signals, such as those illustrated in FIGS. 19-23. It may be appreciated by practitioners of the art that other differential target multiplexed electrical modulation signals may be conceived in accordance with the disclosure.

FIG. 19 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode arrays to target another type of neural cells, signals 2 and 4 having a different intensity (amplitude) than the other two.

As shown in FIG. 19, signals 1, 2, and 3 collectively repeat at a frequency higher than that of the interleaved

TABLE 1

WGCNA modules significantly affected by differential targeting multiplexed relative to the effect of chronic pain and relevant biological processes obtained via a GOEA

| WGCNA Modules | Biological Processes |
| --- | --- |
| 0 | Response to stimulus, Regulation of hormone levels, Signal transduction, Regulation of cell communication, Ion transport, Regulation of signaling receptor activity |
| 2 | Response to stress, Regulation of immune system process, Regulation of response to stimulus, Signal transduction, Regulation of transport |
| 3 | Response to stimulus, Translation, Peptide biosynthetic process, rRNA processing |
| 7 | Regulation of cell communication, Regulation of signal transduction, Regulation of response to stimulus, Trans-synaptic signaling, Regulation of protein phosphorylation, Regulation of MAPK cascade, Regulation of nervous system development, Regulation of ion transport |
| 9 | Response to extracellular stimulus, Response to nutrient levels, Phosphate-containing compound metabolic process |
| 12 | Response to stress, Regulation of phosphorylation, Immune response |
| 13 | Developmental process |
| 23 | Transport, Membrane organization, Signal transduction |
| 30 | Response to oxygen-containing compound |

In exemplary embodiments, a signal processor receives signals from one or more signal generator modules and is programmable to execute a multitude of algorithms for combining the separate signals into a single composite signal, including any of amplitude modulation, frequency modulation, signal summing, signal syncing, phase modulation, convolution, etc., or any combination thereof, as well as generation of customized signals from wave tables or digital oscillators in real time in response to user input data. The signal processor in conjunction with a breakout delay module facilitates multiplexing of the various signals provided to electrode arrays.

In further exemplary embodiments, a central processor module of a differential target multiplexed device may access stored numeric data mathematically describing wave signal 4. Thus, the burst frequency of signals 1, 2, and 3 is ¾ of the average frequency (ignoring the interleaved signal 4). According to various embodiments, the combination of signals 1, 2, and 3 can be provided to a first set of electrodes, while the interleaved signal 4 can be provided to a second set of electrodes. As used herein, the term simultaneous applies to signals 1-4 relative to one another. In particular, the individual pulses need not overlap to be considered simultaneous as the signals are each is composed of multiple pulses that together form a signal at a corresponding frequency.

FIG. 20 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, each of the four signals multiplexed having different intensities.

FIG. 21 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, all of the signals multiplexed have different intensities, while signal 2 has a different pulse width.

FIG. 22 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, all of the signals multiplexed have different intensities, while signal 2 has a different pulse width, and signal 3 has a different pulse frequency.

FIG. 23 illustrates a trace of a differentially multiplexed signal comprising four different signals, with signals 1, 2, and 3, multiplexed in at least one of the electrode arrays to target particular types of neural cells, while signal 4 is multiplexed with the other three signals at a different frequency using the same or another electrode array to target another type of neural cells, signal 2 having a different pulse width, while all signals differ in pulse frequency and intensity.

FIG. 24 is a grayscale map showing the effect of differential targeting multiplexed therapy on gene expression relative to fold changes caused by the pain model relative to naïve (white color), with darker gray indicates larger changes in expression either up or down regulated.

As will be discussed in more detail, below, exemplary processes for programming may be configured to determine a program algorithm for one program, followed by matching or setting the algorithm for other programs to be the same or adjusted based on the first program. Additionally, in exemplary embodiments, plural, different priming frequencies may be used, with varying selection of amplitude, pulse width and frequency to relieve pain.

The amplitude of a priming component may be set at a value below a Priming Perception Threshold (PPT), although setting it at or above the PPT is not excluded. The PPT may be found by slowly increasing the amplitude while feedback is obtained from the subject. Once the onset of perception is recorded, then the amplitude of the priming component may be changed to a value which is a percentage of the PPT (% PPT). With an exemplary PF of 1500 Hz, the signal may be then set for a given time, e.g., 10-30 minutes, before an electric component set at a tonic frequency lower than the PF, e.g., 10 Hz to 99 kHz, is applied independently to other electrodes in the lead. In one embodiment, with an exemplary PF of 200 Hz, the tonic frequency may be in the range of approximately 10 Hz to 199 Hz, for example. In the prime mode of stimulation, the tonic frequency will be lower than the priming frequency but is not necessarily limited to a particular range of frequencies below the priming frequency.

The Pulse Width (PW) of a charge-balanced, e.g., a biphasic symmetric, biphasic asymmetric, or capacitor coupled monophasic, pulsed signal can be as low as 10 μs and as large as allowed by the set tonic frequency. In exemplary embodiments, the pulse width may be between about 100 and 500 microseconds, between about 100 and 400 microseconds, between about 150 and 200 microseconds, or any different value, range or combinations of pulse widths.

The signal generation and delivery circuitry may also allow for modifying the duty cycles of pulsed width signals and various schemes in which the time of initial priming can be varied, as well as the times in which the priming signal is on or off relative to the time when the tonic signal is delivered. The amplitude of the tonic electrical component, which could be either voltage or current controlled, may be set above, below or at the Tonic Perception Threshold (TPT). PT may be obtained by increasing the amplitude of the tonic component while getting feedback from the patient. The tonic amplitude may then be set to a value corresponding to a percentage of the TPT (% TPT). In the prime multimodal modulation methods described herein both the priming component and the tonic component may be below 100 kHz, in one embodiment. In another embodiment, the tonic signal may be below 500 Hz. In still another embodiment, the tonic signal may be below 100 Hz. In one embodiment, the ratio of priming component frequency to tonic component frequency may be in the range of 2:1 to 40:1, 4:1 to 40:1, 10:1 to 40:1, 20:1 to 40:1, up to 70:1, up to 140:1, etc. depending on the specific values of the frequencies chosen.

In yet another embodiment of multimodal modulation therapy, the priming component may be biphasic in which the polarity of the first phase of the biphasic prime component may be either cathodic or anodic. With this embodiment, the tonic component may have characteristics that are different from those of the priming component. The tonic component may be biphasic with the polarity of the first phase of the biphasic tonic signal being either cathodic or anodic.

In exemplary embodiments of multimodal modulation therapy, an active recharge mode provides a recovery pulse that applies an equal charge in a direction opposite to the input, thus driving the waveform each way.

The techniques disclosed herein may be achieved with minimally invasive procedures which are preferred over those that require extensive surgical intervention and healthcare expenses although in particular circumstances, a surgical implantation may be required. Electrical stimulation leads, similar to those illustrated in FIGS. 3A and 38, can be used, but other designs having a different number of electrodes, size of the electrical contact, spacing between contacts, and geometrical arrangement of electrodes within an array may be utilized to deliver electromagnetic stimulation to a neural structure. In exemplary embodiments, various electrode and lead configurations provide spacing configured to modulate glial cells and neurons.

In an embodiment, a lead comprises a cylindrical arrangement of multiple electrodes, e.g., between 4 and 16. The diameter of the lead may be small enough to allow for percutaneous implantation into the spinal canal using an epidural needle under standard clinical practice. The electrodes are made of biocompatible materials such as iridium-platinum alloys, which are also resistant to corrosion. For example, a 50 cm long lead implemented with eight electrodes may have a diameter of 1.35 mm, with each cylindrical electrode having a length of 3.0 mm, and a spacing between electrodes of 4.0 mm. Conducting wires may run from the electrodes to the distal part of the lead into metal connectors. The wires may be enclosed within a triple-insulated containment made of a biocompatible durable polymer.

Figure 3A:
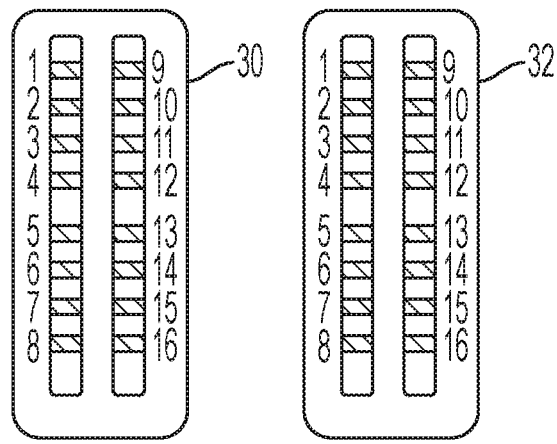
FIGS. 3A and 3B illustrate conceptually electrode arrays that may be utilized with a system in accordance with an embodiment of the present disclosure.
Figure 3B:
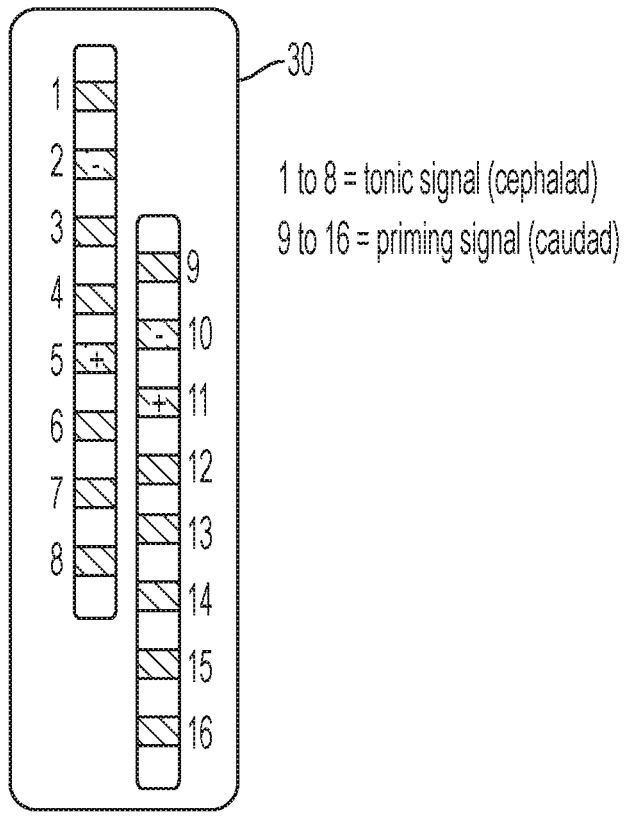

In the case of multimodal modulation of the spinal cord, various multi-contact leads can be positioned in the epidural space to stimulate the cell populations already described. In one particular arrangement, the leads can be positioned parallel to each other, although not necessarily coplanar within the epidural space. FIG. 3A illustrates two eight-contact electrode arrays that can be used for the disclosed multimodal modulation techniques. Note that the polarity of the leads can also be customized during the programming stage, either as bipolar, monopolar, or guarded cathode configurations. Another example of a possible electrode array arrangement is shown in FIG. 3B in which the leads are arranged staggered relative to each other. The customization and optimization of therapy may comprise the positioning of the leads within the epidural space at appropriate vertebral segments in either type of lead arrangement.

Other arrangements may be used to stimulate different places along the spinal canal, e.g., the leads do not need to be parallel. For example, in one arrangement, one lead can be dedicated to deliver a signal at the spinal cord at a given vertebral level, while the other provides a signal either more caudad or cephalad relative to the position of the other lead. Leads can be, in principle, located at any vertebral level in the spinal cord, or could also be positioned peripherally, because the principle behind multimodal modulation applies to peripheral glial cells that survey the axons.

Furthermore, the multimodal stimulation electromagnetic fields location and penetration may be also utilized for customization and optimization of therapy by delivering multimodal stimulation signals to particular arrays of electrodes within each lead by setting monopolar, bipolar, or guarded cathode arrangements of such electrode arrays. For example, therapy for a patient with low back pain that extends into one of the lower extremities may require positioning the stimulation leads in a staggered arrangement within the epidural space along vertebral levels thoracic 8 (T8) and thoracic 12 (T12). An array of electrodes in the more cephalad of the leads may be set to monopolar, bipolar or guarded cathode arrangement. Another array of electrodes in the more caudad of the leads may be set to monopolar, bipolar or guarded cathode arrangement. The clinician will be able to customize the electrode array setting in a methodical manner such that therapy can be optimized for based on feedback from the patient.

Figure 14:
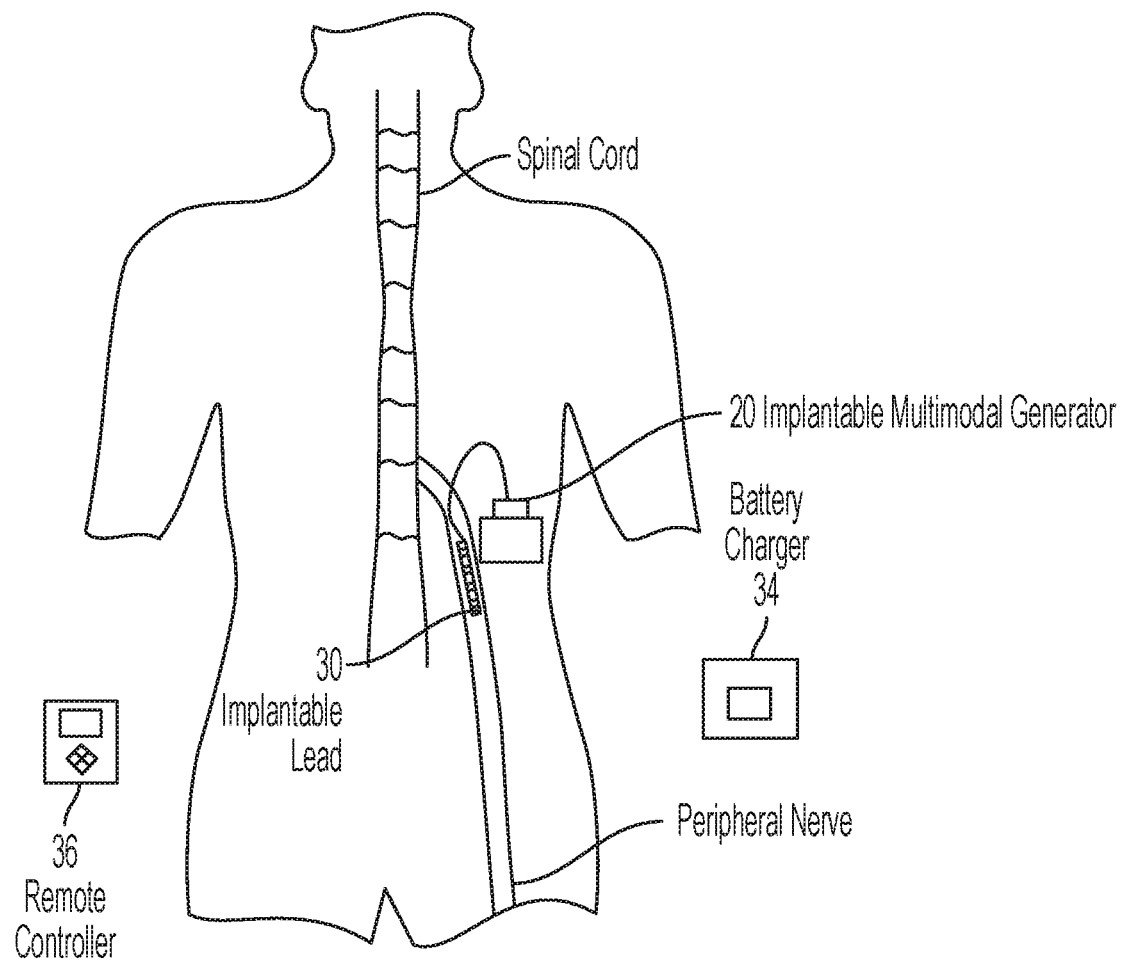
FIG. 14 illustrates conceptually the placement of an implantable system with a human subject in accordance with an embodiment of the present disclosure.

Optionally, pain relief may also be used by position the leads in the neighborhood of a peripheral nerve as illustrated in FIG. 14. Peripheral Nerve Stimulation (PNS) is an alternative therapy for chronic pain in which a target nerve has been identified to be the source of pain. The current understanding of the therapeutic effects of PNS is also based on the gate control theory. However, axons of sensory neurons in peripheral nerves are surrounded by glial cells that are known to respond accordingly to the frequency characteristics of a stimulus.

Multimodal peripheral nerve stimulation involves the positioning of one or more stimulation leads around or in the neighborhood of a target nerve. The leads are connected to a signal generator with multimodal capacity as described herein. Multimodal stimulation is delivered to the neural tissue consisting of neuron axons and their corresponding glial cells (Schwann cells) according to the principles and methods described in this application. The leads may implant to be positioned around the target nerve using an invasive surgical approach or percutaneously utilizing a needle cannula.

Alternatively, as would be the case for the stimulation of target nerves that are close to the skin surface (such as the vagus nerve, nerves in the joints of the extremities, etc.) the leads may be arranged inside a conductive biocompatible pad for delivery of the multimodal electromagnetic field transcutaneously. This embodiment constitutes Transcutaneous Electrical Nerve Multimodal Stimulation (TENMS). In this embodiment, the priming high frequency component of the multimodal signal lowers the impedance of the skin and subcutaneous tissue and allows for better penetration of the tonic signal. The priming signal also provides a modulating signal for perisynaptic glial cells in the neuromuscular junction. These cells are known to discriminate different stimulation patterns and respond accordingly, thus allowing for modulation of the synapse with multimodal stimulation. The tonic component of the multimodal signal is used to stimulate the neuronal axon at lower thresholds.

Systems Components

Figure 1:
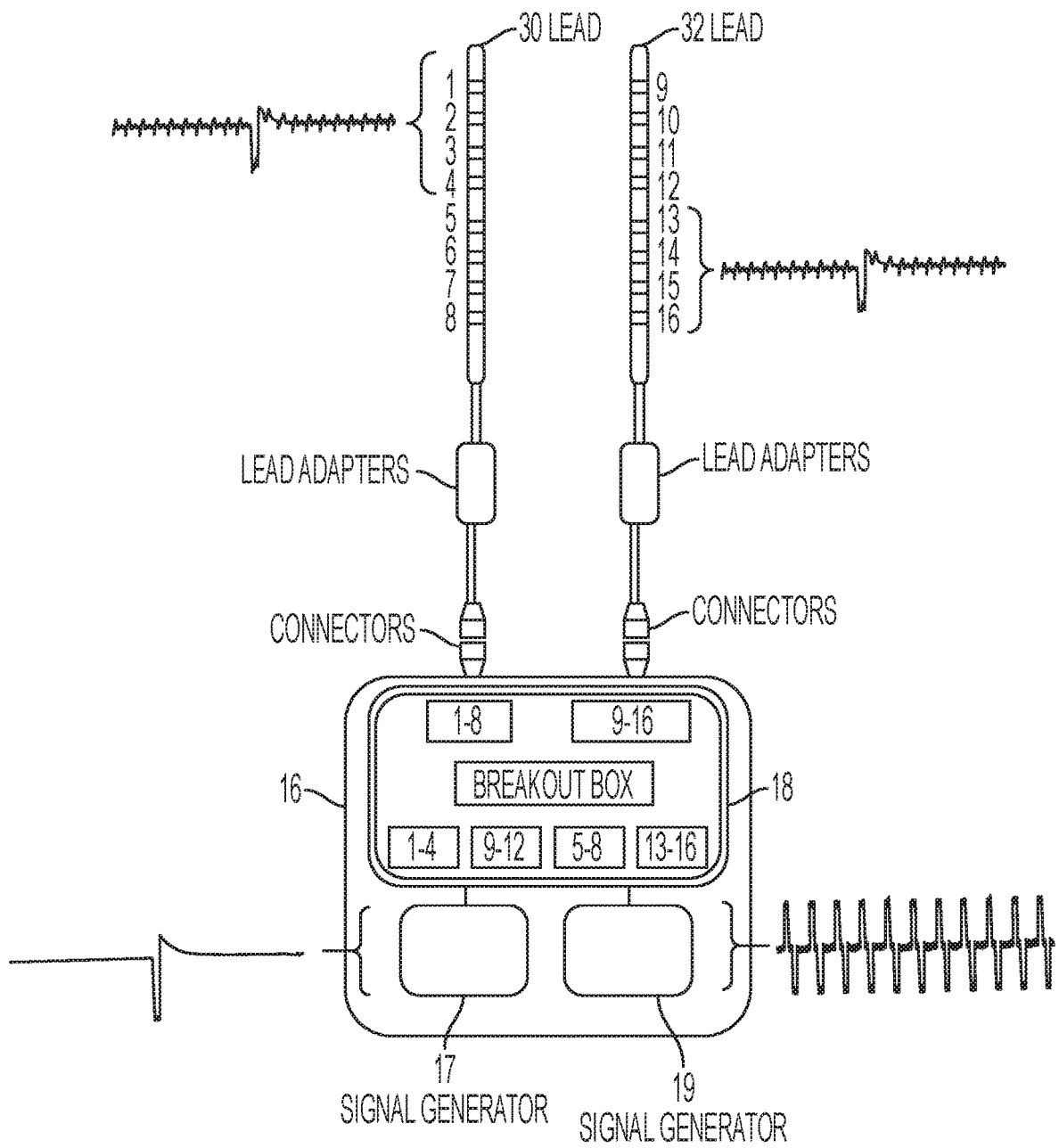
FIG. 1 is a schematic diagram illustrating an apparatus for pain management in accordance with an embodiment of the present disclosure.

FIG. 1 illustrates conceptually an embodiment of a multimodal stimulation system that may be utilized to perform the methods disclosed herein. The system comprises a pair of electrical leads 30 and 32, each of which may be implemented with an array of electrode contacts, a breakout box 18 and signal generators 17 and 19, as illustrated. Breakout box 18 is electrically coupled to leads 30 and 32 and signal generators 17 and 19 through appropriate connectors. The breakout box 18 and signal generators 17 and 19 may be placed in an enclosure referred to as an External Stimulator Unit (ESU) system 16. Each of generators 17 and 19 delivers a particular signal with parameters that can be set separately for each other. Each of generators 17 and 19 may have the functional characteristics and architecture elements similar to generator 20 described herein without an exterior enclosure suitable for implantation into a patient. In one embodiment, system 16 may also include one or more of the modules described herein with reference to Implantable Multimodal Generator 20 and FIG. 2.

The ESU system 16 is electrically coupled to electrical leads, each of which may be implemented with an array of electrode contacts. In an embodiment, a pair of leads 30 and 32 is coupled to the ESU 16 using appropriate connectors as illustrated in FIG. 1. In another embodiment, a single lead implemented with an array of electrodes can be used. In a configuration for performing prime multimodal modulation, one of generators 17 or 19 may be configured to deliver a priming component, for example 1,200 Hz, and the other generator may be configured to deliver a tonic component, e.g., at 50 Hz. The breakout box 18 may be used to reconfigure the delivery of signals to the proper electrode contacts in leads 30 and 32. In the embodiment illustrated in FIG. 1, the electrode contacts 1-8 in electrode array 30 can be split such that electrode contacts 1-4 deliver a first signal, e.g., a tonic signal, different than a second signal delivered at electrode contacts 5-8 thereof, e. g. a priming signal. Similarly, electrode contacts 9-16 of electrode array 32 may be split such that electrode contacts 9-12 thereof deliver a signal similar to that delivered by electrode contacts 1-4 in electrode array 30, while electrode contacts 13-16 thereof deliver a signal similar to that delivered at electrode contacts 5-8 in electrode array 30, as illustrated.

Implantable Multimodal Generator

Figure 2:
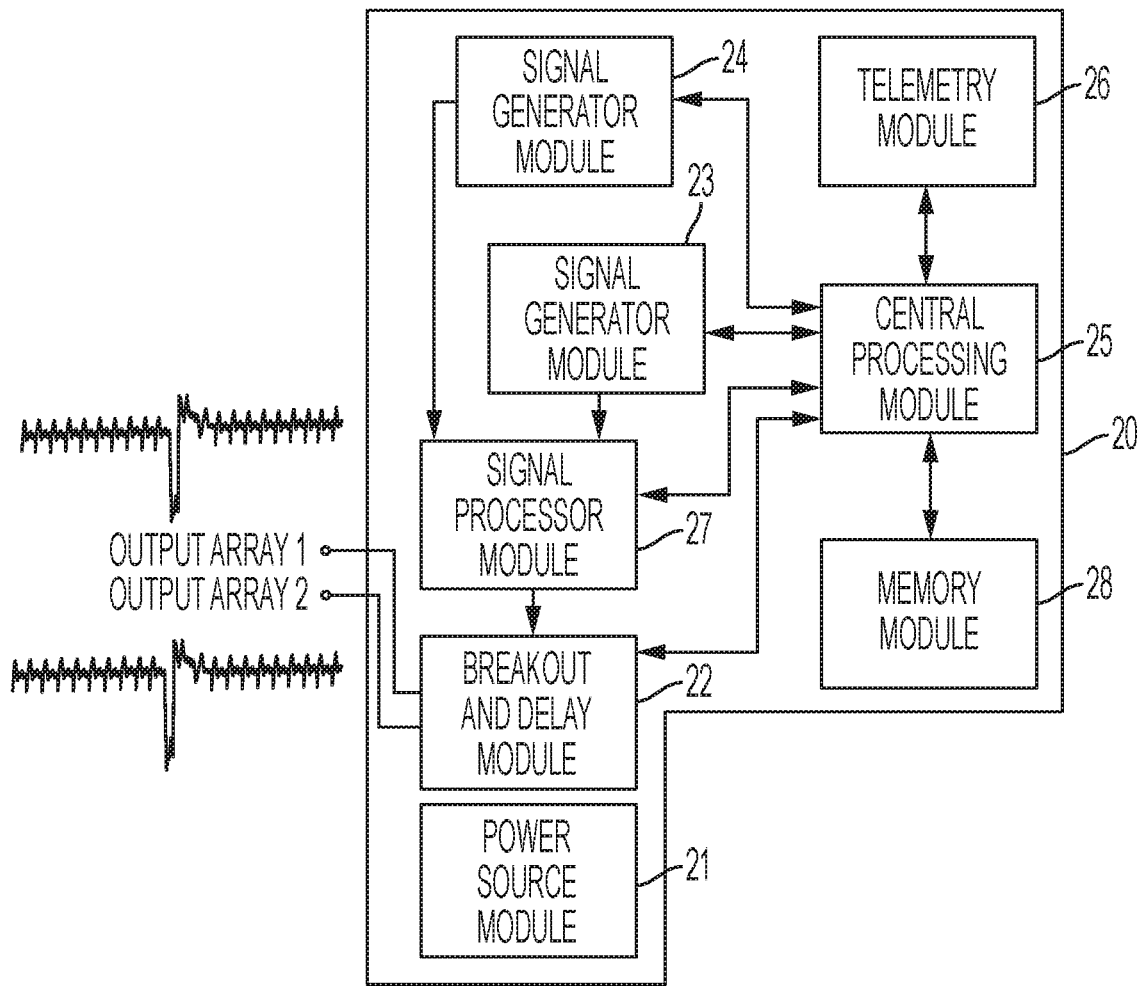
FIG. 2 illustrates a schematic circuit diagram of an implantable multimodal modulation device that may be utilized with a system in accordance with an embodiment of the present disclosure.

FIG. 2 illustrates conceptually a block diagram of the elements comprising an Implantable Multimodal Generator (IMG) 20. The generator circuitry may be hermetically sealed in a housing made of a durable biocompatible material, such as stainless steel or titanium. The generator 20 has an output interface for establishing electrical connection with arrays of electrodes implemented within the previously described leads 30 and 32 that deliver the multimodal signals to glial cells and neurons. In one embodiment, the implantable multimodal generator 20 comprises a central processing module 25, a memory module 28, a telemetry module 26, a power source module 21, signal generator module 23, signal generator module 24, and a Breakout and Delay module 22, and signal processor 27, including the output interfaces thereof. In embodiments, the elements of implantable multimodal generator 20 may be interconnected as illustrated in FIG. 2, or, may be connected through a central bus, which enables intercommunication amongst all components depending upon the actual implementation.

The central processing module 25 may be implemented with a microprocessor integrated circuit or may comprise reduced functionality small-scale logic, but in either implementation includes a wireless transceiver functionality that enables bidirectional wireless communication of information with an external programmer unit (not shown) or a user-controlled remote 36.

The memory module 28, which may be implemented with either RAM or ROM memory, may be used to store a modulation program, executable by central processing module 25, which generates functional information of the generator 20. The central processing module 25 is able to store and retrieve information from a memory module 28 as commanded by the user.

The telemetry module 26 is used to communicate via a wireless protocol with the external programmer unit (or control remote) and includes transceiver circuitry in order to conduct wireless communications with devices remote from generator 20 according to any number of established wireless protocols.

The power source module 21 may comprise a rechargeable or a non-rechargeable battery and electronic circuitry that distributes power from the battery to all the other components in the implantable multimodal generator 20.

The signal generator module 23 comprises electronic circuitry that allows the delivery of charge-balanced waveforms of any waveshape, including but not limited to biphasic or monophasic pulses, sinusoidal trains, sawtooth trains, triangle trains, and bursts thereof.

In one embodiment, signal generator module 23 comprises electronic circuitry that allows the delivery of noise signals, such as white noise, with a constant power spectral density, or pink noise, with equal energy in octave intervals, or other noise signals in which the energy within the signal spectrum is distributed in other patterns. In one embodiment, a noise signal may be used as the priming component in the techniques disclosed herein. The signal generator module 23 is able to deliver these waveforms at frequencies ranging from 1 Hz to 100 kHz. For pulse delivery, the signal generator module 23 is able to deliver rectangular pulse waves over a range of widths, e.g., as small as 1 µs and as large as 250 ms, depending on frequency. The signal generator module 23 is further capable of generating a range of interphase delays. The signal generator module 23 is designed to deliver a signal, with amplitude, which is either voltage controlled or current controlled, over a range of values, e.g., 0 V to 30 V or 0 mA to 30 mA, respectively. The signal generator module 23 is also able to generate pulses with a duty cycle. The signal generator module 23 is controlled by the central processing module 25 according to parameters selected by the user in an external programmer unit (or control remote). The signal generator module 23 may be implemented with analog or digital circuitry or a combination thereof.

Signal generator module 24 may be structurally and functionally similar or dissimilar to signal generator module 23 and may be independently controlled and programmed.

Signal processor 27 may be implemented with a special-purpose digital signal processor (DSP), or, may comprise a programmable general-purpose DSP. Signal processor 27 may be implemented with any number of commercially available signal processing integrated circuit components having a specialized instruction sets and processor capable of performing algorithmic manipulation of one or more signals input thereto.

Signal processor 27 receives signals from signal generator modules 23 and 24 and is programmable to execute a multitude of algorithms for combining the separate signals into a single composite signal, including any of amplitude modulation, frequency modulation, signal summing, signal syncing, phase modulation, convolution, etc., or any combination thereof, as well as generation of customized signals from wave tables or digital oscillators in real time in response to user input data. Signal processor 27 may have associated therewith a scratchpad memory area used for local storage of data and program variables when performing signal processing or other tasks. In addition, signal processor 27 may also comprise specialized analog circuitry such as filters, control circuitry, and circuitry for creating a composite signal from signals from signal generator modules 23 and 24. Depending on whether the output of the signals generated by signal generator modules 23 and 24 is analog or digital, signal processor 27 may also include its own analog-to-digital converter and digital-to-analog converter for converting any input signals into the proper format for processing and converting the signal into the proper format for output to breakout and delay module 22.

The breakout and delay module 22 comprises an accurate timer electronic circuitry that can slave one of signal generator modules 23 or 24 to the other, so that a delay can be produced between signals generated therefrom such that a synchronized delivery of such signals can be programmed by a user. The breakout and delay module 22 also incorporates electronic circuitry, called breakout, that allows for the user to select an option in which the output array 1 delivers a signal to all top (rostral during spinal cord stimulation) electrode contacts of a pair of electrode arrays (for example, tonic 50 Hz, 250 µs pulse width, 3.0 mA), while output array 2 delivers a signal to all bottom electrode contacts of a pair of electrode arrays (for example, a priming signal of 1,200 Hz, 100 µs pulse width, 3.5 mA). An example of this option is shown in FIG. 3A.

Another option is one illustrated in FIG. 38 where the breakout option can be bypassed. In that case, all contacts in a given electrode array will be set at the same modulation parameters as delivered by, for example, signal generator module 23. All contacts in the other electrode array will be set to the same modulation parameters as delivered by the other signal generator module. In embodiments in which the same composite signal is provided as outputs to both array 1 and array 2, the functionality of breakout and delay module 22 may be performed entirely by signal processor 27, obviating the need for breakout and delay module 22, assuming the appropriate output interface is used to properly couple the outputs of signal processor 27 to the electrode arrays.

In one embodiment, all or most of the functional blocks of generator 20 may be fabricated on a single integrated circuit chip including a microprocessor and associated memory, wireless transducer and one or more digital oscillators. Alternatively, the digital oscillators may be replaced with wave tables having stored therein mathematical descriptions of various waveform data values, which are convertible into analog signals using a digital to analog converter, integrated into or associated with the processor module 25 or signal generator modules 23 or 24, depending on their respective implementations. Such wavetables may be stored in processor module 25 or memory module 28.

In other embodiments, the various modules of IMG 20 may communicate over a central bus internal thereto or may have dedicated direct connections there between, or any combination thereof.

In one embodiment, IMG 20 or ESU 16 may be programmed by a clinician using software that allows control of all the aspects of the system. The software may be accessible in a computer-based interface called the Clinician Programmer (CP) software. The software may be implemented with wireless communication protocols for remote access of the IMG 20 or ESU 16. ESU 16 may also be provided with a network port such as a USB or micro-UBS port for interacting with the CP. In the case of IMG 20, the CP software enables the clinician to communicate with central processing module 25 to define a set of parameters, e.g., any of amplitude, frequency, phase, phase polarity, waveform shape, and width (rectangular waveform), etc., of the signal generated by signal generator modules 23 or 24 and to further define the parameters of their relative timing by defining the operational parameters of breakout and delay module 22. Such defined parameter sets may be stored as one or more configuration programs in memory module 28 or in memory associated with central processing module 25.

In one embodiment, one or more configuration programs may be stored in memory associated with remote controller 36 and the parameters thereof transmittable to IMG 20 via telemetry module 26 for control of generator modules 23 or 24 and of breakout and delay module 22. The CP software may enable the clinician to further define which parameter the patient my control with the remote controller 36 and to define any limits on such parameter.

For example, the clinician can set and store a configuration program #1 with parameters that provides prime multimodal stimulation consisting of priming with a biphasic symmetric rectangular pulsed signal component set at 1,200 Hz, 150 μs PW, and current-based amplitude set as a % PPT, and a tonic signal component delivering biphasic asymmetric pulses (rectangular and exponentially decaying phases) at 50 Hz, 400 μs PW, and current-based amplitude set as a % PT. The composite signal can be delivered to a particular set of electrodes in the leads.

The clinician can also set and store a configuration program #2 that provides prime multimodal stimulation consisting of a priming with biphasic symmetric rectangular pulses at 900 Hz and 300 μs PW and tonic signal component delivering biphasic symmetric rectangular pulsed at 100 Hz and 400 μs PW and each set at its own current-based amplitude set a particular % PT. These signals can be delivered to a particular set of electrodes in the leads which may be different to that used in configuration program #1. The system allows for setting and storing additional configuration programs deemed necessary for the clinician and according to the storage capacity of the memory module 28.

Limited control of the multimodal configuration programs may be available to the patient via a remote controller 36. In one embodiment, the clinician can access one or more configuration programs using the CP to control any of the parameters of a configuration program already stored in the ESU 16 or IMG 20. The patient may be able to browse and/or select any available configuration program with the remote controller The patient may be able to change the current-based amplitude of any particular configuration program up to a particular setting determined by the PPT or PT in order to optimize pain relief, for example. Note that the remote controller 36 may be provided with a simple interface, such as a selector switch, or dial to select the appropriate configuration program, or a more sophisticated user interface including a visual display with directional keys or touch sensitive menus.

In the embodiments described herein, the option exists for user feedback and control of the system through the programming device. As stated above, the initial settings for priming and tonic frequencies will be programmed by the physician or a clinical field engineer. After this point, the device can allow the patient to change many settings, including the priming and tonic frequencies, parameters of either frequency such as amplitude, duty cycle, pulse width, or phase. In an embodiment, the patient will be able to adjust the tonic stimulation frequency from its initial setting to any frequency between 10 Hz and the priming frequency (fp) minus one. Using the above example of a priming frequency of 1,200 Hz, the tonic frequency could be adjusted between 10 Hz and 1,199 Hz.

In another embodiment, the patient will be able to alter the amplitude of the tonic amplitude, with the range of amplitudes limited between zero and the amplitude of the Priming Stimulation. The patient may also be able to alter the pulse width and duty cycle of either the priming stimulation or the tonic stimulation when the stimulation waveform is comprised of discrete pulses separated by latent periods. These values will be limited by the selected frequencies. The frequency of stimulation determines the time between pulses (herein defined as the period). Due to the requirement of charge balancing, the pulse width can be no larger than the period divided by two. Thus, the patient can shift the pulse width between a minimum value of 10 μs and half the period.

The final patient-controlled aspect is the phase of the waveforms. In this embodiment, the patient will be able to shift the tonic stimulation or priming stimulation throughout its period. A phase of zero would correspond to a pulse occurring at the start of a duty cycle and the remainder of the cycle being void of stimulation. The user can shift the location of that pulse to any point along the duty cycle, with the phase being confined to a maximum value equal to the period. The phase shift of a pulse through its period creates different constructive effects of the electric fields or the signals themselves. This will result in a waveform that appears unique to the neural tissue, despite being comprised of the same priming and tonic frequencies. The purpose of allowing patients to adjust these parameters is to provide each patient with increased control over their pain relief.

Figure 4:
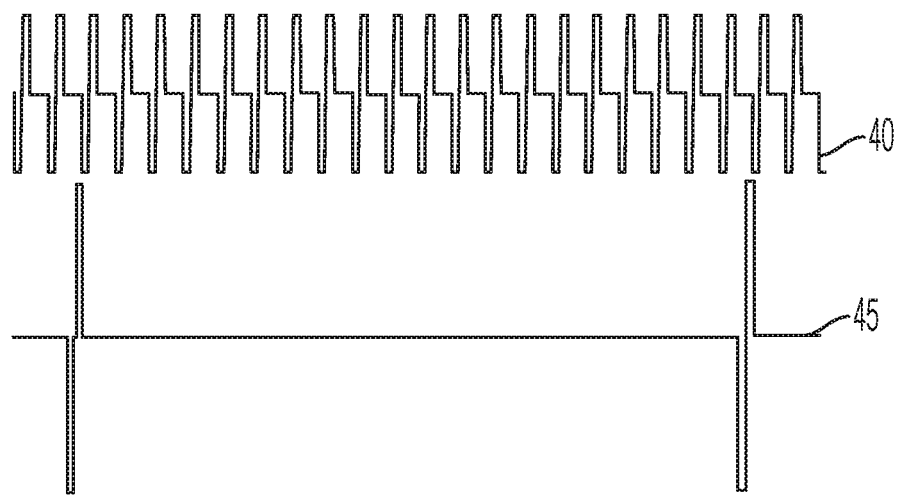
FIG. 4 illustrates conceptually a pair of traces representing signals that may be used in an example of prime multimodal modulation in accordance with an embodiment of the present disclosure.

FIG. 4 illustrates conceptually a pair of traces representing signals 40 and 45 used in an example of prime multimodal modulation. Signal 40 functions as a priming electrical component and may comprise, for example, biphasic rectangular pulses with a frequency of 1,200 Hz, PW=200 μs and interphase delay of 20 μs (though other delays are considered herein, e.g., an 80 microsecond delay between the therapy pulse and the recharge/recovery pulse, with a 40 microsecond gap between the end of the recovery pulse and the next stimulation pulse (e.g., for exponentially decaying recovery pulse)). Signal 45 functions as the tonic component and may comprise, for example, biphasic rectangular pulses with a frequency of 50 Hz, PW=200 μs and interphase delay of 20 μs. In this example, the amplitude of the tonic component is set to be larger than the amplitude of the priming component. Signals 40 and 45 have been offset in FIG. 4 for visual clarity. Signals 40 and 45 may be used to generate a composite signal using the system and techniques described herein.

Figure 5:
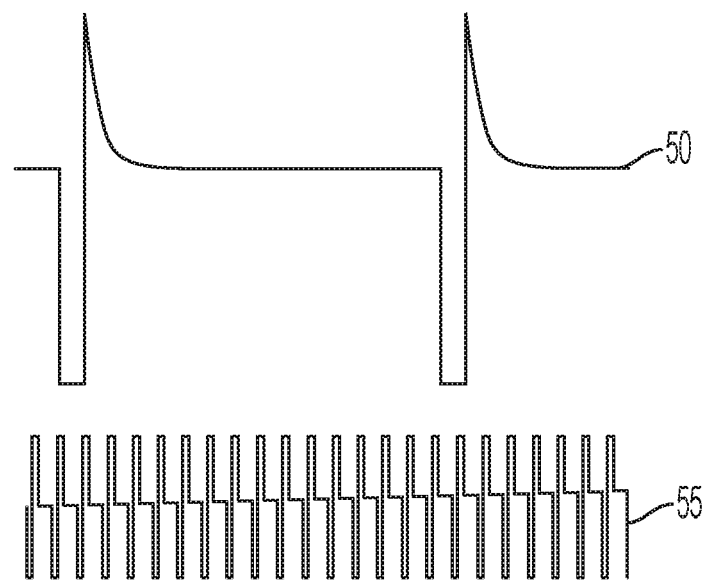
FIG. 5 illustrates conceptually a pair of traces representing signals that may be used in an example of prime multimodal modulation in accordance with an embodiment of the present disclosure.

FIG. 5 illustrates conceptually a pair of traces representing signals 50 and 55 used in an example of prime multimodal modulation. Signal 55 functions as a priming electrical component and may comprise, for example, biphasic rectangular pulses with a frequency of 1,200 Hz, PW=150 µs and interphase delay of 20 µs. Signal 50 functions as the tonic component and may comprise, for example, biphasic asymmetric rectangular/exponential decay pulses with a frequency of 50 Hz, PW=400 µs and interphase delay of 20 µs. In this example, the amplitude of the tonic component is set to be larger than the amplitude of the priming component. Signals 50 and 55 may be used to generate a composite signal using the system and techniques described herein.

Figure 6:
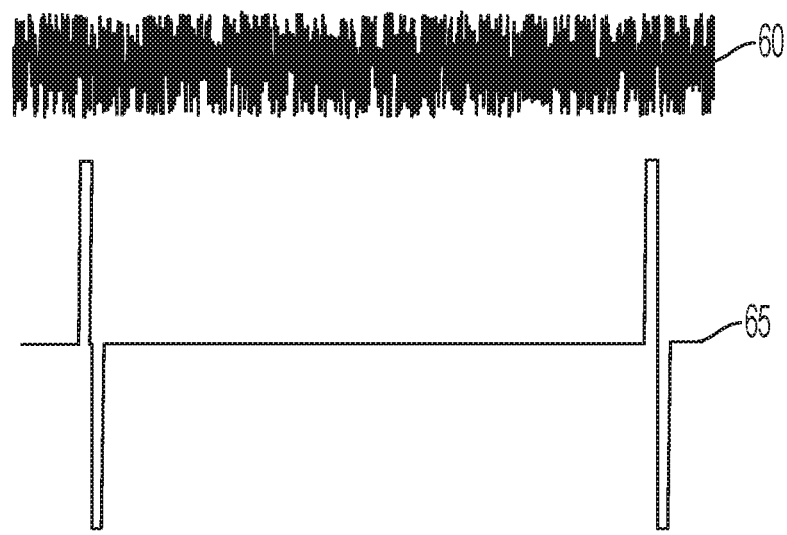
FIG. 6 illustrates conceptually a pair of traces representing signals that may be used in an example of prime multimodal modulation in accordance with an embodiment of the present disclosure.

FIG. 6 illustrates conceptually a pair of traces representing signals 60 and 65 used in an example of prime multimodal modulation. Signal 60 functions as a priming electrical component and may comprise, for example, white noise of a particular maximum amplitude. Signal 65 functions as the tonic component and may comprise, for example, biphasic symmetric rectangular pulses with a frequency of 50 Hz, PW=400 µs and interphase delay of 20 µs. In this example, the amplitude of the tonic component is set to be larger than the amplitude of the priming component. Note that in FIGS. 4-6 the signals representing the tonic and priming waveforms are offset for visual clarity, such offset not meant to be limiting in any matter. Signals 60 and 65 may be used to generate a composite signal using the system and techniques described herein.

The ESU 16 or IMG 20 may deliver multimodal stimulation using a single composite modulation/stimulation signal, which has rhythmically varying characteristics, and, therefore, alternating magnetic field characteristics which achieve the same results as when combining two separate signal components. In such an embodiment, a composite signal characterized by typically alternating characteristics is utilized to obtain the same stimulation and modulation of the interaction between glial cells and neurons. Such a composite signal may be generated by signal processor 27 which is capable of executing a multitude of algorithms for combining separate signals into a single composite signal including any of amplitude modulation, frequency modulation, signal summing, signal syncing, phase modulation, or convolution or any combination thereof, as well as and generation of customized signals from wave tables or in real time, such composite signals having any of periodic or aperiodic characteristics. In addition, pulse width modulation may be used to create a composite signal having variably changing harmonic energy content may similarly be utilized to achieve the desired multimodal stimulation of glial and neuronal cells.

Figure 7:
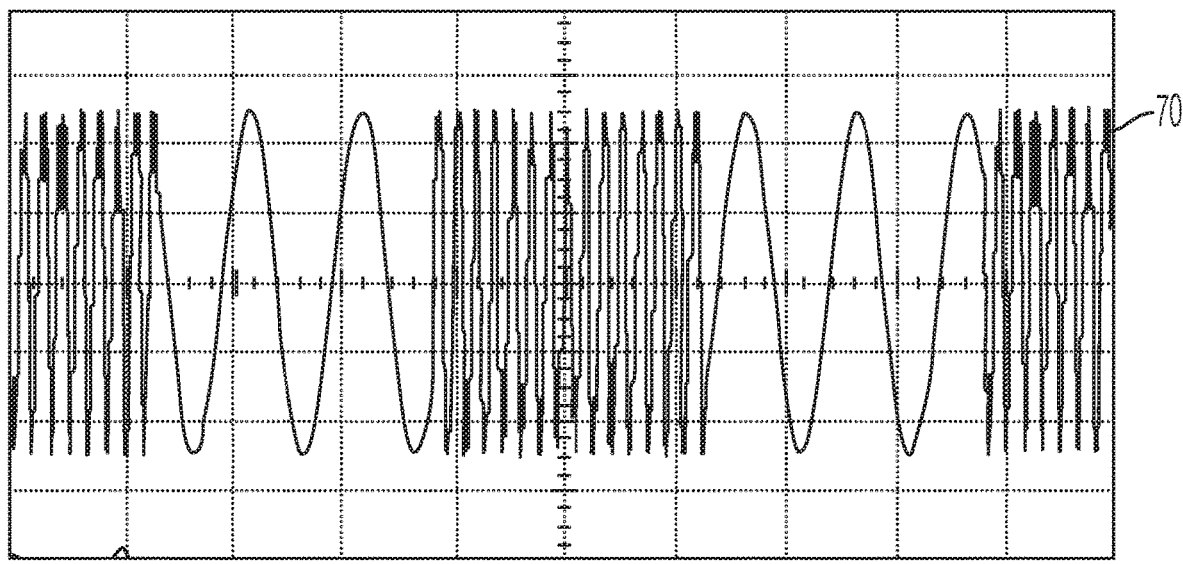
FIG. 7 illustrates conceptually a frequency modulated signal, with a carrier frequency larger that the modulating frequency, that may be utilized for multimodal modulation in accordance with an embodiment of the present disclosure.

FIGS. 7-12 illustrate conceptually example of multimodal composite signals formed by frequency modulated, dual combined sinusoidal, dual combined biphasic rectangular pulses, frequency changing signals, and white noise combined with low frequency pulses, respectively, that may be utilized for multimodal modulation. FIG. 7 illustrates conceptually a frequency modulated composite signal 70 in which the priming signal component thereof is delivered for a given period of time before the tonic signal component thereof is delivered for a given period of time not necessarily equal to the period of time in which the priming component was delivered. I an illustrated embodiment, composite signal 70 may be formed from a sinusoidal priming component at 1,200 Hz delivered for 1 ms followed by a sinusoidal tonic component at 180 Hz delivered for 2 ms. Utilizing the user interface described herein, the user may be able to control the frequency, amplitude and duration of each priming signal and tonic signal component as described herein.

Figure 8:
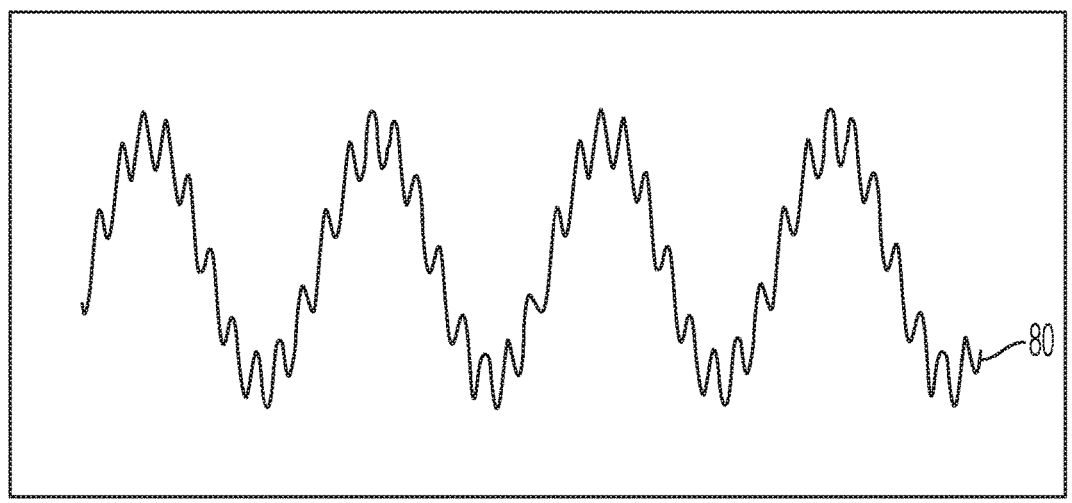
FIG. 8 illustrates conceptually a frequency modulated signal, with a carrier frequency smaller than the modulating frequency, that may be utilized for multimodal modulation in accordance with an embodiment of the present disclosure.

FIG. 8 illustrates conceptually a double sinusoidal composite signal 80 in which the priming component is of lower amplitude and convoluted into the tonic component. In an illustrated embodiment, composite signal 80 may be formed from a sinusoidal tonic component at 100 Hz, and a sinusoidal priming component at 1,200 Hz, with the tonic component having an amplitude that is eight times the amplitude of the priming component. Utilizing the user interface described herein, the user may be able to control the frequency, amplitude and phase shift of each component as described herein.

Figure 9:
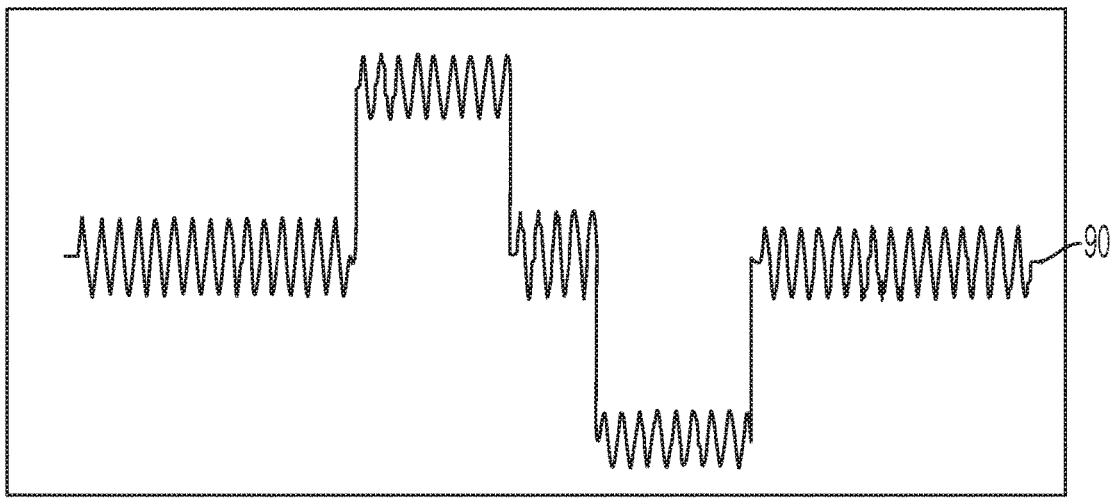
FIG. 9 illustrates conceptually a composite signal, biphasic pulse example, that may be utilized for multimodal modulation in accordance with an embodiment of the present disclosure.

FIG. 9 illustrates conceptually a composite signal 90 made of two biphasic rectangular signals. The priming component is of lower amplitude than the tonic component and is convoluted with the tonic signal. In an illustrated embodiment, composite signal 90 may be formed from a priming signal at 10,000 Hz and 50 µs PW convoluted in a 250 Hz biphasic rectangular signal with a 900 µs PW, with the tonic component having an amplitude that is ten times the amplitude of the priming component. Utilizing the user interface described herein, the user may be user will be able to control the frequency, amplitude and phase shift of each component as described herein.

Figure 10:
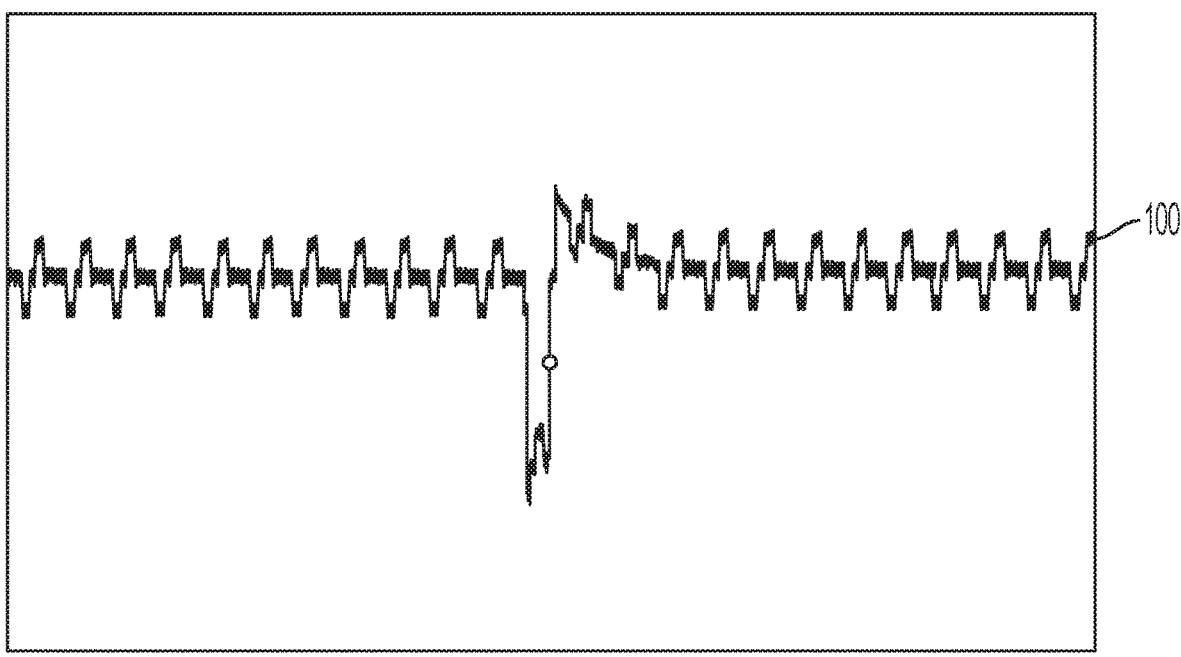
FIG. 10 illustrates conceptually a composite signal with a rectangular biphasic priming component and an asymmetric biphasic tonic component that may be utilized for multimodal modulation in accordance with an embodiment of the present disclosure.

FIG. 10 illustrates conceptually a composite signal 100 made of two biphasic rectangular signals. The priming component is of lower amplitude than the tonic component and is convoluted with the tonic signal. In an illustrated embodiment, composite signal 100 may be formed from a priming signal at 1,200 Hz and 150 µs PW convoluted in a 50 Hz biphasic asymmetric rectangular/exponential decay signal with a 400 µs PW, with the tonic component having an amplitude that is five times the amplitude of the priming component. Utilizing the user interface described herein, the user may be able to control the frequency, amplitude and phase shift of each component as described herein.

Figure 11:
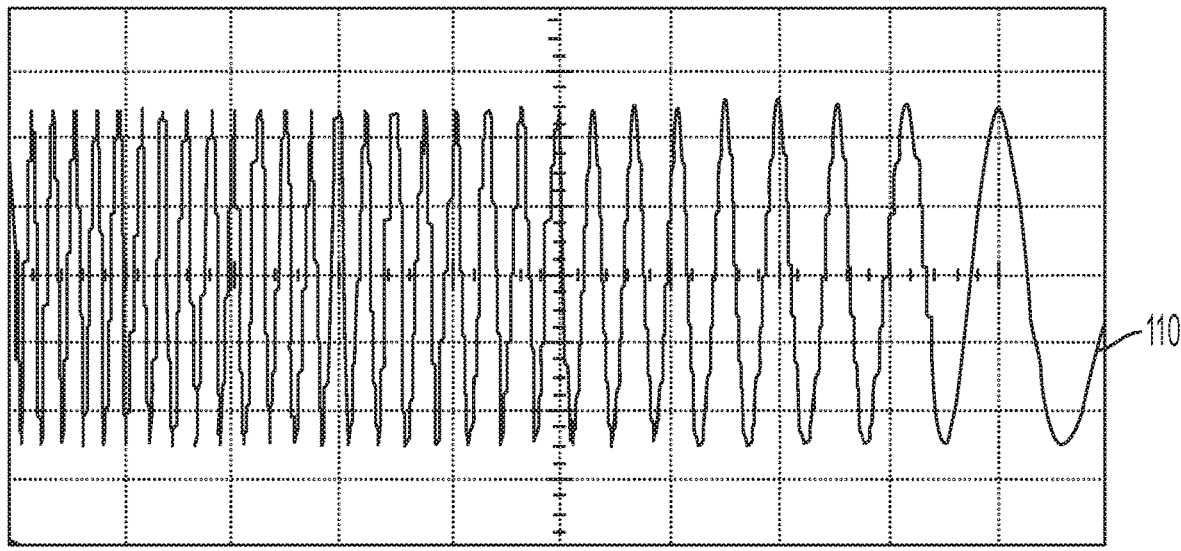
FIG. 11 illustrates conceptually a composite signal with a continually changing frequency that may be utilized for multimodal modulation in accordance with an embodiment of the present disclosure.

FIG. 11 illustrates conceptually a frequency changing composite signal 110 in which the priming component is delivered initially at a frequency larger than the tonic component and then decreases for a given time to the tonic component frequency before a new signal cycle is started. An example may comprise a starting priming frequency of 1,000 Hz, which is rolled down to a tonic frequency of 200 Hz within a 50 ms period, while the amplitude is kept constant. In an illustrated embodiment, composite signal 110 may be formed from a linear or non-linear change in amplitude, as the signal is rolled down from the priming frequency into the tonic frequency. Utilizing the user interface described herein, the user may be able to control the frequency, amplitude and of each component and the roll down time as described herein.

Figure 12:
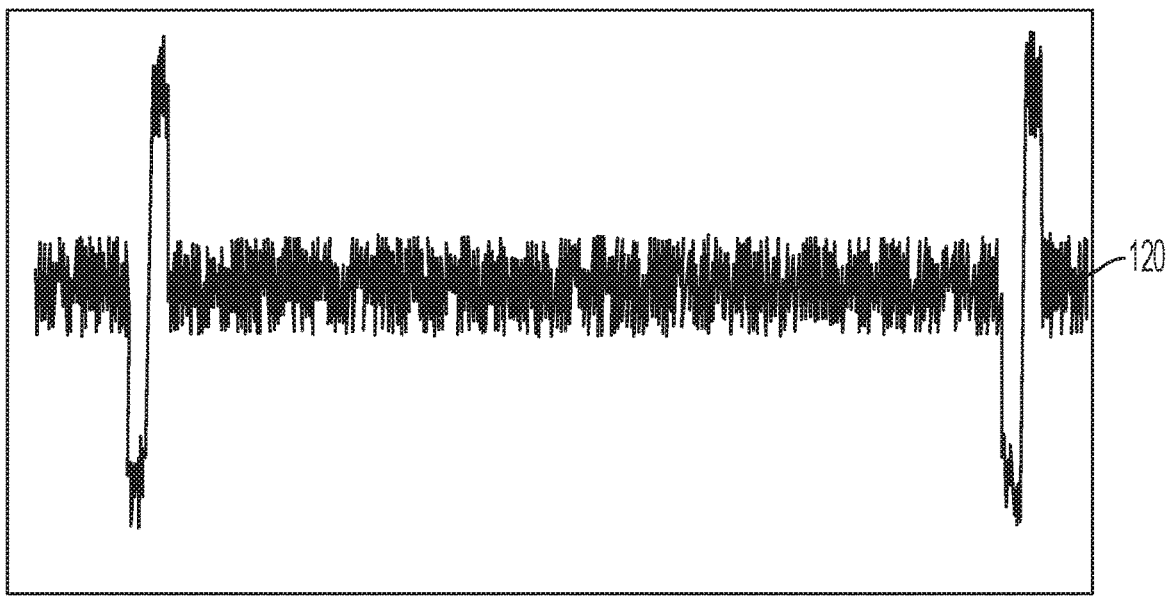
FIG. 12 illustrates conceptually a composite signal with a white noise priming component summed to a symmetric biphasic tonic component that may be utilized for multimodal modulation in accordance with an embodiment of the present disclosure.

FIG. 12 illustrates conceptually a composite signal 120 in which the priming component is noise and is convoluted with a biphasic symmetric rectangular tonic component. In an illustrated embodiment, composite signal 110 may be formed from a noise amplitude equivalent to one third of the tonic component amplitude with a tonic frequency of 100 Hz and 200 µs PW. The tonic component may be delivered randomly and non-linearly within a 10-500 Hz range in order to create a stochastic resonance effect. In embodiments utilizing stochastic resonance for the tonic component, a pseudorandom signal generation technique may be required. For example, randomization can be obtained with a series of Zener diodes and transistors to create a pseudorandom signal which is based on the random movement of electrons through the circuit.

In some embodiments, randomization can be obtained out of the harmonic oscillations of a quartz oscillator and a timing circuit set to various pseudorandom counting parameters. In other embodiments, a Peltier-based thermocouple can be used to generate randomization based on the thermal noise of the body of the patient. Those skilled in the art will appreciate that many other digital or analog circuit-based configurations may be utilized for achieving random numbers. Once obtained, random numbers may be used to generate a digital high or low signal, creating a random series of tonic pulses for application to the neural tissue. Such randomization circuits can also be used to generate noise that approximates true white noise, pink noise, blue noise, brown noise, gray noise, or any other distributions of energy within the frequency spectrum.

Utilizing the user interface described herein, the user will be able to control the frequency, amplitude and phase shift of each component as described herein.

In accordance with an embodiment of the present disclosure, the central processor module 25 of multimodal generator 20 may access stored numeric data mathematically describing wave shapes for one or more signals and may generate from such data step functions emulating signals at different frequencies. The processor performs algorithmic manipulation of such data to achieve the desired signal processing results. Digital to analog converters associated with the central processing module 25 may convert the processed signal into a single output having the correct amplitude for coupling to one or both electrodes 30 and 32. In this manner, the interactive effects of two separate signals may be achieved with a single electrical composite signal capable of stimulating/modulating the interaction between glial cells and neurons in a manner which emulates the use of two separate signals.

In composite signals emulating a frequency modulated prime multimodal modulation signal, either constituent signal component, e.g., the priming signal or the tonic signal, may function as the program or carrier signals in a frequency modulation algorithm. For example, a frequency modulated multimodal signal can have a carrier frequency larger (e.g., 1,000 Hz) than the modulating frequency (e.g., 50 Hz) resulting in a stimulating signal, as illustrated in FIG. 7. In another example, a frequency modulated multimodal signal can have a carrier frequency smaller (e.g., 50 Hz) than the modulating frequency (e.g., 1,000 Hz) resulting in a stimulating signal as illustrated in FIG. 8. In these embodiments, the tonic component may be delivered randomly and non-linearly within a 10-500 Hz range in order to create a stochastic resonance effect as described herein.

Figure 13:
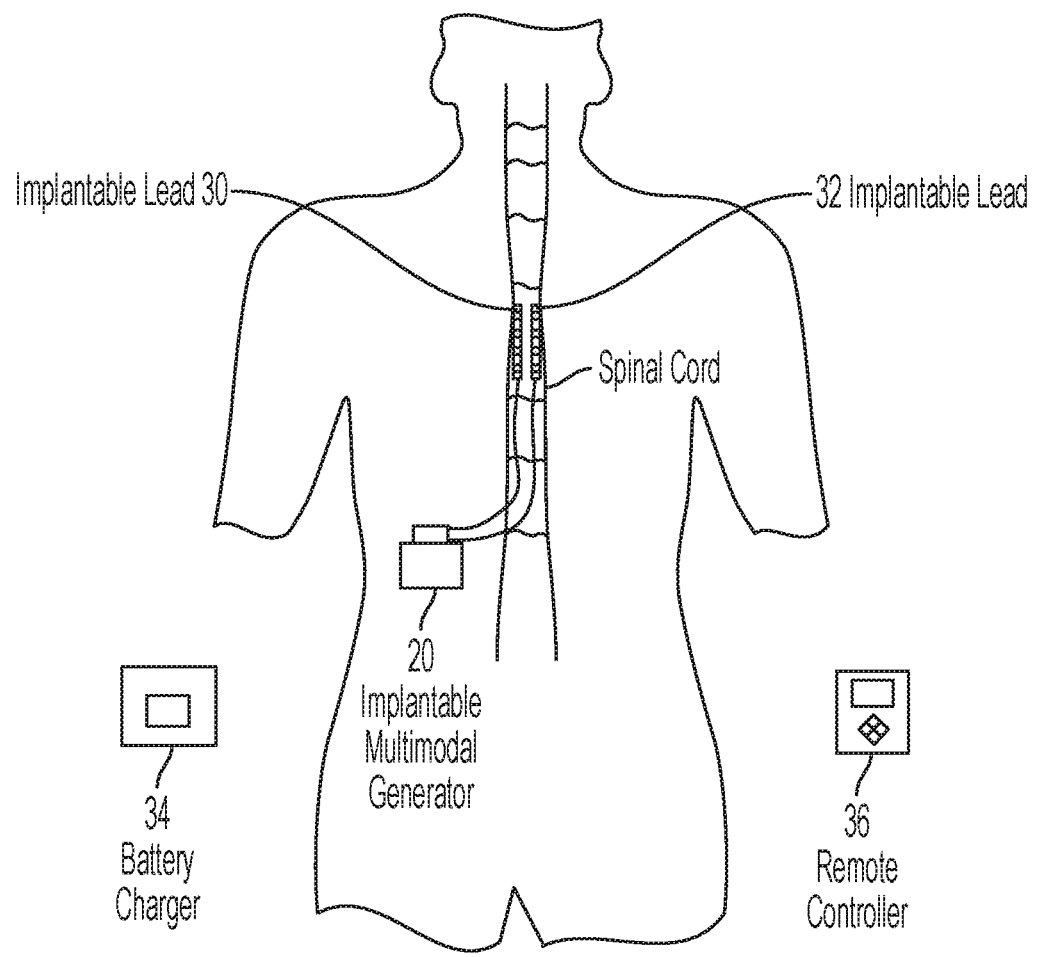
FIG. 13 illustrates conceptually the placement of an implantable system with a human subject in accordance with an embodiment of the present disclosure.

FIG. 13 illustrates conceptually another embodiment of an implantable system with a human subject in prone position. Shown is an example of an implantable system in which both leads 30 and 32 are positioned above the dorsal spinal cord at a particular vertebral level. A programmable implantable multimodal generator (IMG) 20 is attached to the leads using conductive cables and is powered by a rechargeable or non-rechargeable long-life battery contained within the Power Source module 21, within the implantable multimodal generator 20. An external battery charger 34 may be used for recharging of the generator using inductive, i.e., wireless, charging. A wireless remote control 36, which may be implemented with any number of wireless communication protocols, including Bluetooth or others, may be used to communicate with IMG 20 to enable a patient's adjustment of parameters at the discretion of the physician. The system may be programmed using an external programmer unit, such as a computer (not shown) that can transmit information to the IMG 20 via wireless communication protocols.

FIG. 14 illustrates conceptually another embodiment of an implantable system with a human subject in prone position. Shown is an example of an implantable system, similar to that illustrated with reference to FIG. 13 herein, in which leads are positioned in the neighborhood of a peripheral nerve.

According to still another aspect of the disclosure, a method for managing pain in a subject comprises activating glial cells by multimodal electromagnetic stimulation regulating any of genes for calcium binding proteins, cytokines, cell adhesion or specific immune response proteins, and administering a pharmacological substance to the subject systemically, epidurally, or intrathecally during a time period. In other embodiments, such a pharmacological substance may be injected through the stimulation lead, which may have a port to deliver the pharmacological agent directly into the epidural or intrathecal space. Optionally, the pharmacological agent may be impregnated onto the stimulation lead using a slow release formulation in order to provide a slow elution of the pharmacological substance into the neural tissue around the lead.

A pharmacological substance suitable for use with the disclosed method may comprise a metabotropic or ionotropic glutamate receptor antagonist such as (S)-4-carboxyphenylglycine (CPG), (RS)-a-methyl-4-carboxyphenylglycine (MCPG), or kynurenic acid (KYA). In another embodiment, a suitable pharmacological substance may comprise a potassium channel antagonist, such as 4-aminopyridine (4AP), or an alpha-2 adrenergic receptor agonist, such as clonidine, or a calcium channel agonist such as the w-conotoxin MV11C, a NMDA receptor agonist such as ketamine or glial cell modulators like alendronate, cyclosporine A, cannabinoid receptor agonist (CB1R or CB2R) or monoclonal antibodies against at least cytokines such as tumor necrosis factor alpha, Interleukin 1 or 6, etc., or fusion proteins like etanercept, or abatacept. Such pharmacological substances can help to activate or deactivate glial cells by modulating the release of glutamate, potassium or calcium ions in or out the glial cell.

In one embodiment, activating the glial cells comprises exposing the glial cells to a stimulus, which is a composite electromagnetic field. The multimodal signal resulting from a single, dual or multiple simultaneously applied electromagnetic fields may promote targeted delivery of the administered pharmacological agents by decreasing their resistance to penetrate tissue, while providing an electrical force that steers the pharmacological compounds towards the target neural tissue according to the electric properties (polarity, polarizability) of such pharmacological agent (iontophoretic effect). The stimulation characteristics of the priming component of the multimodal signal may decrease the tissue resistance so the pharmacological substance may penetrate better into the target neural tissue. Additionally, the polarity of the multimodal electric fields may be optimized to steer the pharmacological substance to the aforementioned target neural tissue.

EXAMPLE 1

Figure 15:
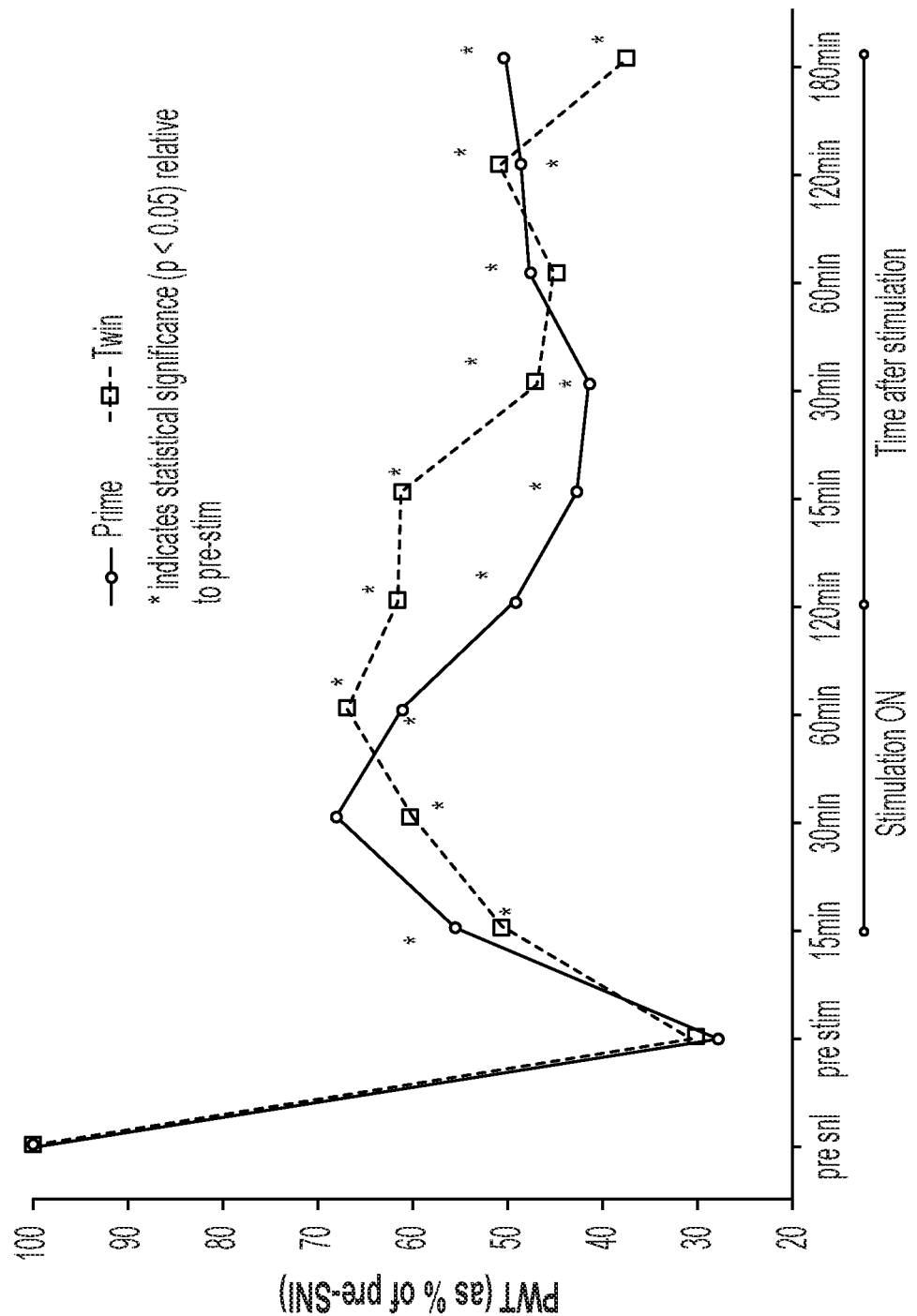
FIG. 15 illustrates conceptually a graph of results achieved in a pre-clinical animal study utilizing systems and methods in accordance with the present disclosure.

Referring to FIG. 15, an initial pilot study using an animal model for neuropathic chronic pain was carried out (n=29). In this study, a peripheral nerve injury was surgically induced by transecting the tibial and peroneal branches of the sciatic nerve at the point of trifurcation while sparing the sural nerve (spared nerve injury, SNI, model). After four days of transection, the subject develops mechanical and thermal hypersensitivity (allodynia), which is considered pain-like behavior. Subjects were implanted with a small cylindrical four-contact lead fitted surgically into their epidural space at the vertebral level corresponding to the innervation of the sciatic nerve. At day four post-surgery subjects were behaviorally tested using von Frey filaments. These filaments of different tensile strength are used to measure the sensitivity of a skin area affected by the nerve injury to mechanical stimulation. In the SNI model, the plantar area of the hind paw ipsilateral to injury becomes hypersensitive. A hypersensitive subject will withdraw its paw upon stimulation with a filament of very low tensile strength. Mechanical hypersensitivity was evident in the ipsilateral hind paw in comparison to the contralateral one, which was used as a normal behavior control.

In a particular example of multimodal stimulation, electrodes implanted in the epidural space of the rat above the dorsal aspect of the spinal cord were connected to a current source delivering a priming signal that consisted of a charge-balanced biphasic symmetric rectangular pulse oscillating at 1,200 Hz and a PW of 30 μs at an amplitude of 0.1 mA (33% motor threshold, MT). The was combined with a tonic signal which was a charged balanced biphasic symmetric rectangular pulse oscillating at 50 Hz, PW of 50 μs and amplitude of 0.2 mA (66% MT). Electrical stimulation was continuously applied for two hours and behavioral testing for mechanical sensitivity was performed every fifteen minutes while the subject was being stimulated. Behavioral testing was continued every fifteen minutes after stimulation was turned off for one hour and then every hour until three hours post stimulation. FIG. 16 shows the results as an average of the various recordings obtained from Behavioral data indicates that multimodal stimulation improves mechanical allodynia after fifteen minutes of stimulation with the improvement lasting for more than one hour after the stimulation is turned off, indicating that there is a residual effect of the applied fields, which suggest modulation of the nervous system.

EXAMPLE 2

In the example, the genome-wide expression effects in ipsilateral dorsal spinal cord (DC) tissues of spinal cord stimulation (administered for 72 h) were assessed in rats induced with chronic neuropathic pain after peripheral nerve injury. Specifically, in the example genome-wide expression levels were compared between animals of one the most commonly used rodent models for chronic neuropathic pain (spare nerve injury, SNI) upon continuous SCS and sham-treated animals, i.e., animals in which the pain model was induced, and were implanted, but not stimulated.

The genome-wide expression profiling microarray commercially available for the laboratory rat employed in the current studies was capable of surveying the expression of about 21,000 genes. Enrichment analysis based on clustering statistics (using weighted gene correlation network analysis (WGCNA)) allowed for the identification of modules (or subsets) that contained genes that were highly correlated to each other in terms of biological role. Gene ontology analysis allowed for the grouping of genes within a module in terms of more specific biological processes and molecular functionality. Further refinement allowed for the identification of key genes within a particular pathway.

It was found by comparison of the genome of the treated animals that SCS upregulated and down-regulated genes associated with various interrelated processes, as described herein.

Comparative Genomics at the Spinal Cord

Because stimulation was performed atop the dorsal region of the spinal cord, cells of the dorsal spinal cord were examined for expression differences that would indicate the role of genes on molecular functionality and biological functions in this tissue. WGCNA identified that SCS significantly upregulated genes involved in activation of the immune system (false discovery rate (FDR) adjusted P-value=0.016); while genes involved in phosphorylation and activities related to transmembrane transport (FDR P-value=0.011) were down-regulated, as were genes associated with regulation of neuronal activity including regeneration and development. Refinement of the data identified 52 key genes. Among these, the following were identified as particularly noteworthy, since they have been described as involved in the processes of glial activation, immune response and neuronal activity:

Calcium binding protein (Cabp1): This gene was identified as significantly down-regulated (i.e., reduced by 1.4-fold to 1.5-fold) by SCS. The encoded Calcium-binding protein 1 regulates calcium-dependent activity of inositol 1,4,5-triphosphate (ITP) receptors. ITP receptors are involved in the signaling between astrocytes via calcium waves, which have been posited to play a key role in the intercellular communication that propagates astrocyte activation. Down regulation of Cabp1 likely diminishes the activation of astrocytes that is otherwise conducive to the synaptic reshaping that results in a chronic pain state.

Toll-like receptor 2 (Tlr2): This gene was identified as significantly upregulated (i.e., increased by 2.4-fold to 2.8-fold) by SCS. Tlr2 is expressed in activated glial cells, including microglia and astrocytes; however, expression in activated microglia is larger than expression in astrocytes. The encoded Toll-like receptor 2 protein induces a cascade of events that likely leads to the secretion of anti-inflammatory cytokines, such as IL-10.

Chemokine Cxcl16: This gene was identified as significantly upregulated (i.e., increased by 2.2-fold to 3.6-fold) by SCS. This is a transmembrane chemokine which drives the interplay between glial cells and neurons as a result of stimulus. Cxcl16 is expressed by microglia and astrocytes as a neuroprotective agent. Up-regulation of this gene by SCS is indicative of a neuroprotective process in the spinal cord likely involving the modulation of microglia.

Glial maturation factor (Gmfg): This gene was identified as significantly upregulated (i.e., increased by 2.1-fold to 2.3-fold) by SCS. This gene has been thought to be involved in glial differentiation and neural regeneration. There is not much known about this gene. Its upregulation by SCS may be associated with glial activation processes that may lead to neuronal regeneration.

Other key genes identified as upregulated or down-regulated by spinal cord stimulation are described with reference to Table 2 below:

TABLE 2

| Process | Gene | Description | Notes |
|---|---|---|---|
| | | Selected Genes up-regulated by SCS | |
| Inflammation and Immune Response | Ly86 | lymphocyte antigen 86 (2.5-fold to 2.6-fold) | Cooperate with toll like receptor to mediate the innate immune response |
| | Cd68 | Cd68 molecule (2.7-fold to 2.8-fold) | Phagocytic activities of tissue macrophages |
| | Apbb1ip | amyloid beta (A4) precursor protein (1.7-fold to 1.8-fold) | Signal transduction from Ras activation to actin cytoskeletal remodeling |
| | Casp1 | caspase 1 (1.8-fold to 1.9- fold) | Cleaves IL-1 beta |
| | Ifi30 | interferon gamma inducible (2.2-fold to 2.3-fold) | MHC class II-restricted antigen processing |
| | Cd53 | Cd53 molecule (2.2-fold to 2.3-fold) | Mediate regulation of cell development, activation, growth and motility |
| | Tnfaip8l2 | tumor necrosis factor, alpha-induced protein (2.2- fold to 2.3-fold) | Regulator of innate and adaptive immunity by maintaining immune homeostasis |
| | Il1b | interleukin 1 beta (3.7-fold to 3.8-fold) | Mediator of the inflammatory response. Induces cyclooxygenase-2 (COX2) to contribute to inflammatory pain. |
| | Cxcl17 | chemokine (C-X-C motif) ligand 17 (2.1-fold to 2.2- fold) | May be a chemokine regulating recruitment of monocytes and immature dendritic cells |
| | Itgb2 | integrin, beta 2 (1.9-fold to 2.0-fold) | Participate in cell adhesion as well as cell-surface mediated signaling |
| | Timp1 | TIMP metallopeptidase inhibitor 1 (2.9-fold to 3.0- fold) | Inhibitors of the matrix metalloproteinases, involved in degradation of the extracellular matrix |
| | Tnfsf12 | Tumor Necrosis Factor (Ligand) Superfamily (1.2-fold to 1.3-fold) | Cytokine that belongs to the tumor necrosis factor (TNF) ligand family. It can induce apoptosis via multiple pathways of cell death in a cell type-specific manner. |
| | Il2rg | Interleukin 2 Receptor, Gamma (1.3-fold to 1.4-fold) | Common subunit for the receptors for a variety of interleukins |
| | | Selected genes down-regulated by SCS | |
| Ion channel regulation | Wwp1 | WW domain containing E3 ubiquitin protein ligase 1 (1.3-fold to 1.4-fold) | Ubiquitinates and promotes degradation of SMAD2 in response to TGF-beta signaling |
| | Micu3 | Mitochondrial calcium uptake family (1.4-fold to 1.5-fold) | Essential regulator of mitochondrial calcium uptake under basal conditions |
| | Grin2a | Glutamate receptor, ionotropic, N-methyl D-aspartate 2A (1.4-fold to 1.5-fold) | Receptor activation requires binding of glutamate and glycine, leads to an influx of calcium into postsynaptic region activating pathways. NMDA receptors have a critical role in excitatory synaptic transmission and plasticity in the CNS. |
| Binding and metabolic pathways | Amph | Amphiphysin (1.4-fold to 1.5-fold) | Associated with the cytoplasmic surface of synaptic vesicles |
| | Gabrg1 Gabra2 | Gamma-Aminobutyric Acid (GABA) A receptor, Gamma 1 (1.5-fold to 1.6- fold) Gamma-Aminobutyric | Protein encoded by this gene is an integral membrane protein and inhibits neurotransmission by binding to the |

TABLE 2-continued

| Process | Gene | Description | Notes |
|---|---|---|---|
| | | Acid (GABA) A Receptor, Alpha 2 (1.4-fold to 1.5-fold) | benzodiazepine receptor and opening an integral chloride channel |
| | Gria3 | Glutamate receptor, ionotropic, AMPA 3 (1.3-fold to 1.4-fold) | Receptor for gluta mate, functions as ligand-gated ion channel in the CNS, plays an important role in excitatory synaptic transmission |
| Cell growth | Knca1 | Potassium Voltage-Gated Channel, Shaker-Related Subfamily (1.3-fold to 1.4- fold) | Mediates the voltage-dependent potassium ion permeability of excitable membranes |
| | Kifc3 | Kinesin Family Member C3 (1.2-fold to 1.3-fold) | Molecular motor that use ATP hydrolysis to translocate cargoes along microtubules |
| ATP related, transmembrane/ transporter activity | Igsf1 | Immunoglobulin Superfamily (1.9-fold to 2.0- fold) | Thought to participate in the regulation of interactions between cells |
| Cell regulation | Oprm1 | Opioid Receptor, Mu 1 (1.3- fold to 1.4-fold) | Principal target of endogenous opioid peptides and opioid analgesic agents such as beta-endorphin and enkephalins. |

For the above-referenced genes, it is contemplated that expression level changes of any magnitude deemed statistically significant can be predictive of outcome (e.g., a biphasic signal can be manipulated for sufficient duration to produce a statistically significant change in the expression of one or more such genes within the modulated glial cells, as indicative of SCS having achieved a desired effect upon a subject). Statistically significant levels of up-regulation can include at least 1.2-fold, at least 1.3-fold, at least 1.4-fold, at least 1.5-fold, at least 1.6-fold, at least 1.7-fold, at least 1.8-fold, at least 1-9-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4-fold, at least 5-fold, etc. in an assayed cell, population and/or tissue(s), as compared to an appropriate control (e.g., control cell(s), tissue and/or value). Similarly, statistically significant levels of down-regulation can include at least 1.2-fold, at least 1.3-fold, at least 1.4-fold, at least 1.5-fold, at least 1.6-fold, at least 1.7-fold, at least 1.8-fold, at least 1-9-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4-fold, at least 5-fold, etc. in an assayed cell, population and/or tissue(s), as compared to an appropriate control (e.g., control cell(s), tissue and/or value).

Many of the genes involved in the inflammatory and immune response are associated with glial activity. Peripheral nerve injury is accompanied by regulation of genes and proteins not only at the site of injury, but also in the afferent ipsilateral CNS structures such as the DRG and the spinal cord. Proteomic analysis was recently performed in the spinal cord and DRG of the SNI animal model for neuropathic pain. This study indicated that transport and translocation of proteins was observed along the axon towards the soma, and then reciprocal protein transport back to the periphery to induce axon regeneration. Interestingly, the spinal cord presented with neuroprotective proteins, some associated with glial cell activation. The activation of glial cells following injury induced a cascade of events including an inflammatory and immune response, which then developed into peripheral sensitization that was conducive to ectopic firing of neurons. The alarm eventually extended to the CNS at the level of the spinal cord, where the microglia apparently attempted to protect the integrity of the system. Eventually, glial cells overreacted and induced the release of factors that reshaped the synapses. These changes in the synaptic plasticity manifested as chronic pain.

The results indicate that electrical stimulation of the spinal cord elicited regulation of genes and proteins that modulate the interactions between glial cells and neurons. It is plausible that these molecular events produce analgesia.

EXAMPLE 3

The effect of phase polarity upon the modulation of genes previously presented was carried out using an animal model of chronic neuropathic pain. In this example, tissues from the spinal cord were obtained from animals, which were stimulated using a rectangular waveform at a frequency of 50 Hz and a pulse width of 200 μs per phase which were either monophasic cathodic, monophasic anodic, or symmetric biphasic with an initial cathodic polarity. RNA from tissues was extracted and cDNA was prepared by reverse transcription. RNA expression levels were assessed using real-time PCR, with levels quantified and standardized. Based on the above experiments (example 2), a panel of genes including markers for glial activation (tlr2, cxcl16), calcium-dependent glial processes (Cabp1), immune system activation (cd68), and an opioid receptor (oprm1) was selected for analysis.

FIGS. 17A-17E illustrate conceptually graphs of observed expression levels of selected genes relative to the polarity of the phase used in the stimulation waveform, including a) Calcium binding protein (Cabp1); b) Chemokine (Cxcl16);

c) Toll-like receptor 2 (Tlr2); d) Cd68 molecule; and e) Opioid receptor mu-1 (Oprm1). It was evident that the polarity of the signal phase influenced regulation of these genes. Biphasic stimulation increased the levels of genes associated with glial activation (Tlr2 and Cxcl16) relative to anodic and cathodic stimulation in response to the release of glutamate from astrocytes. Biphasic stimulation increased the levels of Cabp1 relative to monophasic stimulation (cathodic or anodic). Monophasic stimulation (cathodic or anodic) and biphasic stimulation both produced similar levels of the immune-related gene Cd68, as well as the gene encoding for the opioid receptor, Oprm1.

EXAMPLE 4

The subject patient was a 65 y/o female patient with diagnosis of Diabetic Neuropathy Syndrome complaining of severe bilateral pain in the lower extremities all the way to the feet. Patient had failed multiple medical treatments including physical therapy, medication management and surgical intervention.

The patient underwent a spinal cord stimulator trial with a high frequency paresthesia-free based SCS system. Two leads were positioned in the posterior epidural space with the tip of one of the leads located at the top of T8 and the other at the tip of T9. Patient returned seven days later for conclusion of the trial with high frequency paresthesia-free SCS, the patient reported only 30% pain relief.

At this point, the multimodal stimulation system of the present disclosure was applied. The system was reprogrammed using two external generators to generate a composite signal in the neural tissue. One generator was set for tonic at 50 Hz, 400 µs PW. The other was set for priming at either 900 or 1,200 Hz, 150 µs PW. The amplitude of the 50 Hz signal was initially set at 0.6 mA and the amplitude of the 900 Hz signal was initially set at 2.2 mA before the patient went home. These amplitudes did not induce paresthesia during treatment. Patient reported 57% pain relief in the legs after 20 hours of therapy.

Patient was reprogrammed to receive a priming frequency of 1,200 Hz. After reprogramming, patient continued experiencing pain relief without tingling. More important, pain relief was increased to 71% after 54 hours of reprogramming.

In summary of trial:
1. Subject patient did not experience paresthesia during the four days of treatment.
2. Patient reported that the paresthesia-free Multimodal treatment was superior to high frequency stimulation treatment.
3. Patient reported 71% of pain relief in her legs and feet.
4. Sharp pain in legs was significantly reduced.
5. Burning sensation in the feet was alleviated which allowed patients to endure longer walks than before therapy.

EXAMPLE 5

The subject patient was a 76 y/o female diagnosed with failed back surgery syndrome. Patient has suffered from chronic pain in the lower back and legs. Subject has been treated with conventional treatments without clinical success. Pain numerical rate score before treatment was reported as 8, with pain in the back radiating to the legs. A pair of SCS trial leads were implanted using a non-parallel alignment (i.e., they were offset from each other), and a high frequency paresthesia-free program had been set. Patient reported total pain relief in the back and legs leg from the high frequency treatment. Patient reported improvement in sleep and a decrease of Vicodin ingestion. Patient was then reprogrammed using multimodal stimulation with priming parameters set at 1,200 Hz, 150 µs PW and 3 mA, while tonic parameters were set at 50 Hz, 400 µs PW and 4.9 mA.

Patient experience very little pain (0-1 in a 0-10 numerical rating scale) in back and legs during the following days under multimodal therapy.

Patient reported also that she was able to increase her activity and could climb up and down stairs (an activity she avoided before SCS treatment). Family was impressed with improvements in daily activity since being under therapy trial period.

In summary:
1. Patient did not experience paresthesia during three days multimodal SCS therapy.
2. Patient was able to reduce pain medication ingestion.
3. Patient reported minimal back pain and leg pain (mean of 0.5 in the 0-10 numerical scale).
4. Patient reported significant improvement on sleep habits.
5. Patient reported significant increase in her ability to carry out daily activities that she could not do before SCS therapy.

EXAMPLE 6

Figure 16A:
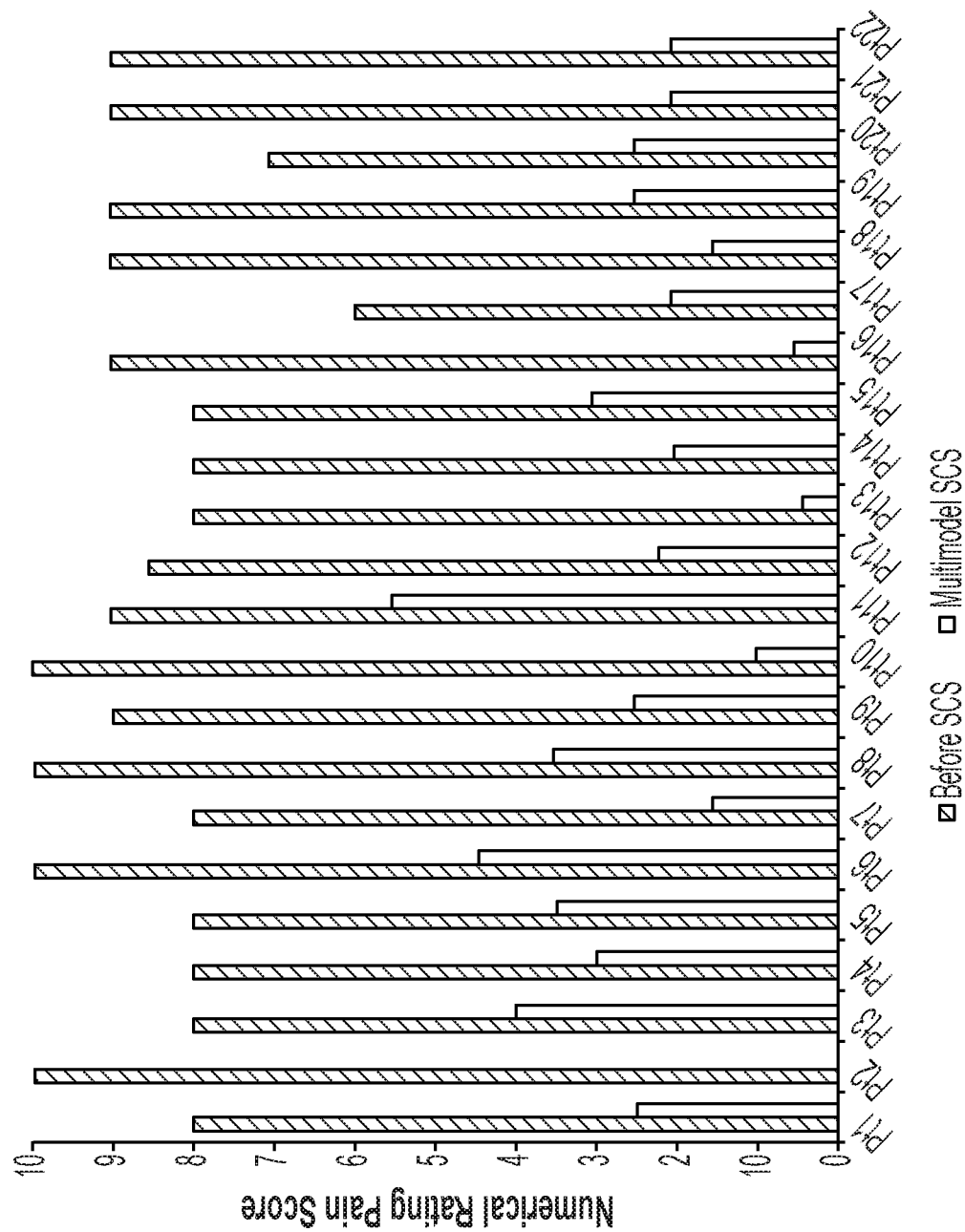
FIGS. 16A and 16B illustrate conceptually graphs of results achieved in a short time pilot clinical trial period utilizing systems and methods in accordance with the present disclosure.
Figure 16B:
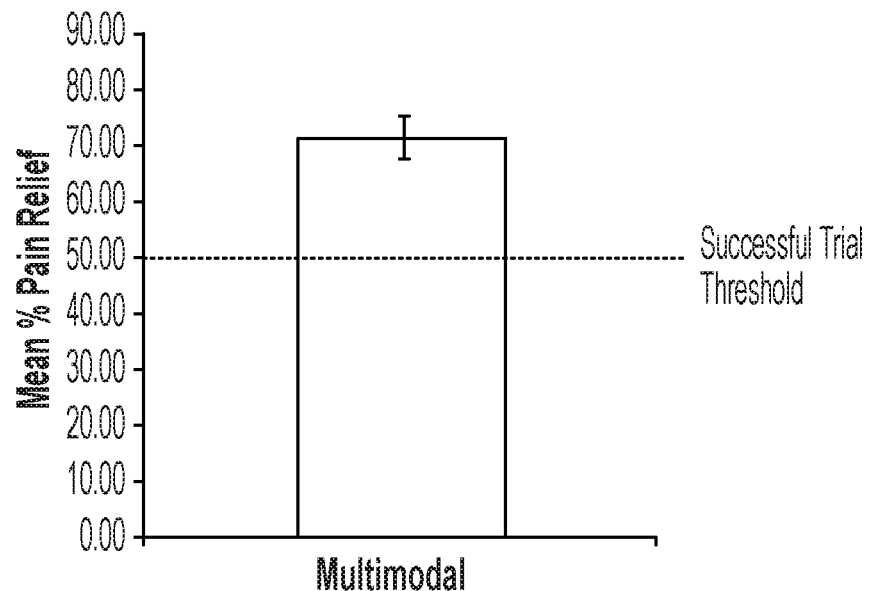
Figure 17A:
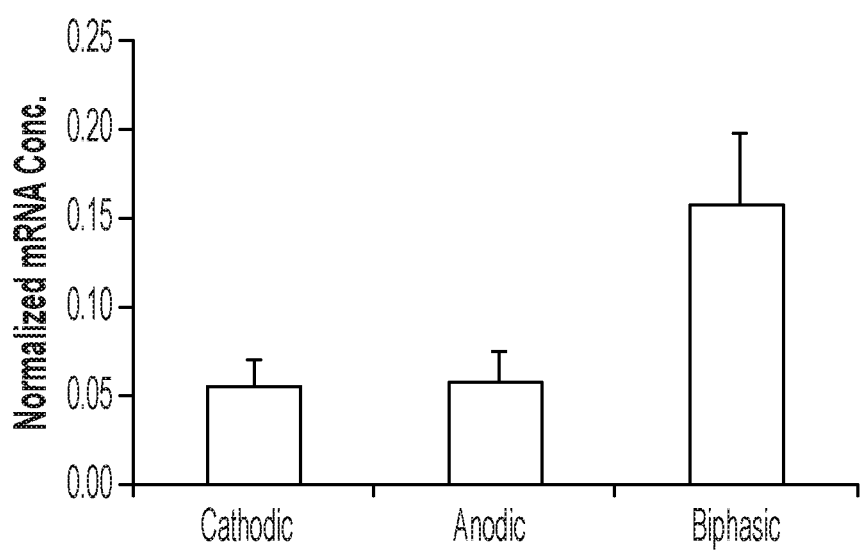
FIGS. 17A-17E illustrate conceptually graphs of experimental results indicating how the polarity of the stimulating electromagnetic field signal influenced gene expression.
Figure 17B:
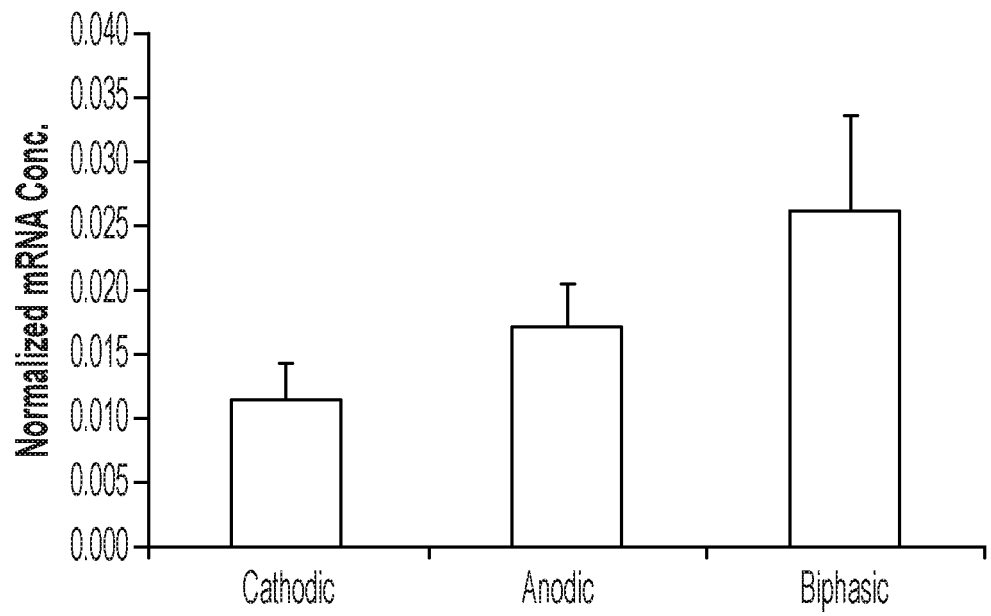
Figure 17C:
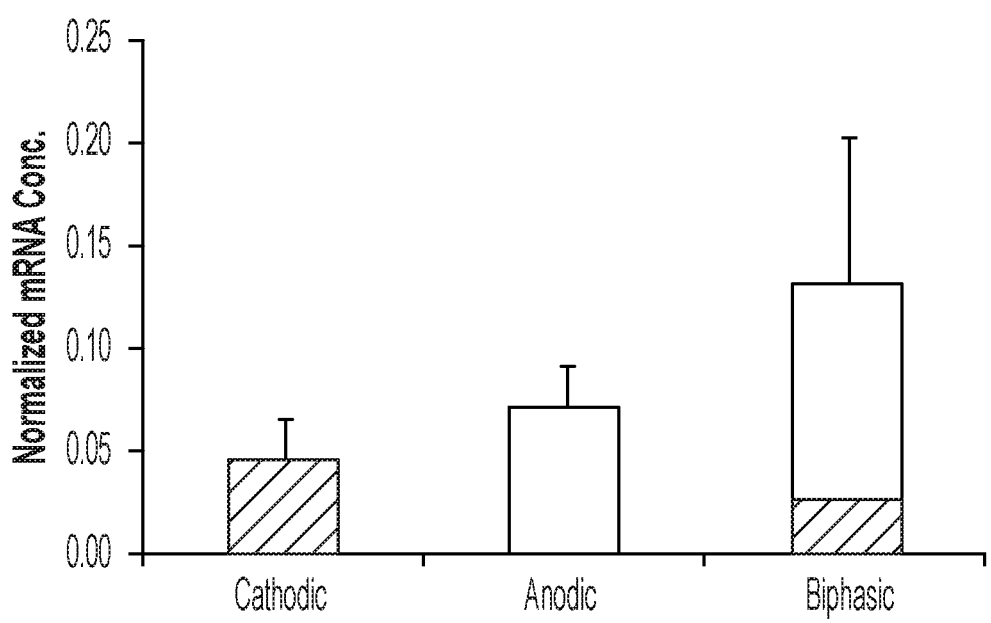
Figure 17D:
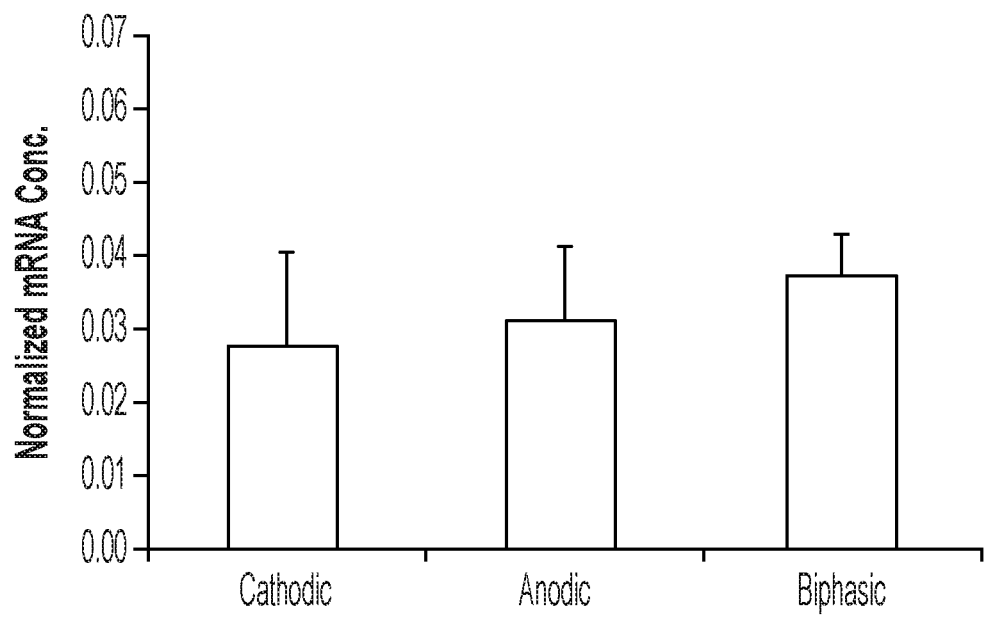
Figure 17E:
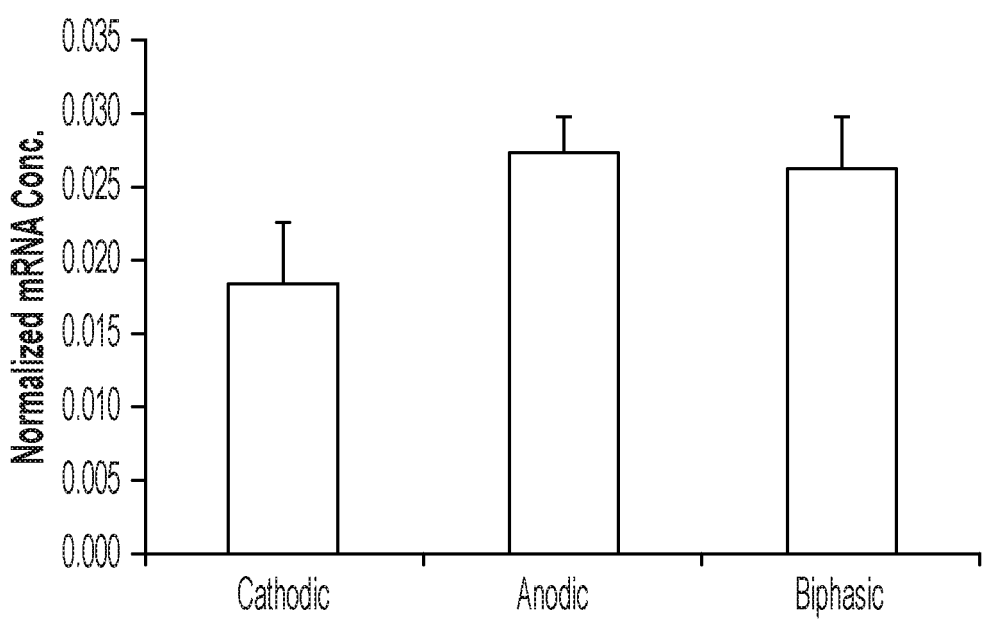

Referring to FIGS. 16A and 16B, an observational study using human volunteers was carried out (n=22). These subjects were part of a trial period for commercial spinal cord stimulation systems administered under standard clinical practice. Subjects voluntarily accepted to try multimodal modulation after they had completed their trial period. Success in a trial period is indicated by pain relief equal or above 50% relative to the pain numerical rating score (NRS) present before the spinal cord stimulation therapy was commenced. All subjects had been implanted with two eight-electrode trial leads. Thirteen of them had leads staggered relative to each other and five of them had leads parallel to each other. Nine of the subjects had trialed conventional paresthesia-based stimulation systems (50-70 Hz) and thirteen of them had trialed a high frequency system (10,000 Hz). Four of the subjects failed the trial with conventional paresthesia-based stimulation (50-70 Hz) and three the high frequency paresthesia-free stimulation (10,000 Hz). Multimodal stimulation was tried for as short as three hours and for as long as four days. All but one of the 22 subjects successfully tried multimodal stimulation under the paresthesia or perception threshold (PT). The mean pain relief of the subjects was 72% and all subjects declared to be satisfied with multimodal stimulation therapy.

Figure 18:
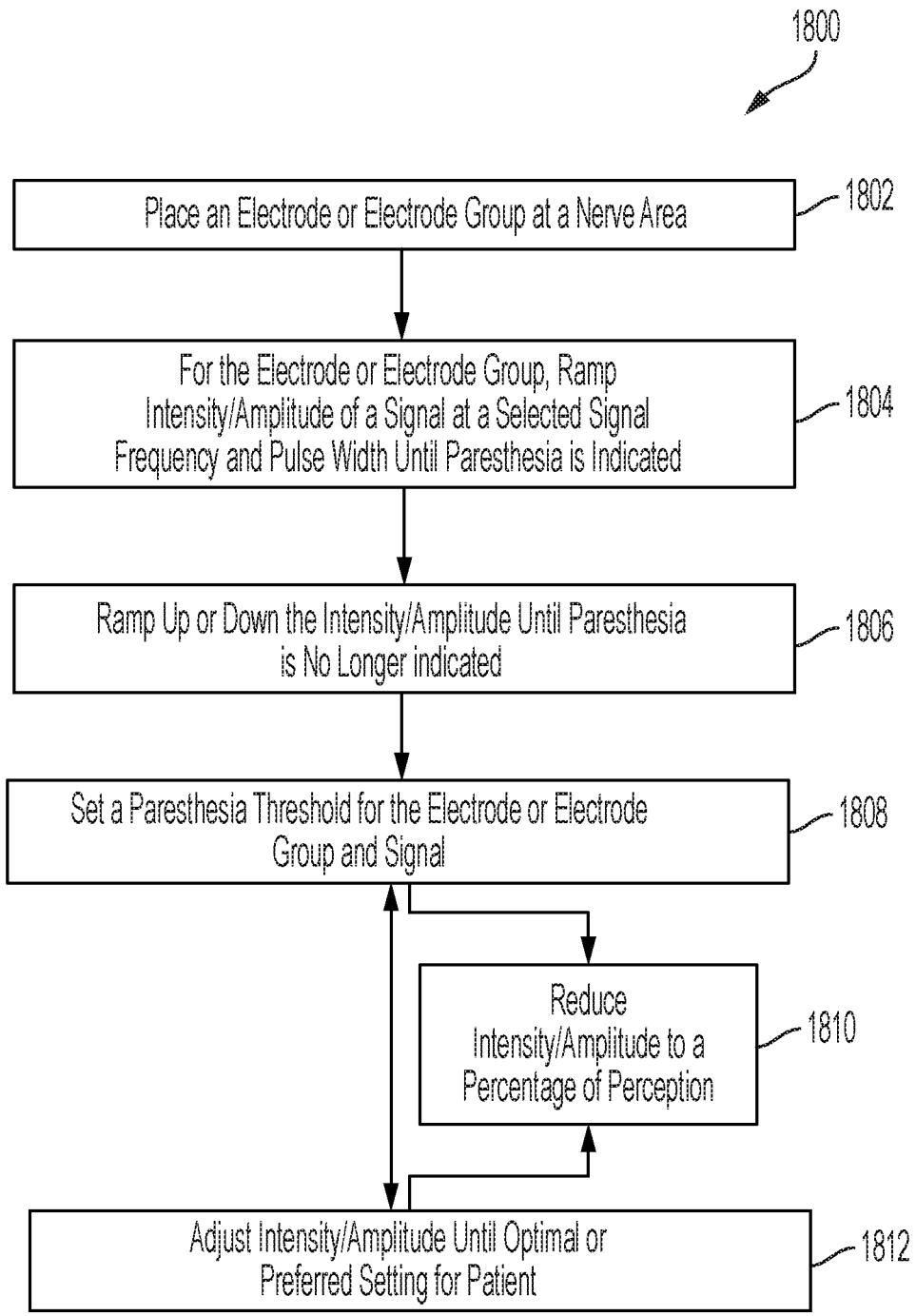
FIG. 18 illustrates an exemplary patient fitting/setup workflow.

Exemplary embodiments describe a variety of patient fitting/setup options. With reference to FIG. 18, a workflow for fitting/setting up a patient is shown generally at 1800 and includes placing an electrode or electrode group at a nerve area (spinal nerves, peripheral nerves, specific areas or clusters, etc.), shown in step 1802. For an electrode or electrode group placed at the nerve area, a signal (which includes a frequency and pulse width), is ramped up in intensity/amplitude until paresthesia is indicated (step 1804). Once paresthesia is indicated, the Intensity is either ramped up or down to the point that paresthesia is no longer indicated. This provides an indication of a paresthesia threshold, which may be stored as a paresthesia threshold. Optionally, a reduction of the intensity/amplitude of the signal may be performed at 1810. At 1812, an adjustment of intensity/amplitude is performed (e.g., incrementally over time) until an optimal or preferred setting is established for a patient.

In exemplary embodiments, in post-operation, a patient program may be set to one of a range of percentages of perception (% TPT or % PPT). In one exemplary embodiment, such range is from 65%-75% perception. Other exemplary embodiments contemplate ranges between 20% and 90%, 30% and 80%, 40% and 80%, 50% and 80%, 60% and 80%, among others. Additionally, % TPT and % PPT may vary, with different percentages between different frequency types or different percentages between electrodes or groups of electrodes according to different positioning or different effect.

In exemplary embodiments, intensity/amplitude of the signals may initially be set to zero, with subsequent increase until the patient indicates the perception threshold, with subsequent reduction to the above-mentioned percentage of PT. Further, in exemplary embodiments, program settings for each electrode or group of electrodes are individually adjustable.

Additionally, in exemplary embodiments, the efficiency of programming can be increased by performing a setup for one pulse on a group of electrodes, followed by copying the program settings (matching settings) or by making certain changes to the program settings (varying settings) before pasting those program settings into other groups of electrodes.

In exemplary embodiments, establishment of perception (TPT or PPT) may also be done separately for each group of electrodes, thereby providing a relevant level for determining the effective level for each of different desired effects (priming and tonic, positional, etc.) or providing a baseline tailored to a specific patient, which can be used to quickly find an optimal or preferred setting for that patient.

Further, reduction of amplitude to a percentage or perception (TPT or PPT), followed by increasing each of groups of electrodes or types of groups (priming vs. stimulation/tonic) can be beneficial because: it can facilitate a beneficial selection from both a pain reduction and power consumption perspective (versus starting at perception and decrementing, which is also considered by the present specification); it recognizes that even though there is a synergy between the different stimulation types (priming and tonic), the combination is additionally effective when amplitudes for each group or type are set independently; and it recognizes that the different stimulation types may be differently felt by the patient, with the patient preferring one over the other.

As has been noted, additional exemplary embodiments include alternate methods for establishing a comfort level for a patient, such as establishing perception and, rather than reducing to a percentage, incrementing up or down to find a comfort level. As before, this may be done for one or more groups and replicated (or replicated in part) or may be done individually without such replication.

A description of an exemplary programming setup procedure, with an exemplary increase in programming efficiency, follows.

EXAMPLE 7

A certain spinal location is selected for assignment of electrodes. For example, an electrode nearest to the middle of T8 and T9 may be designated. For a "Group A", Program 1, the cathode is placed on/assigned to the electrode nearest to the middle of T8. An anode is placed two electrodes below the cathode. The device rate is set to a desired frequency, e.g., 300 Hz; and the program rate is changed to a lower rate than the device rate, e.g., 1/6 device rate, or 50 Hz. Pulse width may be set to a desired width, e.g., 200 microseconds. Program 1 may be closed. For a Program 2 in Group A, the cathode may be placed on the electrode nearest to the middle of T9, with the anode placed two electrodes below the cathode. Some variation of pulse width may be set, e.g., PW=170 microseconds. Program 2 may be closed.

In an exemplary program setup, Group B may be set up the same as for Group A, except for being ½ vertebral segment lower than Group A (and on a second lead). Group B is activated and program 1 selected. Program 1 is activated, with all electrodes selected. The cathode and anode are then slid down one half a vertebral segment lower (with the cathode now on the electrode nearest the top of T9). Program 2 is activated, all electrodes selected; and cathode and anode are slid down one half a vertebral segment lower (with the cathode on the electrode nearest to the T9/T10 disc space. The program is closed.

In a further exemplary "Group C" program setup, the electrode setup is the same as for Group A, except that it is one quarter of a vertebral segment lower than for Group A, again, on the second lead. Group C is activated, selecting program 1. Program 1 is activated, selecting all electrodes. Subsequently, the cathode and anode are slide one quarter of a vertebral segment lower (with the cathode being on the electrode nearest the bottom of T8). Subsequently, Program 2 is activated, with all electrodes selected, the cathode and anode being moved one quarter of a vertebral segment lower (with the cathode on the electrode nearest the bottom of T9). The program is closed.

In exemplary embodiments, for programming amplitudes, for Group A, Program 1 (A1), the intensity in Program 1 is ramped up until paresthesia is felt. Subsequently, it is ramped down in individual increments until the patient loses paresthesia. This is recorded as the LD paresthesia threshold. Intensity is subsequently decreased to a percentage of PT (e.g., 70%) as a final LD amplitude, with stimulation remaining on for Program 1.

Changing to Program 2 in Group A (A2), intensity in Program 2 is ramped up until paresthesia is felt. Subsequently, intensity is ramped down in individual increments until the patient loses paresthesia. The value is recorded as the HD paresthesia threshold. Intensity is decreased to a percentage of PT (e.g., 65%) and recorded as a final HD amplitude. Stimulation for Program 2 is kept on.

For Group A, Program 3 (A3), intensity is increased to that of Group A, Program 2. For Group A, Program 4 (A4), intensity is increased to that of Group A, program 2.

In exemplary embodiments, for programming amplitudes, for Group B, Program 1 (B1), the intensity in Program 1 is ramped up until paresthesia is felt. Subsequently, it is ramped down in individual increments until the patient loses paresthesia. This is recorded as the LD paresthesia threshold. Intensity is subsequently decreased to a percentage of PT (e.g., 70%) as a final LD amplitude, with stimulation remaining on for Program 1.

Changing to Program 2 in Group B (B2), intensity in Program 2 is ramped up until paresthesia is felt. Subsequently, intensity is ramped down in individual increments until the patient loses paresthesia. The value is recorded as the HD paresthesia threshold. Intensity is decreased to a percentage of PT (e.g., 65%) and recorded as a final HD amplitude. Stimulation for Program 2 is kept on.

For Group B, Program 3 (B3), intensity is increased to that of Group B, Program 2. For Group B, Program 4 (B4), intensity is increased to that of Group B, program 2.

In exemplary embodiments, for programming amplitudes, for Group C, Program 1 (C1), the intensity in Program 1 is ramped up until paresthesia is felt. Subsequently, it is ramped down in individual increments until the patient loses paresthesia. This is recorded as the LD paresthesia threshold. Intensity is subsequently decreased to a percentage of PT (e.g., 70%) as a final LD amplitude, with stimulation remaining on for Program 1.

Changing to Program 2 in Group C (C2), intensity in Program 2 is ramped up until paresthesia is felt. Subsequently, intensity is ramped down in individual increments until the patient loses paresthesia. The value is recorded as the HD paresthesia threshold. Intensity is decreased to a percentage of PT (e.g., 65%) and recorded as a final HD amplitude. Stimulation for Program 2 is kept on.

For Group C, Program 3 (C3), intensity is increased to that of Group C, Program 2. For Group C, Program 4 (C4), intensity is increased to that of Group C, program 2.

In exemplary program setup, the program for A2 is copied and pasted into A3 and A4. Similarly, the program for B2 is copied and pasted into B3 and B4. Finally, the program for C2 is copied and pasted into C3 and C4. Accordingly, in this exemplary embodiment, there are 4 programs in each group, with 3 groups created, all with 0.0 mA.

In exemplary embodiments, subsequent to initial setup, a patient may adjust frequency up towards PT in spaced apart increments, e.g., with 4 hours wait time in between adjustments to facilitate accurate assessment of improvement in pain relief. Exemplary embodiments record and/or regulate such adjustments, wait times and assessments. In further exemplary embodiments, objective feedback from patients may be incorporated into such adjustment considerations, for example using informed cycling via sensing changes in posture of the patient or other physically sensed patient aspects, conditions or parameters.

The reader will appreciate that the multimodal modulation techniques described herein, achieved with a composite signal, e.g., frequency, amplitude, or pulse width modulated, and multi-modal modulation, can be utilized for regulation of genes and proteins that modulate the interactions between glial cells and neurons as described herein. Further, the multiplexing techniques may also be used, as has been described herein, for regulation of genes and proteins that modulate the interactions between glial cells and neurons.

Further exemplary embodiments provide a method for managing pain in a subject comprising: applying via at least one electrode a first phase segment of a biphasic signal to a nerve area, the first phase segment having a frequency of between 750 Hz and 1400 Hz; and applying via said at least one electrode a second phase segment of the biphasic signal to said nerve area, the second phase segment having a frequency lower than that of the first phase segment. In further exemplary embodiments, the first phase segment has a frequency of about 1200 Hz (burst) and 900 Hz (average). In further exemplary embodiments, the second phase segment has a frequency of about 50 Hz.

In further exemplary embodiments, the first phase segment and the second phase segment have any of different respective amplitudes, waveform shapes, widths, phase polarities, and phases relative to each other.

In further exemplary embodiments, the biphasic signal is an asymmetric biphasic signal. In further exemplary embodiments, the biphasic signal is a frequency modulated signal. In further exemplary embodiments, the biphasic signal is a phase modulated signal. In further exemplary embodiments, the biphasic signal is a pulse width modulated signal. In further exemplary embodiments, application of the biphasic signal is performed without the administration of a pharmacological substance to the subject.

In further exemplary embodiments, the pulse width of the first phase segment is between about 170 and 400 microseconds.

In further exemplary embodiments, the biphasic signal is derived from a first electric signal having a current amplitude set to a value corresponding to a percentage of perception threshold of the subject.

In further exemplary embodiments, the amplitude of the signals is initially set to zero, with subsequent increase until the patient indicates a perception threshold, with subsequent reduction to a predetermined percentage of perception. In further exemplary embodiments, the percentage perception is between 20% and 90%. In further exemplary embodiments, the percentage of perception is between 65% and 75%.

Further exemplary embodiments include generating a program for said biphasic signal as a first pulse on at least one electrode, and further include generating an exact or altered copy of said program for use on a separate electrode or group of electrodes.

Further exemplary embodiments include generating a program for said biphasic signal as a first pulse on at least one electrode, and further include separately generating programs for at least one separate electrode or group of electrodes, including independently assessing perception for the patient and adjusting amplitude of the signal up or down therefrom.

In further exemplary embodiments, the nerve area comprises a spinal cord nerve area. In further exemplary embodiments, the nerve area comprises a peripheral nerve area. In further exemplary embodiments, the nerve area comprises a cluster of nerves.

In further exemplary embodiments, the first phase segment comprises a priming component. In further exemplary embodiments, the second phase segment comprises a tonic component.

In further exemplary embodiments, the biphasic signal is derived from: a first electric signal having a current amplitude set to a value corresponding to a percentage of priming perception threshold (PPT) of the subject; and a second electric signal having a current amplitude set to a value corresponding to a percentage of tonic perception threshold (TPT).

As used herein, the term "pharmacological substance" means any tangible chemical, drug, medicine or therapeutic substance, either synthetic or naturally occurring, regardless of the form of administration to the subject, that is administered to the body of the subject.

At various places in the present specification, values are disclosed in groups or in ranges. It is specifically intended that the description includes each and every individual sub-combination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

For purposes of clarity and a concise description, features are described herein as part of the same or separate embodiments, however, it will be appreciated that scope of the concepts may include embodiments having combinations of all or some of the features described herein.

It will be apparent to those recently skilled in the art that modifications to the apparatus and process disclosed here in may occur, including substitution of various component values or nodes of connection, without parting from the true spirit and scope of the disclosure as defined by the claims set forth herein. For example, although the embodiments described herein disclose primarily the use of pulsed rectangular signals, other waveform shapes may be similarly used to obtain the same effects. For example, any of a monophasic pulse wave, charge balanced biphasic pulse wave, charge imbalanced biphasic pulse wave, charge balanced biphasic with delay pulse wave, charge balanced biphasic fast reversal wave, and charge balanced biphasic slow reversal wave may be utilized as stimulating waveforms in the multimodal modulation techniques described herein. In addition, other varying electromagnetic fields defined by periodic electric signals having different waveform shapes may be used as well as noise signals and even non-periodic electric signals having irregular nonrepeating shapes.

What is claimed is:

1. A system comprising:
a signal generation module, and
one or more electrodes configured for exposing glial cells of a subject to one or more electromagnetic stimuli and simultaneously exposing neurons of the subject to a second electromagnetic stimulus,
wherein the signal generation module is configured to:
generate a glial stimulation signal by multiplexing, in a time domain, a plurality of signals having at least one different respective parameter;
generate a neuronal stimulation signal; and
provide the glial stimulation signal to a first subgroup of the electrodes and simultaneously provide the neuronal stimulation signal to a second subgroup of the electrodes.

2. The system of claim 1, wherein the at least one different respective parameter includes at least one of amplitude, frequency, relative phase, waveform shape, pulse width, charge balance, or duty cycle.

3. The system of claim 1, wherein glial stimulation signal has a frequency of about 1200 Hz (burst) and 900 Hz (average).

4. The system of claim 1 wherein the neuronal stimulation signal has a frequency of about 50 Hz.

5. The system of claim 1 wherein the pulse width of the glial stimulation signal is between about 170 and 400 microseconds.

6. The system of claim 1, wherein the glial stimulation signal and the neuronal stimulation signal are derived from a first electric signal having a current amplitude set to a value corresponding to a percentage of perception threshold of the subject, wherein amplitude of the signals are initially set to zero, with subsequent increase until the patient indicates a perception threshold, with subsequent reduction to a predetermined percentage of perception and wherein the percentage perception is between 20% and 90%.

7. The system of claim 6, wherein the percentage of perception is between 65% and 75%.

8. The system of claim 1, wherein the glial stimulation signal and the neuronal stimulation signal are derived from a first electric signal having a current amplitude set to a value corresponding to a percentage of perception threshold of the subject, further comprising generating a program for said signals as a first pulse on at least one electrode, and further comprising separately generating programs for at least one separate electrode or group of electrodes, including independently assessing perception for the patient and adjusting amplitude of the signal up or down therefrom.

9. The system of claim 1 wherein the signal generation module is further configured to generate the neuronal stimulation signal by multiplexing a plurality of signals having at least one different respective parameter, wherein the at least one different parameter includes one or more of amplitudes, frequencies, waveform shapes, pulse widths, charge balances, duty cycles or phases relative to each other.

10. The system of claim 9, wherein the system is configured to provide a first component signal and other component signals of the neuronal stimulation signal to a same electrode of the second subgroup of electrodes.

11. The system of claim 9, wherein the system is configured to provide a first component signal and other component signals of the neuronal stimulation signals to different respective electrodes of the second subgroup of electrodes.

12. A method for operating a signal generation module including:
A) connecting the signal generation module to one or more electrode arrays that are already provided to a subject;
B) generating, using the signal generation module, a first varying electromagnetic field at one or more electrodes of the one or more electrode arrays to expose glial cells of the subject to the first varying electromagnetic field; and
C) simultaneously generating, using the signal generation module, a second varying electromagnetic field at one or more electrodes of the one or more electrode arrays to expose neurons of the subject to the second varying electromagnetic field,
wherein one of the first varying electromagnetic field and the second varying electromagnetic field comprise a plurality of component signals multiplexed, in a time domain, to the at least one electrode array.

13. An electromagnetic stimulation system comprising:
memory for storing a plurality of signal parameter programs;
a selection device for selecting one of the plurality of signal parameter programs;
a signal generator controllable by one of the plurality of signal parameter programs and configured for simultaneously generating at least one glial stimulation signal and at least one neuronal stimulation signal different than the at least one glial stimulation signal; and
an output unit configured for connecting the glial stimulation and neuronal stimulation signals to first and second electrode arrays, respectively, already provided to a subject;
wherein the electromagnetic stimulation system is configured to simultaneously provide the at least one glial stimulation signal and at least one neuronal stimulation signal generated by the signal generator in accordance with one of the signal parameter programs to the first and second electrode arrays, respectively, via the output unit for modulating the activity of glial cells of the subject with the at least one glial stimulation electric signal and for modulating the activity of neurons of the subject with the at least neuronal stimulation electric field,
wherein one of the glial stimulation and neuronal stimulation electric signals comprises a plurality of component signals multiplexed, in a time domain, to the respective electrode array to which the glial stimulation and neuronal stimulation signals are provided.

14. The system of claim 13, wherein the at least one glial stimulation signal comprises a first subgroup of component signals multiplexed to the first electrode array, and the at least one glial stimulation signal further comprising at least one other component signal having any of a different respective amplitude, frequency, relative phase, waveform shape, pulse width, charge balance, or duty cycle than one of the first subgroup of component signals.

15. The system of claim 14, wherein the first electrode array comprises a first subgroup of electrodes, and the at least one other component signal is provided to at least one electrode of the first subgroup of electrodes different than an electrode of the first subgroup of electrodes to which the first subgroup of component signals are multiplexed.

16. The system of claim 13, wherein the at least one neuronal stimulation signal comprises at least a first component signal and other component signals, the first component signal and the other component signals having any of a different respective amplitudes, frequencies, waveform shapes, pulse widths, charge balances, duty cycles or phases relative to each other.

17. The system of claim 16, wherein the second electrode array comprises a second subgroup of electrodes, and the first component signal and the other component signals are provided to a same electrode of the second subgroup of electrodes.

18. The system of claim 16, wherein the first component signal and the other component signals are provided to different electrodes of the second subgroup of electrodes.

19. A system comprising:
a signal generation module, and
one or more electrodes configured for exposing glial cells of a subject to a first electromagnetic stimulus and simultaneously exposing neurons of the subject to a second electromagnetic stimulus,
wherein the signal generation module is configured for having an operating mode for providing a priming signal to a first subgroup of the electrodes and simultaneously providing a tonic signal to a second subgroup of the electrodes, and
wherein one of the priming signal and the tonic signal comprises a plurality of component signals multiplexed, in a time domain, to at least one electrode of the respective subgroup of electrodes to which the priming signal or the tonic signal is provided.

20. The system of claim 19, wherein the priming signal comprises a first subgroup of component signals multiplexed to at least one electrode of the first subgroup of electrodes, and the priming signal further comprising at least one other component signal having any of a different respective amplitude, frequency, relative phase, waveform shape, pulse width, charge balance, or duty cycle than one of the first subgroup of component signals.

21. The system of claim 20, wherein the at least one other component signal is provided to an electrode of the first subgroup of electrodes different than the at least one electrode of the first subgroup of electrodes to which the first subgroup of component signals are multiplexed.

22. The system of claim 19, wherein the tonic signal comprises at least a first component signal and a second component signal, the first component signal and the second component signal having any of a different respective amplitudes, frequencies, waveform shapes, pulse widths, charge balances, duty cycles or phases relative to each other.

23. The system of claim 22, wherein the first component signal and the second component signal are provided to a same electrode of the second subgroup of electrodes.

24. The system of claim 22, wherein the first component signal and the second component signal are provided to different electrodes of the second subgroup of electrodes.

25. A method for operating a signal generation module including:
A) connecting the signal generation module to one or more leads that are already provided to a subject;
B) generating, using the signal generation module, a first varying electromagnetic field at one of the leads to expose glial cells of the subject to the first varying electromagnetic field; and
C) simultaneously generating, using the signal generation module, a second varying electromagnetic field at a different one of the leads to expose neurons of the subject to the second varying electromagnetic field,
wherein one of the first varying electromagnetic field and the second varying electromagnetic field comprise a plurality of component signals multiplexed, in a time domain, to the at least one lead.

* * * * *